US008198326B2

(12) United States Patent
Scholz

(10) Patent No.: US 8,198,326 B2
(45) Date of Patent: *Jun. 12, 2012

(54) PHENOLIC ANTISEPTIC COMPOSITIONS AND METHODS OF USE

(75) Inventor: Matthew T. Scholz, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1051 days.

This patent is subject to a terminal disclaimer.

(21) Appl. No.: 10/936,171

(22) Filed: Sep. 7, 2004

(65) Prior Publication Data

US 2006/0052452 A1    Mar. 9, 2006

(51) Int. Cl.
| | |
|---|---|
| A01N 37/00 | (2006.01) |
| A01N 31/14 | (2006.01) |
| A01N 31/08 | (2006.01) |
| A61K 31/19 | (2006.01) |
| A61K 31/075 | (2006.01) |
| A61K 31/05 | (2006.01) |

(52) U.S. Cl. .................. 514/557; 514/721; 514/731
(58) Field of Classification Search ............ 514/557, 514/721, 731
See application file for complete search history.

(56) References Cited

U.S. PATENT DOCUMENTS

| | | | |
|---|---|---|---|
| 2,818,390 A | 12/1957 | Beaver et al. | |
| 4,010,252 A | 3/1977 | Hewitt | |
| 4,067,997 A | 1/1978 | Kabara | |
| 4,438,100 A | 3/1984 | Balslev et al. | |
| 4,485,091 A | 11/1984 | Fitton | |
| 4,512,987 A | 4/1985 | Schindlery et al. | |
| 4,514,384 A | 4/1985 | Gallina | |
| 4,894,220 A | 1/1990 | Nabi et al. | |
| 4,931,282 A | 6/1990 | Asmus et al. | |
| 4,963,555 A | 10/1990 | Jones et al. | |
| 4,983,595 A | 1/1991 | Benjamin et al. | |
| 4,985,242 A | 1/1991 | Sekine et al. | |
| 5,084,096 A | 1/1992 | Stovicek | |
| 5,112,617 A * | 5/1992 | Criscuolo et al. ............ 424/434 |
| 5,192,802 A | 3/1993 | Rencher | |
| 5,208,257 A | 5/1993 | Kabara | |
| 5,225,473 A | 7/1993 | Duan | |
| 5,314,694 A | 5/1994 | Gale et al. | |
| 5,314,915 A | 5/1994 | Rencher | |
| 5,318,955 A | 6/1994 | Mueller et al. | |
| 5,326,567 A | 7/1994 | Capelli | |
| 5,408,022 A | 4/1995 | Imazato et al. | |
| 5,424,059 A | 6/1995 | Prencipe et al. | |
| 5,429,819 A | 7/1995 | Oka et al. | |
| 5,462,749 A | 10/1995 | Rencher | |
| 5,482,931 A | 1/1996 | Harris et al. | |
| 5,665,776 A | 9/1997 | Yu et al. | |
| 5,708,023 A | 1/1998 | Modak et al. | |
| 5,728,756 A | 3/1998 | Gaffar et al. | |
| 5,817,325 A | 10/1998 | Sawan et al. | |
| 5,951,993 A | 9/1999 | Scholz et al. | |
| 5,965,610 A | 10/1999 | Modak et al. | |
| 6,022,551 A | 2/2000 | Jampani et al. | |
| 6,054,143 A | 4/2000 | Jones | |
| 6,071,866 A | 6/2000 | Fujiwara et al. | |
| 6,094,414 A | 7/2000 | Taira et al. | |
| 6,123,933 A | 9/2000 | Hayama et al. | |
| 6,165,494 A | 12/2000 | Picciano | |
| 6,171,611 B1 | 1/2001 | Picciano | |
| 6,187,332 B1 | 2/2001 | Gern et al. | |
| 6,210,695 B1 | 4/2001 | Beerse et al. | |
| 6,211,243 B1 | 4/2001 | Johnson | |
| 6,214,866 B1 | 4/2001 | Drogemoller et al. | |
| 6,217,877 B1 | 4/2001 | Weidner | |
| 6,224,898 B1 | 5/2001 | Balogh et al. | |
| 6,238,682 B1 | 5/2001 | Klofta et al. | |
| 6,287,577 B1 | 9/2001 | Beerse et al. | |
| 6,375,984 B1 | 4/2002 | Kim | |
| 6,383,523 B1 | 5/2002 | Murad | |
| 6,440,405 B1 | 8/2002 | Cooper et al. | |
| 6,462,025 B2 | 10/2002 | Vishnupad | |
| 6,468,521 B1 | 10/2002 | Pedersen et al. | |
| 6,494,856 B1 | 12/2002 | Zygmont | |
| 6,500,861 B1 | 12/2002 | Wider | |
| 6,517,854 B2 | 2/2003 | Stack | |
| 6,534,075 B1 | 3/2003 | Hei et al. | |
| 6,555,566 B2 | 4/2003 | Ponikau | |
| 6,559,189 B2 | 5/2003 | Baker, Jr. et al. | |
| 6,579,906 B2 | 6/2003 | Cooper et al. | |
| 6,590,051 B1 | 7/2003 | Carter et al. | |
| 6,635,676 B2 | 10/2003 | Baker, Jr. et al. | |
| 6,746,635 B2 | 6/2004 | Mathiowitz et al. | |

(Continued)

FOREIGN PATENT DOCUMENTS

DE          43 02 812          8/1994

(Continued)

OTHER PUBLICATIONS

Deacon, J. Microbial World, Armillaria mellea and other wood-decay fungi, 2007, pp. 1-14.*
Rutala et al. Infect. Control Hosp. Epidemiol. Jun. 1997, vol. 18, No. 6, pp. 417-421.*
*Disinfection, Sterilization, and Preservation*, $2^{nd}$ Ed. Edited by Seymour S. Block, Chapter 14, Lea & Febiger, Philidelphia PA, (1977).
Federal Register, 21 CFR Parts 333 and 369, Tentative Final Monograph for Healthcare Antiseptic Drug Products; Proposed Rule, (scrub cup method) (1994).
Gloor, M., et al., "Triclosan, ein dermatologishes Lokaltherapeutikum" Hautarzt, vol. 53, pp. 724-729, XP002391035, (Nov. 2002).
Hill, R.L. and M.W. Casewell, "The in-vitro activity of povidone-iodine cream against *Staphylococus aureas* and its bioavailability in nasal secretions", *Journal of Hospital Infection*, vol. 45, pp. 198-205 (2000).

(Continued)

Primary Examiner — Samira Jean-Louis

(57) ABSTRACT

Antimicrobial compositions, especially those useful when applied topically, particularly to mucosal tissues (i.e., mucous membranes), including an antiseptic such as halogenated phenols, bisphenols, diphenyl ethers, anilides and derivatives thereof, and combinations thereof. The compositions can also include an enhancer component, a surfactant, a hydrophobic component, and/or a hydrophilic component. Such compositions provide effective topical antimicrobial activity and are accordingly useful in the treatment and/or prevention of conditions that are caused, or aggravated by, microorganisms (including viruses).

25 Claims, No Drawings

U.S. PATENT DOCUMENTS

| | | | |
|---|---|---|---|
| 6,951,642 | B2 | 10/2005 | Scholz et al. |
| 7,030,203 | B2 | 4/2006 | Mosbey et al. |
| 2002/0013305 | A1 | 1/2002 | Calvin |
| 2002/0025344 | A1 | 2/2002 | Newman et al. |
| 2002/0031556 | A1 | 3/2002 | Lindahl |
| 2002/0037268 | A1 | 3/2002 | Stack |
| 2002/0058010 | A1 | 5/2002 | Picard-Lesboueyries |
| 2002/0193417 | A1 | 12/2002 | Seidel et al. |
| 2003/0228376 | A1 | 12/2003 | Mody et al. |
| 2004/0009130 | A1 | 1/2004 | Detore et al. |
| 2004/0091428 | A1 | 5/2004 | Libin |
| 2005/0058673 | A1 | 3/2005 | Scholz et al. |
| 2005/0089539 | A1 | 4/2005 | Scholz et al. |
| 2006/0029569 | A1 | 2/2006 | Scholz et al. |
| 2006/0034798 | A1 | 2/2006 | Mosbey et al. |
| 2006/0051384 | A1 | 3/2006 | Scholz et al. |
| 2006/0051385 | A1 | 3/2006 | Scholz |
| 2006/0099237 | A1 | 5/2006 | Modak et al. |
| 2007/0020029 | A1 | 1/2007 | Baumann et al. |

FOREIGN PATENT DOCUMENTS

| | | |
|---|---|---|
| EP | 0 375 827 | 4/1990 |
| GB | 882 742 | 11/1961 |
| GB | 882742 | 11/1961 |
| GB | 2 323 784 | 7/1998 |
| GB | 2 338 649 | 12/1999 |
| JP | 53 066415 | 6/1978 |
| JP | 60-44539 | 3/1985 |
| JP | 63-0166837 | 2/1987 |
| JP | 63-130541 | 6/1988 |
| JP | 8-151326 | 11/1994 |
| JP | 9-510976 | 11/1997 |
| JP | 2002-145736 | 5/2002 |
| WO | WO 93/15018 | 8/1993 |
| WO | WO93/21906 | 11/1993 |
| WO | WO95/24179 | 9/1995 |
| WO | WO 95-26134 | 10/1995 |
| WO | WO97/00076 | 1/1997 |
| WO | WO97/16168 | 5/1997 |
| WO | WO 98/09520 | 3/1998 |
| WO | WO99/22703 | 5/1999 |
| WO | WO 99/59538 | 11/1999 |
| WO | WO99/60998 | 12/1999 |
| WO | WO 99/66793 | 12/1999 |
| WO | WO 0128552 A2 * | 4/2001 |
| WO | WO02/100244 | 12/2002 |
| WO | WO03/022211 | 3/2003 |
| WO | WO03/028767 | 4/2003 |
| WO | WO 03-032948 | 4/2003 |
| WO | WO 2004-052308 | 6/2004 |
| WO | WO 2006/029255 A2 | 3/2006 |
| WO | WO 2006/029278 A2 | 3/2006 |
| WO | WO 2006/029278 A3 | 3/2006 |
| WO | WO 2006/029351 A2 | 3/2006 |
| WO | WO 2006/029351 A3 | 3/2006 |

OTHER PUBLICATIONS

Kiser, K., et al., "Development and Characterization of a Staphylococcus aureus Nasal Colonization Model in Mice", Infect and Immunity, vol. 67, No. 10, pp. 5001-5006 (1999).
Kostenbauer, H. B., Chapter 44 in Disinfection, Sterilization, and Preservation, First addition, C. A. Lawrence and S.S. Block (1968).
MacFarlane, D.E., "Prevention and treatment of catheter-associated urinary tract invections", J. of Infection, vol. 10, pp. 96-106 (1985).
May, et al., "Time-kill studies of tea tree oils on clinical isolates", J. of Antimicrobial Chemotherapy, vol. 45, pp. 639-643 (2000).
Nicoletti, G., et al., "The Antimicrobial Activity in vitro of chlorhexidine, a mixture of isothiazolinones (Kathon CG) and cetyl trimethyl ammonium bromide (CTAB)", Journal of Hospital Infection, vol. 23, pp. 87-111, (1993).
Perl, T., et al., "New Approaches to Reduce Staphylococcus aureus Nosocomial Infection Rates: Treating S. aureus Nasal Carriage", Ann. Pharmacother, vol. 32, pp. S7-S16 (1998).
Perez-Roth, E., et al., "Mupirocin resistance in methicillin-Staphylococcus aureus clinical isolates in a Spanish hospital", Diag. Micro. Infect. Dis., vol. 43, pp. 123-128 (2002).
Sawhney, A.S., et al., "Bioerodible Hydrogels Based on Photopolymerized Poly(ethylene glycol)-co-poly($\alpha$-hydroxy acid) Diacrylate Macromers" Macromolecules, vol. 26, pp. 581-587 (1993).
Sciarra and Cutie, "Aerosols," in Remington's Pharmaceutical Sciences, 18th edition, pp. 1694-1712 (1990).
Vorum, Henrik, et. al., "Solubility of Long-Chain Fatty Acids in Phosphate Buffer at pH 7.4", Biochimica et. Biophysica Acta., vol. 1126, pp. 135-142, (1992).
Watanabe, et al., "Low Concentrations of Mupirocin in the Pharynx following Intranasal Application May Contribute to Mupirocin Resistance in Methicillin-Resistant Staphylococcus aureus", J. Clin. Micro., vol. 39, No. 10, pp. 3775-3777 (2001).
Williams, J.D., et al., "Trials of Five Antibacterial Creams in the Control of Nasal Carriage of Staphylococcus aureus", The Lancet, vol. 290, Issue 7512, pp. 390-392 (Aug. 1967).
International Search Report for PCT/US2005/032024 (6 pgs.).
Written Opinion of the International Searching Authority for PCT/US2005/032024 (9 pgs.).
ABDA: Rezepturhinweise: Triclosan in Dermatika"NRF—Neues Rezeptur Formularium," Apr. 16, 2004, p. 1-4 (XP002391034). No English Abstract Available.
English Translation of ABDA: Rezepturhinweise: Triclosan in Dermatika"NRF—Neues Rezeptur Formularium," Apr. 16, 2004, p. 1-4 (XP002391034).
Boddie et al., "Evaluation of Postmiling Teat Germicides Containing Lauricidin® Saturated Fatty Acids, and Lactic Acid," Journal of Dairy Science, Jun. 1992; 75(6):1725-1730.
Chavigny, K.H., "The use of polymixin B as a urethral lubricant to reduce the post-instrumental incidenec of bacteiuria in females," Int. J. Nurs. Stud., 1975;12:33-42.
Disinfection, Sterilization, and Preservation, 4th Ed. Edited by Seymour S. Block, Chapter 13, Lea & Febiger, Philadelphia, PA, 1991.
Fraise et al., "Choosing Disinfectants," Journal of Hospital Infections, 1999;43:255-264.
Gillespie et al., "Prevention of Catheter Infection of Urine in Female Patients," British Medical Journal, 1962:13-16.
Kostiala et al., "Effect of nitrofurantoin and methenamine hippurate prophylaxis on bacteria and yeasts in the urine of patients with an indwelling catheter," J of Hospital Infection, 1982;3:347-364.
Morgan, "Urinary tract infection in hospitalized patients," Canadian Hospital, 1973:27-30.
"Paraffin Wax," MSDS, 2003, [online]. <http://www.inchem.org/documents/icsc/icsc/eics1457.html.> 2 pgs.
Seymour S., Disinfection, Sterilization, and Preservation, pp. 217-218, (1991).
Gokalp et al. "Antimicrobial Screening of Mentha piperita Essential Oils, J. Agric", Food Chem. 2002, 50, 3943-3946.
Lesch et al. "The Permeability of Human Oral Mucosa and Skin to Water" Journal of Journal of Dental Research, vol. 68, No. 9, 1345-1349 (1989) http://jdr.sagepub.com/cgi/content/abstract/68/9/1345.
Fuls et al., "Alternative Hand Contamination Technique to Compare the Activities of Antimicrobial and Nonantimicrobial Soaps under Different Test Conditions", Applied and Environmental Microbiology, vol. 74, No. 12, 3739-3744(2008).

* cited by examiner

PHENOLIC ANTISEPTIC COMPOSITIONS AND METHODS OF USE

BACKGROUND

The use of antimicrobial agents plays an important part in current medical therapy. This is particularly true in the fields of dermatology as well as skin and wound antisepsis, where the most effective course of treatment for skin or mucous membranes, which are afflicted with bacterial, fungal, or viral infections or lesions, frequently includes the use of a topical antimicrobial agent, such as antibiotics. For decades medicine has relied primarily upon antibiotics to fight systemic as well as topical infections.

Antibiotics are organic molecules produced by microorganisms that have the capacity in dilute solutions (e.g., solutions less than 10 µg/ml and often less than 1 µg/ml) to destroy or inhibit the growth of bacteria and other microorganisms. They are generally effective at very low levels and are often safe with very few, if any, side effects. Antibiotics are commonly of a narrow spectrum of antimicrobial activity. Furthermore, they often act on very specific sites in cell membranes or on very specific metabolic pathways. This can tend to make it relatively easy for bacteria to develop resistance to the antibiotic(s) (i.e., the genetically acquired ability to tolerate much higher concentrations of antibiotic) either through natural selection, transmission of plasmids encoding resistance, mutation, or by other means. Not only does resistance eliminate the ability of a medication to treat an affliction, but it can also put the patient at further risk, especially if the antibiotic is one that is routinely used systemically.

In the past few decades it has become well established that colonization of the anterior nares with *Staphylococcus aureus* (SA) can lead to multiple problems. Medicine has relied primarily upon antibiotics for nasal decolonization. For example, bacitracin, neomycin sulfate, polymyxin B sulfate, gentamicin, framycetin-gramicidin, lysostaphin, methicillin, rifampin, tobramycin, nystatin, mupirocin, and combinations thereof, have been used with varying success for nasal decolonization.

For example, nasal colonization with SA in presurgical patients has resulted in higher infection rates and higher rates of other nosocomial infections such as catheter infections. Nasal colonization with SA in hemodialysis patients has resulted in a much higher incidence of blood stream infections. Furthermore, it has been well established that the anterior nares is the ecological niche for SA colonization and thus spread of methicillin resistant *staphylococcus aureus* (MRSA) in a hospital or other health care facilities in the event of an outbreak can be mitigated by decolonizing the anterior nares of patients and healthcare workers.

Mupirocin, marketed as the calcium salt in Bactroban Nasal by Glaxo Smith Kline, is the only antibiotic approved by the Food and Drug Administration for nasal decolonization use in the United States. For example, there are multiple reports of resistance to mupirocin when used as a nasal decolonizing agent. Resistance rates have been reported as high as 25% and even as high as 50% (see, for example, E. Perez-Roth et al., *Diag. Micro. Infect. Dis.*, 43:123-128 (2002) and H. Watanabe et al., *J. Clin. Micro.*, 39(10): 3775-3777 (2001)). Even though presurgical decolonization of the anterior nares using mupirocin has been shown to decrease the risk of surgical site infection by as much as 2 to 10 times (T. Perl et al., *Ann. Pharmacother.*, 32:S7-S16 (1998)), the high resistance rates to this antibiotic make it unsuitable for routine use.

Antiseptics, on the other hand, are synthetic molecules that destroy or inhibit microorganisms and virus by inhibiting metabolic pathways or altering the cell envelope or both. They tend to have broader spectrum of antimicrobial activity and often act by nonspecific means such as disruption of cell membranes, oxidation of cellular components, denaturation of proteins, etc. This nonspecific activity makes it difficult for microorganisms to develop clinical resistance to antiseptics. For example, there are very few reports of clinical resistance to antiseptics such as iodine, lower alcohols (ethanol, propanol, etc.), chlorhexidine, quaternary amine surfactants, chlorinated phenols, and the like. Some of these compounds, however, need to be used at concentrations that often result in irritation or tissue damage, especially if applied repeatedly. Furthermore, unlike antibiotics, many antiseptics are not active in the presence of high levels of organic compounds. For example, formulations containing iodine or quaternary ammonium compounds have been reported to be inactivated by the presence of organic matter such as that in nasal or vaginal secretions, and perhaps even on skin.

Many antiseptic compounds are viewed as irritants. For example, compositions containing iodine and/or chlorhexidine have been reported to cause skin and mucosal tissue irritation. This is particularly true for sensitive mucosal tissues, such as the anterior nares, nasal and esophageal cavities, which can have a high level of microbial colonization in certain otherwise healthy individuals, as well as individuals with infectious diseases such as chronic sinusitis. Additionally, due to the irritating nature many of these compounds may be unsuitable for application to irritated or infected dermal tissue to treat skin conditions, such as lesions from impetigo and shingles.

Also, for certain applications, especially in the nose and mouth, it is particularly desirable for the compositions to have little or no color, little or no odor, and an acceptable taste. Many antiseptics have undesirable characteristics, such as iodine and iodophors, which have an orange to brown color and a definite odor at concentrations typically employed for antisepsis.

Chlorhexidine gluconate (in combination with neomycin sulfate) has been suggested for use in nasal decolonization with limited success. For example, Naseptin is an antibiotic emulsified cream comprising neomycin sulphate (3250 units/g) and chlorhexidine gluconate (0.1 wt-%) that in combination destroys bacteria. The product also contains arachis oil, cetostearyl alcohol/ethylene oxide concentrate, and cetostearyl alcohol in a water base. The product must be used 4 times/day over 10 days to eradicate nasal carriage of staphylococci. In addition, U.S. Pat. No. 6,214,866 discloses the use of chlorhexidine in combination with the antibiotic mupirocin.

Povidone-iodine has also been suggested for use in nasal decolonization (R. L. Hill and M. W. Casewell, *Journal of Hospital Infection*, 2000, Vol. 45, 198-205). Betadine Cream (5 wt-% povidone iodine) has been found to kill methicillin resistant *staphylococcus aureus* in vitro in an enrichment culture technique. Addition of nasal secretions decreased the activity of the povidone-iodine by 80-90% by reaction of the free iodine with the organic load. Other drawbacks of 5% povidone-iodine for use in patients included: 1) a very dark brown color, 2) a low pH, which can cause irritation, 3) a strong iodine odor.

The formulation of components can affect the performance and potential irritation of antimicrobial agents. For example, many conventional antimicrobial compositions are too low in viscosity and/or too hydrophilic in nature to maintain sufficient substantivity and persistence to provide sufficient antimicrobial activity on moist tissue, such as the anterior nares or open, exuding, or infected lesions. It has been reported that the presence of solvents can diminish the antimicrobial activity of many antiseptics. Furthermore, it has been reported that many surfactants can reduce the efficacy of antiseptics by sequestering the antiseptic in micelles. (H. B. Kostenbauer, Chapter 44 in *Disinfection, Sterilization, and Preservation*, First addition, 1968, C. A. Lawrence and S. S. Block). Additionally, surfactants are often implicated in contributing to irritation.

Thus, there is still a need for effective antimicrobial compositions that develop little resistance and are well tolerated when used on mammalian tissue and especially on moist mammalian tissue such as in the nasal passages, anterior nares, vagina, and wounds.

SUMMARY OF THE INVENTION

The present invention provides antimicrobial compositions and methods of using and making the compositions. Such compositions are typically useful when applied topically, particularly to mucosal tissues (i.e., mucous membranes), although a wide variety of surfaces can be treated. They can provide effective reduction, prevention, or elimination of microbes, particularly bacteria, fungi, and viruses. Preferably, the microbes are of a relatively wide variety such that the compositions of the present invention have a broad spectrum of activity.

Compositions of the present invention provide effective topical antimicrobial activity and are accordingly useful in the local treatment and/or prevention of conditions that are caused, or aggravated by, microorganisms (including viruses, bacteria, fungi, mycoplasma, and protozoa) on various tissues such as skin, wounds, and/or mucous membranes.

Significantly, certain embodiments of the present invention have a very low potential for generating clinical microbial resistance. Thus, such compositions can be applied multiple times over one or more days to treat topical infections or to eradicate unwanted bacteria (such as nasal colonization of *Staphylococcus aureus*). Furthermore, compositions of the present invention can be used for multiple treatment regimens on the same patient without the fear of generating antimicrobial resistance. This can be particularly important for chronically ill patients who are in need of decolonization of the anterior nares before hemodialysis, for example, or for antiseptic treatment of chronic wounds such as diabetic foot ulcers.

Also, preferred compositions of the present invention have a generally low irritation level for skin, skin lesions, and mucosal membranes (including the anterior nares, nasal cavities, and nasopharyngeal cavity). Also, certain preferred compositions of the present invention are substantive (i.e., resist removal by fluids) for relatively long periods of time to ensure adequate efficacy.

Compositions of the present invention include an antiseptic selected from the group consisting of diphenyl ethers, phenols, halogenated phenols, bisphenols, resorcinols and its derivatives, anilides, and combinations thereof. Importantly, the compositions of the present invention are capable of destroying microorganisms on or in mammalian tissue. Therefore, the concentrations employed are generally greater than those that have been used to simply preserve certain topically applied compositions, i.e., prevent the growth of microorganism in topical compositions for purposes other than antisepsis. For example, the concentration may be at least 0.1 wt %, preferably at least 0.2 wt % and more preferably at least 0.5 wt %. Commonly, the antiseptics may be employed at concentration of at least 1 wt-%, preferably at least 2 wt-% and often at least 3% by weight of the composition. All weight percents are based on the total weight of a "ready to use" or "as used" composition.

Depending on the application, many of these compounds at these concentrations can be irritating if delivered in simple aqueous or hydrophilic vehicle formulations. Many of the compositions of the present invention incorporate a substantial amount of a lipophilic or hydrophobic phase. The hydrophobic phase is comprised of one or more water insoluble components. If delivered in a hydrophobic phase, the irritation can be significantly reduced. The incorporation of the hydrophobic phase may significantly reduce the irritation potential of the present compositions. Preferred hydrophobic phase components have a solubility in water of less than 0.5% by weight and often less than 0.1% by weight at 23° C. In addition, the antiseptic is preferably present at a concentration approaching or preferably exceeding the solubility limit of the hydrophobic phase.

Importantly, the compositions also have sufficient viscosity to prevent inhalation into the lungs if used in the nose for applications such as nasal decolonization. The relatively high viscosity of the compositions of the present invention also minimizes migration that can be associated with other compositions thus reducing irritation and mess. Despite the presence of the hydrophobic phase many of the antiseptic containing compositions exhibit very effective and rapid antimicrobial activity.

In addition, antimicrobial compositions that include hydrophilic components such as polyols (e.g., glycerin and polyethylene glycols) that themselves have little or no antimicrobial activity can considerably enhance the antimicrobial activity of the compositions. Preferably, the hydrophilic component includes a glycol, a lower alcohol ether, a short chain ester, and combinations thereof, wherein the hydrophilic component is soluble in water in an amount of at least 20 wt-% at 23° C.

The compositions of the present invention are preferably free of antibiotics.

Preferably, the compositions also include a surfactant selected from the group of sulfonate, a sulfate, a phosphonate, a phosphate, an amphoteric surfactant, a poloxamer, a cationic surfactant, or mixtures thereof. Preferably, the compositions also include an enhancer component comprising an alpha-hydroxy acid, a beta-hydroxy acid, a chelating agent, a (C1-C4)alkyl carboxylic acid, a (C6-C12)aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof.

The present invention also provides various methods of use of compositions of the present invention. In one embodiment, the present invention provides a method of preventing and/or treating an affliction caused, or aggravated by, a microorganism on mammalian tissue, such as skin and/or a mucous membrane. The method includes contacting the mammalian tissue with an antimicrobial composition of the present invention.

In one embodiment, the present invention provides a method of decolonizing at least a portion of the nasal cavities, anterior nares, and/or nasopharynx of a subject of microorganisms. The method includes contacting the nasal cavities, anterior nares, and/or nasopharynx with an antimicrobial composition of the present invention in an amount effective to kill one or more microorganisms in or on tissue.

In one embodiment, the present invention provides a method of decolonizing at least a portion of the throat/esophagus of a subject of microorganisms. The method includes contacting the esophageal cavity with an antimicrobial composition of the present invention in an amount effective to kill one or more microorganisms in or on the tissue in the throat.

In one embodiment, the present invention provides a method of decolonizing at least a portion of the throat/esophagus of a subject of microorganisms. The method includes contacting the oral and/or nasal cavity with an antimicrobial composition of the present invention in an amount effective to allow a sufficient quantity of the composition to pass down the throat to reduce or eliminate bacterial colonization in or on the tissue in the throat.

In one embodiment, the present invention provides a method of decolonizing at least a portion of the oral cavity of a subject of microorganisms. The method includes contacting the oral cavity with an antimicrobial composition of the present invention in an amount effective to kill one or more microorganisms in or on the soft tissue in the oral cavity.

In one embodiment, the present invention provides a method of treating a respiratory affliction (e.g., chronic sinusitis) in a subject. The method includes contacting at least a portion of the respiratory system (particularly the upper respiratory system including the nasal cavities, anterior nares, and/or nasopharynx) with an antimicrobial composition of the present invention in an amount effective to reduce or eliminate bacterial colonization in or on the soft tissue in the respiratory system.

In one embodiment, the present invention provides a method of treating impetigo on the skin of a subject. The method includes contacting the affected area with an antimicrobial composition of the present invention in an amount effective to reduce or eliminate clinical signs of infection.

In other embodiments, the present invention provides methods for killing or inactivating microorganisms. Herein, to "kill or inactivate" means to render the microorganism ineffective by killing them (e.g., bacteria and fungi) or otherwise rendering them inactive (e.g., viruses). The present invention provides methods for killing bacteria such as *Staphylococcus* spp., *Streptococcus* spp., *Escherichia* spp., *Enterococcus* spp. (including antibiotic resistant strains such as vancomycin resistant *Enterococcu*), and *Pseudomonas* spp. bacteria, and combinations thereof, and more particularly *Staphylococcus aureus* (including antibiotic resistant strains such as methicillin resistant *Staphylococcus aureus*), *Staphylococcus epidermidis*, *Escherichia coli* (*E. coli*), *Pseudomonas aeruginosa* (*Pseudomonas* ae.), and *Streptococcus pyogenes*, which often are on or in the skin or mucosal tissue of a subject. The method includes contacting the microorganism with an antimicrobial composition of the present invention in an amount effective to kill one or more microorganisms (e.g., bacteria and fungi) or inactivate one or more microorganisms (e.g., viruses, particularly herpes virus).

For example, in one embodiment, the present invention provides a method of killing or inactivating microorganisms in the nose or nasal cavity of a subject. The method includes contacting the affected area with an antimicrobial composition of the present invention in an amount effective to kill one or more microorganisms on or in the tissue in the nose or nasal cavity.

The compositions of the present invention can also be used for providing residual antimicrobial efficacy on a surface that results from leaving a residue or imparting a condition to the surface (e.g., skin, in the anterior nares, mucosal tissue, wound, or medical device that comes in contact with such tissues, but particularly skin, mucosal tissue, and/or wound) that remains effective and provides significant antimicrobial activity. This is accomplished by providing compositions with relatively high concentrations of a hydrophobic component (generally greater than 30% by weight, preferably greater than 40% by weight and most preferably greater than 50% by weight) and/or a composition with a relatively high viscosity, e.g., in excess of 1,000 cps and preferably in excess of 10,000 cps when measured by the Viscosity Test.

For example, in one embodiment, the present invention provides a method of providing residual antimicrobial efficacy on the skin, in the anterior nares, mucosal tissue, and/or in a wound of a subject, the method includes contacting the skin, mucosal tissue, and/or wound with an antimicrobial composition of the present invention in an amount effective to kill one or more microorganisms.

Methods of manufacture are also provided.

DEFINITIONS

The following terms are used herein according to the following definitions.

"Effective amount" means the amount of the one or more antiseptic components when in a composition, as a whole, provides antimicrobial (including, for example, antiviral, antibacterial, or antifungal) activity that when applied in an amount, at a frequency, and for a duration, that reduces, prevents, or eliminates one or more species of microbes such that an acceptable level of the microbe results. Typically, this is a level low enough not to cause clinical symptoms, and is desirably a non-detectable level. It should be understood that in the compositions of the present invention, the concentrations or amounts of the components, when considered separately, may not kill to an acceptable level, or may not kill as broad a spectrum of undesired microorganisms, or may not kill as fast; however, when used together such components provide an enhanced antimicrobial activity (as compared to the same components used alone under the same conditions). Also, it should be understood that (unless otherwise specified) the listed concentrations of the components are for "ready to use" or "as used" compositions. The compositions can be in a concentrated form. That is, certain embodiments of the compositions can be in the form of concentrates that would be diluted by the user with an appropriate vehicle.

"Hydrophilic" or "water-soluble" refers to a material that will disperse or dissolve in deionized water (or other aqueous solution as specified) at a temperature of 23° C. in an amount of at least 7% by weight, preferably at least 10% by weight, more preferably at least 20% by weight, even more preferably at least 25% by weight, even more preferably at least 30% by weight, and most preferably at least 40% by weight, based on the total weight of the hydrophilic material and the water. The component is considered dissolved if after thoroughly mixing the compound with water at 60° C. for at least 4 hours and allowing this to cool to 23-25° C. for 24 hours, and mixing the composition thoroughly it appears uniform clear solution without visible cloudiness, phase separation, or precipitate in a jar having a path length of 4 cm. Typically when placed in 1×1 cm cell, the samples exhibit greater than 70% transmission measured in a suitable spectrophotometer at a wavelength of 655 nm. Water dispersible hydrophilic materials disperse in water to form uniform cloudy dispersions after vigorous shaking of a 5% by weight mixture of the hydrophilic component in water. Preferred hydrophilic components are water-soluble.

"Hydrophobic" or "water-insoluble" refers to a material that will not significantly dissolve in deionized water at 23° C. "Not significantly" means that the solubility in water of the material is less than 5% by weight, preferably less than 1% by weight, more preferably less than 0.5% by weight, and even more preferably less than 0.1% by weight, based on the total weight of the hydrophobic material and the water. Solubility can be determined by thoroughly mixing the compound with water at the appropriate concentration at 23° C. for at least 24 hours (or at elevated temperature if that is necessary to dissolve the compound), allowing the mixture to sit at 23-25° C. for 24 hours, and observing the sample. In a glass jar with a 4 cm path length the sample should have evidence of a second phase which can be liquid or solid and may be separated on the top, bottom, or distributed throughout the sample. For crystalline compounds care must be taken to avoid producing a supersaturated solution. The components should be mixed and observed. Cloudiness or presence of a visible precipitate or separate phase indicates that the solubility limit has been exceeded. Typically when placed in 1×1 cm cell the sample has less than 70% transmission measured in a suitable spectrophotometer at a wavelength of 655 nm. For solubility determinations less than that which can be observed with the naked eye, the solubility is determined using radio labeled compounds as described under "Conventional Solubility Estimations" in *Solubility of Long-Chain Fatty Acids in Phosphate Buffer at pH 7.4*, Henrik Vorum, et. al., *Biochimica et. Biophysica Acta.* 1126 (1992) 135-142.

"Stable" means physically stable or chemically stable, which are both defined in greater detail below. Preferred compositions are both chemically and physically stable.

"Microorganism" or "microbe" refers to bacteria, yeast, mold, fungi, protozoa, mycoplasma, as well as viruses (including lipid enveloped RNA and DNA viruses).

"Antibiotic" means an organic chemical compound produced by microorganisms that has the ability in dilute concentrations to destroy or inhibit microorganisms and is used to treat infectious disease. This may also encompass semisynthetic compounds that are chemical derivatives of the compound produced by microorganisms or synthetic compounds that act on very specific biochemical pathways necessary for the cell's survival.

"Antiseptic" means a chemical agent other than the "enhancers" described herein that kills pathogenic and non-pathogenic microorganisms. Preferred antiseptics exhibit at least 4 log reduction of both *P. aeruginosa* and *S. aureus* in 60 minutes from an initial inoculum of $1\text{-}3\times 10^7$ cfu/ml when tested in Mueller Hinton broth at 35° C. at a concentration of 0.25 wt % in a Rate of Kill assay using an appropriate neutralizer as described in *The Antimicrobial Activity in vitro of chlorhexidine, a mixture of isothiazolinones (Kathon CG) and cetyl trimethyl ammonium bromide (CTAB)*, G. Nicoletti, V. Boghossian, F. Gurevitch, R. Borland and P. Mogenroth, *Journal of Hospital Infection*, (1993), vol. 23, pp 87-111. Antiseptics generally interfere more broadly with the cellular metabolism and/or the cell envelope. Antiseptics may be small molecule or polymeric. Small molecule antiseptics generally have molecular weights less than about 350 g/mole. Polymeric antiseptics can be much higher in molecular weight.

"Enhancer" means a component that enhances the effectiveness of the antiseptic component such that when the composition less the antiseptic component and the composition less the enhancer component are used separately, they do not provide the same level of antimicrobial activity as the composition as a whole. For example, an enhancer component in the absence of the antiseptic component may not provide any appreciable antimicrobial activity. The enhancing effect can be with respect to the level of kill, the speed of kill, and/or the spectrum of microorganisms killed, and may not be seen for all microorganisms. In fact, an enhanced level of kill is most often seen in Gram-negative bacteria such as *Escherichia coli*. An enhancer may be a synergist such that when combined with the remainder of the composition, the composition as a whole displays an activity that is greater than the sum of the activity of the composition less the enhancer component and the composition less the antiseptic component.

"Mucous membranes," "mucosal membranes," and "mucosal tissue" are used interchangeably and refer to the surfaces of the nasal (including anterior nares, nasopharyngeal cavity, etc.), oral (e.g., mouth), outer ear, middle ear, vaginal cavities, and other similar tissues. Examples include mucosal membranes such as buccal, gingival, nasal, ocular, tracheal, bronchial, gastrointestinal, rectal, urethral, urethral, vaginal, cervical, and uterine mucosal membranes.

"Preservative" as used herein refers to antiseptics that are incorporated into a composition to prevent biological contamination and/or deterioration of a composition. These are generally present at levels of less than 0.50% by weight and often less than about 0.1% by weight.

"Affliction" means a condition to a body resulting from sickness, disease, injury, bacterial colonization, etc.

"Treat" or "treatment" means to improve the condition of a subject relative to the affliction, typically in terms of clinical symptoms of the condition.

"Decolonization" refers to a reduction in the number of microorganisms (e.g., bacteria and fungi) present in or on tissue that do not necessarily cause immediate clinical symptoms. Examples of decolonization include, but are not limited to, decolonization of the nasal cavity and wounds. Ordinarily fewer microorganisms are present in "colonized tissue" than in "infected tissue." When the tissue is completely decolonized the microorganisms have been "eradicated".

"Subject" and "patient" includes humans, sheep, horses, cattle, pigs, dogs, cats, rats, mice, or other mammal.

"Wound" refers to an injury to a subject which involves a break in the normal skin or mucosal tissue barrier exposing tissue below, which is caused by, for example, lacerations, surgery, burns, damage to underlying tissue such as pressure sores, poor circulation, and the like. Wounds are understood to include both acute and chronic wounds.

The terms "comprises" and variations thereof do not have a limiting meaning where these terms appear in the description and claims.

As used herein, "a," "an," "the," "at least one," and "one or more" are used interchangeably. The term "and/or" means one or all of the listed elements (e.g., preventing and/or treating an affliction means preventing, treating, or both treating and preventing further afflictions).

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The present invention provides antimicrobial (including, e.g., antiviral, antibacterial, and antifungal) compositions. These compositions include one or more antiseptics selected from the group consisting of halogenated phenols, diphenyl ethers, and bisphenols (including but not limited to p-chloro m-xylenol (PCMX) and triclosan Halogenated carbanilides, such as triclocarban (a 3,4,4' trichlorocarbanilide) and trifluoromethyl-4,4' dichlorocarbanilide, and salicylanilides may also be useful. The antiseptics are present in sufficient concentration (at least 0.20 wt-% and typically greater than 0.30 wt-% and most preferably greater than 0.50% by weight) which when applied to mammalian tissue for an adequate time, for an adequate frequency, and in an adequate dose are capable of decolonizing or eradicating microorganisms from the tissue. Certain compositions also include one or more surfactants, one or more hydrophilic compounds, and/or one or more hydrophobic compounds.

Such compositions preferably adhere well to bodily tissues (e.g., skin, mucosal tissue, and wounds) and thus are very effective topically. Importantly, the compositions, however, are not bioadhesive and thus will not bond tissue together. Thus, the present invention provides a wide variety of uses of the compositions. Particularly preferred methods involve topical application, particularly to mucosal tissues (i.e., mucous membranes including the anterior nares and other tissues of the upper respiratory tract), as well as skin (e.g., skin lesions) and wounds.

For certain applications in which broad spectrum antimicrobial activity is desired, compositions containing multiple antiseptics can be used. In other applications in which limited antimicrobial activity is desired, compositions containing an antiseptic with limited spectrum may be employed. For example, in certain situations it may be desirable to kill or inactivate only one type or a few types of microorganism as opposed to all the microorganisms present. For example, as shown in the Examples, compositions comprising PCMX in a petrolatum vehicle have activity against Methicillin Resistant *Staphylococcus Aureus* (MRSA) (Gram positive microorganisms), but only limited activity against *E. coli* (Gram negative microorganisms), and thus may be more useful in situations where it is desirable to kill mainly the Gram positive organisms, such as in nasal decolonization, treatment of impetigo and in other topical infections caused primarily by Gram positive organisms.

Compositions of the present invention can be used to provide effective topical antimicrobial activity and thereby treat and/or prevent a wide variety of afflictions. For example, they can be used in the treatment and/or prevention of afflictions that are caused, or aggravated by, microorganisms (e.g., Gram positive bacteria, Gram negative bacteria, fungi, protozoa, mycoplasma, yeast, viruses, and even lipid-enveloped viruses) on mammalian tissue, i.e., skin and/or mucous membranes, such as those in the nose (anterior nares, nasopharyngeal cavity, nasal cavities, etc.), outer ear, middle ear, mouth, rectum, vagina, or other similar tissue. Particularly relevant organisms that cause or aggravate such afflictions include *Staphylococcus* spp., *Streptococcus* spp., *Pseudomonas* spp., *Enterococcus* spp., and *Esherichia* spp., bacteria, as well as herpes virus, *Aspergillus* spp., *Fusarium* spp., and *Candida* spp and combinations thereof. Particularly virulent organisms include *Staphylococcus aureus* (including resistant strains such as Methicillin Resistant *Staphylococcus Aureus* (MRSA), *Staphylococcus epidermidis, Streptococcus pneumoniae, Enterococcus faecalis*, Vancomycin Resistant *Enterococcus* (VRE), *Pseudomonas auerginosa, Escherichia coli, Aspergillus niger, Aspergillus fumigatus, Aspergillus clavatus, Fusarium solani, Fusarium oxysporum, Fusarium chlamydosporum, Candida albicans, Candida glabrata*, and *Candida krusei*.

Compositions of the present invention can be used for the prevention and/or treatment of one or more microorganism-caused infections or other afflictions. In particular, compositions of the present invention can be used for preventing and/or treating one or more of the following: skin lesions, conditions of the skin such as impetigo, eczema, diaper rash in infants as well as incontinent adults, inflammation around ostomy devices, shingles, and bacterial infections in open wounds (e.g., cuts, scrapes, burns, lacerations, chronic wounds); necrotizing faciitis; infections of the outer ear; acute or chronic otitis media (middle ear infection) caused by bacterial, viral, or fungal contamination; fungal and bacterial infections of the vagina or rectum; vaginal yeast infections; bacterial rhinitis; ocular infections; cold sores; genital herpes; colonization by *Staphylococcus aureus* in the anterior nares (e.g., prior to surgery or hemodialysis); mucositis (i.e., inflammation as opposed to infection of a mucous membrane typically induced by non-invasive fungus); chronic sinusitis (e.g., that caused by bacterial or viral contamination); non-invasive fungus-induced rhinosinusitis; chronic colitis; Crohn's disease; burns; napkin rash; tinea pedis (i.e., athlete's foot); tinea curis (i.e., jock itch); tinea corporis (i.e., ringworm); candidiasis; strep throat, strep pharyngitis, and other Group A Streptococci infections; rosacea (often called adult acne); common cold; and respiratory afflictions (e.g., asthma). In sum, compositions of the present invention can be used for preventing and/or treating a wide variety of topical afflictions caused by microbial infection (e.g., yeast, viral, bacterial infections).

Compositions of the present invention can be used on a wide variety of surfaces. For example, they can be used on mammalian tissue (e.g., skin, mucosal tissue, chronic wounds, acute wounds, burns). They can also be delivered from swabs, cloth, sponges, foams and non-woven and paper products (e.g., paper towels and wipes), for example where they are used to deliver a significant portion of the antiseptic composition to the tissue. By "significant portion" it is meant that enough composition is applied and allowed to remain on the tissue when applied in a dose, at a frequency, and in an amount sufficient to reduce or eliminate the microorganisms on or in the tissue.

Thus, the present invention also provides various methods of use of compositions of the present invention. Various embodiments of the present invention include: a method of preventing an affliction caused, or aggravated by, a microorganism on mammalian tissue (i.e., skin and/or a mucous membrane); a method of decolonizing at least a portion of the nasal cavities, anterior nares, and/or nasopharynx of a subject of microorganisms; a method of eradicating microorganisms from at least a portion of the nasal cavities, anterior nares, and/or nasopharynx of a subject; a method of treating a middle ear infection in a subject (by introduction into the middle ear through the Eustachian tube, and/or the tympanic membrane by diffusion or direct injection); a method of treating chronic sinusitis in a subject (by treating at least a portion of the respiratory system, particularly the upper respiratory system, including the nasal cavities, anterior nares, and/or nasopharynx); a method of treating impetigo on the skin of a subject; a method of treating and/or preventing an infection on mammalian skin (skin, mucosal tissue, and/or wound); a method of treating a burn; a method of killing or inactivating microorganisms (e.g., killing bacteria and/or fungi, or inactivating viruses); a method for providing residual antimicrobial efficacy (e.g., antibacterial, antifungal, and/or antiviral efficacy) that results from leaving a residue or imparting a condition on a surface (such as skin, mucosal tissue, wound, and/or medical device that contacts such surfaces) that remains effective and provides significant antimicrobial activity. Not all of the antiseptics disclosed herein are useful for all of these conditions. Suitable indications for each antiseptic are discussed below.

It should be understood that compositions of the present invention can be used in situations in which there are no clinical indications of an affliction. For example, compositions of the present invention can be used in methods of decolonizing at least a portion of the nasal cavities (i.e., space behind the vestibule of the nose), anterior nares (i.e., the opening in the nose to the nasal cavities, also referred to as the external nares), and/or nasopharynx (i.e., the portion of the pharynx, i.e., throat, that lies above the point of food entry into the pharynx) of a subject of microorganisms. A suitable in-vivo model to test for the effectiveness of compositions to decolonize the anterior nares has been established and is described by K. Kiser et al., Infect and Immunity, 67(10), 5001-5006 (1999). Compositions of the present invention can also be used to decolonize microorganisms from wounds. Also disclosed in the example section is an in-vitro model that places microorganisms in contact with a static coating of the antimicrobial composition. This test method is suitable for comparing the potential efficacy of compositions of the present invention for most topical antiseptic applications, including nasal decolonization.

Decolonization methods using compositions of the present invention are particularly useful in immunocompromised patients (including oncology patients, diabetics, HIV patients, transplant patients an the like), particularly for fungi such as *Aspergillus* spp. and *Fusarium* spp.

In particular, compositions of the present invention can be used in chronic wounds to eliminate methicillin-resistant *Staphylococcus aureus* and vancomycin resistant *enterococcus*, which may or may not show clinical signs of infection such as inflammation, pus, exudate, etc. Also, it is of significance to note that certain compositions of the present invention can kill lipid-enveloped viruses, which can be very difficult to kill and can cause shingles (Herpes), chronic sinusitis, otitis media, and other local diseases.

Those of ordinary skill in the art will readily determine when a composition of the present invention provides antimicrobial activity using assay and bacterial screening methods well known in the art. One readily performed assay involves exposing selected known or readily available viable microorganism strains, such as *Enterococcus* spp., *Aspergillus* spp., *Escherichia* spp., *Staphylococcus* spp., *Streptococcus* spp., *Pseudomonas* spp., or *Salmonella* spp., to a test composition at a predetermined bacterial burden level in a culture media at an appropriate temperature. For the preferred compositions of the present invention, testing is most conveniently done using the Antimicrobial Efficacy Test described in the Examples Section. Briefly, the antimicrobial composition is coated onto a sterile surface and a bacterial suspension is distributed directly on the surface of the composition. After a sufficient contact time, the sample containing the exposed bacteria is collected, placed in neutralizing broth, a sample is taken and diluted, and plated out on agar. The plated sample is incubated at an appropriate temperature and humidity for forty-eight hours and the number of viable bacterial colonies growing on the plate is counted. Once colonies have been counted the reduction in the number of bacteria caused by the test composition is readily determined. Bacterial reduction is generally reported as $\log_{10}$ reduction determined by the difference between the $\log_{10}$ of the initial inoculum count and the $\log_{10}$ of the inoculum count after exposure. Preferred compositions of the present invention have an average of at least a 2 log reduction in test bacteria in 10 minutes, and preferably in 2.5 minutes.

Many of the preferred compositions were tested as described in the Examples Section for antimicrobial activity against MRSA (Gram positive, ATCC Number 16266) and *E. coli* (Gram negative, ATCC Number 11229). Preferred compositions of the present invention also exhibit very rapid antimicrobial activity. As shown in the Examples Section, preferred formulations are able to achieve an average log reduction of at least 4 log against at least one of these two organisms after a 10-minute exposure and preferably after a 2.5-minute exposure. More preferred compositions are able to achieve an average log reduction of at least 5 log and even more preferred at least 6 log against at least one of these two organisms after a 10-minute exposure and preferably after a 2.5-minute exposure.

For residual antimicrobial efficacy, compositions of the present invention preferably maintain an average log reduction of at least 1 log, more preferably at least 1.5 log, and even more preferably at least 2 log, for at least 1 hour, more preferably at least 3 hours, and even more preferably at least 24 hours after application to an affected site or after testing the composition on the forearm of a subject. To test this, a composition was applied to the forearm of a subject as a uniform wet coating in an amount of approximately 4 milligrams per square centimeter ($mg/cm^2$) to the forearm of a healthy subject and allowed to remain on the skin for typically a minimum of 10 minutes over an area of approximately 5×5 cm. The composition was gently washed with 23° C. normal saline (0.9% by weight sodium chloride). The saline washed site was exposed to a known quantity of bacteria in an inoculum of about $10^6$ bacteria/ml (typically *Staphylococcus epidermidis* or *E. coli*) for 30 minutes. The bacteria were recovered and treated with an effective neutralizer and incubated to quantify the bacteria remaining. Particularly preferred compositions retain at least 1 log reduction and preferably at least 2 log reduction of bacteria after a gentle rinse with 500 ml saline poured over the site by placing the saline container as close the site as possible so as to not have the saline fall onto the site.

Importantly, certain embodiments of the present invention have a very low potential for generating microbial resistance. For example, preferred compositions of the present invention have an increase in the ratio of final to initial MIC levels (i.e., minimum inhibitory concentration) of less than 16, more preferably less than 8, and even more preferably less than 4. Such an emergence of resistance assay should be carried out such that the microorganisms are subjected initially to sub MIC levels (e.g., ½ the MIC) of antiseptic and after 24 hours the microorganisms passed into broth containing twice the concentration of antiseptic. This is repeated for 8 days and each day microorganisms are removed to determine the new MIC. Thus, such low resistance forming compositions can be applied multiple times over one or more days to treat topical infections or to eradicate unwanted bacteria (such as nasal colonization of *Staphylococcus aureus*).

Preferred compositions of the present invention contain an effective amount of antimicrobial to rapidly kill or inactivate microorganisms on skin, skin lesions, and mucosal membranes. In certain embodiments, essentially all the microorganisms are eradicated or inactivated using one or more doses within five days, preferably within three days, more preferably two days, and most preferably within 24 hours using one or more doses.

Preferred compositions of the present invention have a generally low irritation level for skin, skin lesions, and mucosal membranes (including the anterior nares, nasal cavities, nasopharyngeal cavity and other portions of the upper respiratory tract). For example, certain preferred compositions of the present invention are no more irritating than BACTROBAN ointment (on skin) or BACTROBAN NASAL (in the anterior nares) products available from Glaxo Smith Kline.

Preferred compositions of the present invention are substantive for relatively long periods of time to ensure adequate efficacy. For example, certain compositions of the present invention remain at the site of application with antimicrobial activity for at least 1 hour, preferably at least 4 hours, and more preferably at least 8 hours. Substantivity can be determined by swabbing the site after a predetermined time and testing for the antimicrobial active by a suitable analytical technique such as gas chromatography (GC) or high performance liquid chromatography (HPLC).

Preferred compositions of the present invention are physically stable. As defined herein "physically stable" compositions are those that do not significantly change due to substantial precipitation, crystallization, phase separation, and the like, from their original condition during storage at 23° C. for at least 3 months, and preferably for at least 6 months. Particularly preferred compositions are completely physically stable if a 10-milliliter (10-ml) sample of the composition when placed in a 15-ml conical-shaped graduated plastic centrifuge tube (Corning) and centrifuged at 2275×g (e.g., at 3,000 revolutions per minute (rpm) for 10 minutes using a Labofuge B, model 2650 manufactured by Heraeus Sepatech GmbH, Osterode, West Germany) or similar centrifuge at a centrifugal force of 2275×g, has no visible phase separation in the bottom or top of the tube. Phase separation of less than 0.5 ml is also considered stable as long as there is no other sign of physical separation in the sample.

Preferred compositions of the present invention exhibit good chemical stability. This can be especially a concern with compounds that may hydrolyze or undergo heat and/or light degradation. The most preferred compositions retain an average of at least 97% of the antimicrobial component after aging for 4 weeks at 40° C. in a sealed container beyond the initial 5-day equilibration period at 23° C. The percent retention is understood to mean the weight percent of antimicrobial component retained. This is determined by comparing the amount remaining in a sample aged (i.e., aged beyond the initial 5-day equilibration period) in a sealed container that does not cause degradation, to the actual measured level in an identically prepared sample (preferably from the same batch) and allowed to sit at 23° C. for five days. The level of antimicrobial component is preferably determined using gas chromatography or high performance liquid chromatography.

Generally, the compositions of this invention may be in one of the following forms:

A hydrophobic ointment: The compositions are formulated with a hydrophobic base (e.g., petrolatum, thickened or gelled water insoluble oils and the like) and optionally having a minor amount of a water-soluble phase.

An oil in water emulsion: The compositions may be formulations in which the antiseptic is emulsified into an emulsion comprising a discrete phase of a hydrophobic component and a continuous aqueous phase comprising water and optionally one or more polar hydrophilic carrier as well as salts, surfactants, emulsifiers, or other components. These emulsions may comprise water-soluble or water swellable polymers as well as one or more emulsifiers that help to stabilize the emulsion. These emulsions generally have higher conductivity values as described in U.S. Ser. No. 09/966,511.

A water in oil emulsion: The compositions may be formulations in which the antiseptic is incorporated into an emulsion comprising a continuous phase of a hydrophobic component and an aqueous phase comprising water and optionally one or more polar hydrophilic carrier as well as salts or other components. These emulsions may comprise oil soluble or oil swellable polymers as well as one or more emulsifiers that help to stabilize the emulsion.

Thickened aqueous gels: These systems are comprised of an aqueous phase that has been thickened to achieve a viscosity in excess of 500 cps and preferably greater than 5000 cps. Most preferred systems have a viscosity in excess of 10,000 cps, more preferably greater than 25,000 cps and most preferably greater than 50,000 cps. The viscosity is determined using the Viscosity Test described herein. These systems comprise the antiseptics described here in and are thickened by suitable natural, modified natural, or synthetic polymers as described below. The thickened aqueous gels can also be thickened using suitable emulsifiers such as alkyl alcohols and polyethoxylated alkyl chain surfactants that effectively thicken the composition. Examples include the Polawax, Behenyl TMS, Crodaphos CES, Cosmowax, and Crothix systems from Croda Inc.

Hydrophilic gels: These are systems in which the continuous phase is comprised of at least one water soluble hydrophilic component other than water. The formulations may optionally also contain water up to about 20% by weight. Higher concentrations may be suitable in some compositions. Suitable hydrophilic components include one or more glycols (such as glycerin, propylene glycol, butylenes glycol, etc.), polyethylene glycols (PEG), random or block copolymers of ethylene oxide, propylene oxide, and/or butylenes oxide, polyalkoxylated surfactants having one or more hydrophobic moieties per molecule, silicone copolyols, as well as combinations thereof. One skilled in the art will recognize that the level of ethoxylation must be sufficient to render the hydrophilic component water-soluble or water dispersible at 23° C. In most embodiments, the water content is less than 10 wt-% and more preferably less than about 5% by weight of the composition.

In most embodiments, the compositions have a viscosity of at least 20 cps, preferably greater than 100 cps, more preferably greater than 1000 cps, even more preferably greater than 10,000 cps and most preferably greater than 25,000 cps when measured by the Viscosity Test described herein. Higher viscosities are preferred to reduce migration as well as to provide substantivity (resistance to removal by fluids) to ensure long-term antimicrobial activity. Most preferred compositions have viscosities in excess of 50,000 cps and most preferably in excess of 100,000 cps at 23-25° C. when measured by the Viscosity Test. Most preferred compositions meet these viscosity values even after heating to 32° C., 35° C. or as high as 37° C. to ensure when in contact with mammalian tissue the compositions remain substantive.

Antiseptic Component

The antiseptic component is that component of the composition that provides at least part of the antimicrobial activity. That is, the antiseptic component has at least some antimicrobial activity for at least one microorganism. It is generally considered the main active component of the compositions of the present invention. The antiseptic component includes an effective amount of one or more antiseptics selected from the group consisting of phenols, halogenated phenols and bisphenols, anilides such as halogenated carbanilides and salicylanilides, and compatible combinations thereof.

Phenolic antiseptics suitable for use in the antimicrobial compositions include, but are not limited to, diphenyl ethers, such as the polyhalogenated hydroxy diphenyl ethers, more specifically those containing multiple halogen substituents; simple phenolics, such as phenol, cresol, o-phenylphenol, 4-hexylresorcinol; and the halogenated phenolics, such as p-chlorometa-xylenol, dichlorometa-xylenol, o-benzyl p-chlorophenol and p-isoamylphenol; bisphenolics, e.g., 2,2'-methylene bis (3,4,6-trichlorophenol), 2,2'-methylene bis (4,6-dichlorophenol), 2,2'-methylene bis (4-chlorophenol), 2,2'-thio bis (4,6-dichlorophenol); and anilides, e.g., salicylanilide, monohalogenated salicylanilide, and polyhalogenated salicylanilide. The following classes are used in most embodiments:

A. Diphenyl ethers such as polyhalogenated hydroxyl diphenyl ethers, more specifically those containing multiple halogen substituents, such as triclosan (2',4,4'-trichloro-2-hydroxy-diphenyl ether or 3-chloro-2-(2,4 dichlorophenoxy)phenol) and the like. These compounds can be represented by the following chemical structure:

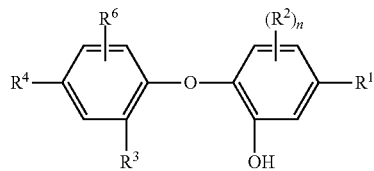

wherein $R^1$ and $R^3$ can be chlorine, bromine, or hydrogen, $R^2$ is chlorine or bromine; $R^4$ can be chlorine, bromine, an alkyl having 1 to 3 carbon atoms, $CH_3O$—, $CN$—, and $NH_2$—, $R^6$ can be hydrogen, chlorine, bromine, methyl, trichloromethyl, $CH_3O$—, $CN$—, and $NH_2$—; and n is 1 or 2.

B. Phenolics such as mono- and poly-Alkyl and Aromatic Halophenols (e.g., methyl-p-Chlorophenol, n-Butyl-p-Chlorophenol, O-Chlorophenol, o-Benzyl-p-Chlorophenol, o-Phenylethyl-m-methyl-p-Chlorophenol, 6-iso-Propyl-2-ethyl-3-methyl-p-Chlorophenol, methyl-p-Bromophenol, tert-Amyl-o-Bromophenol, 3,4,5,6-terabromo-2-methylphenol. A preferred antiseptic of this class is p-chloro-m-xylenol (PCMX).

C. Resorcinol and its derivatives such as Methyl-Resorcinol, Ethyl-Resorcinol, n-Propyl-Resorcinol, n-Butyl-Resorcinol, n-Amyl-Resorcinol, n-Hexyl-Resorcinol, n-Heptyl-Resorcinol, n-Octyl-Resorcinol, n-Nonyl-Resorcinol, Phenyl-Resorcinol, Benzyl-Resorcinol, Phenylethyl-Resorcinol, Phenylpropyl-Resorcinol, p-Chlorobenzyl-Resorcinol, 5-Chloro-2,4-Dihydroxydiphenyl Methane, 4'-Chloro-2,4-Dihydroxydiphenyl Methane, 5-Bromo-2,4-Dihydroxydiphenyl Methane, and 4'-Bromo-2,4-Dihydroxydiphenyl Methane.

D. Bisphenolics such as 2,2'-methylene bis(4-chlorophenol), 2,2'-methylene bis(3,4,6-trichlorophenol), 2,2'-methylene bis(4-chloro-6-bromophenol), bis(2-hydroxy-3,5-dichlorophenyl) sulfide, and bis(2-hydroxy-5-chlorobenzyl) sulfide.

E. Anilides, including salicylanilides and carbanilides such as those discussed in *Disinfection, Sterilization, and Preservation,* $2^{nd}$ Ed. Edited by Seymour S. Block, Chapter 14, Lea & Febiger, Philiadelphia Pa., 1977; and halogenated carbanilide compounds as described in U.S. Pat. No. 2,818,390. Particularly preferred carbanilide compounds are 3,4,4'-trichlorocarbanilide (triclocarban); 3,4',5-tribromosalicylanilide; 4,4'-dichloro-3'-(trifluoromethyl)carbanilide. Other anilides may be useful including but not limited to salicylanilide, monohalogenated salicylanilide, and polyhalogenated salicylanilide such as those disclosed in U.S. Pat. Nos. 4,010,252 and 4,894,220.

These compounds may be relatively water insoluble and thus it is preferred to formulate these compounds in the presence of a hydrophobic component and/or an emulsifier/surfactant, in an emulsion (water-in-oil or oil-in-water), or in a hydrophilic vehicle. These compounds are typically added to the formulations in amounts of 0.5% by weight, and preferably 1% by weight. In most embodiments, the compounds are added in amounts of no greater than 8 wt %, more preferably no greater than 6 wt %.

The most preferred compositions are formulated free of polyethylene glycol greater than a MW of about 1500 daltons, and more preferably greater than 600 daltons, which may reduce the activity. The most preferred compositions are those based on hydrophobic vehicles such as mineral oil or petrolatum, which may optionally contain a hydrophilic component and water in oil emulsions. The pH of aqueous compositions (or the aqueous phase of these compositions) formulated with these antiseptics typically range from 3-9 and most preferably from 3.5-7.

The compositions of the present invention include one or more antiseptics at a suitable level to produce the desired result. Such compositions preferably include a total amount of antiseptic of at least 0.2 percent by weight (wt-%), more preferably at least 0.25 wt-%, even more preferably at least 0.35 wt-%, even more preferably at least 0.5 wt-%, and even more preferably at least 1, at least 2, or even at least 3 wt-%, based on the total weight of the "ready to use" or "as used" composition. In a preferred embodiment, the antiseptic(s) are present in a total amount of no greater than 20 wt-%, more preferably no greater than 15 wt-%, even more preferably no greater than 10 wt-%, and even more preferably no greater than 6 wt-%, based on the "ready to use" or "as used" composition. Certain compositions may be higher in concentration if they are intended to be diluted prior to use.

The antiseptics of this invention may be used alone or in combination in order to effectively kill microorganisms on tissue. Certain combinations of antiseptics may be particularly useful while others may result in unstable formulations or inactivation of the antimicrobial activity. On the other hand, other antiseptic combinations may produce an enhancement or synergistic effect.

The antiseptics of this invention may be used alone, in combination, or with other antiseptics in order to effectively kill microorganisms on tissue. Additional antiseptics for use with those described herein include peroxides, C6-C14 alkyl carboxylic acids and alkyl ester carboxylic acids, antimicrobial natural oils, and compatible combinations thereof as provided in Applicants' copending application entitled "Antiseptic Compositions and Methods of Use," U.S. Ser. No. 10/936,133, filed on the same date; chlorhexidine and its salts such as digluconate, diacetate, dimethosulfate, and dilactate salts, polymeric quaternary ammonium compounds such as polyhexamethylenebiguanide, silver and various silver complexes, small molecule quaternary ammonium compounds such as benzalkonium chloride and alkyl substituted derivatives, di-long chain alkyl (C8-C18) quaternary ammonium compounds, cetylpyridinium halides and their derivatives, benzethonium chloride and its alkyl substituted derivatives, octenidine, and combinations thereof, provided in Applicants' copending application entitled "Cationic Antiseptic Compositions and Methods of Use," U.S. Ser. No. 10/936,135, filed on the same date.

Certain combinations of antiseptics may be particularly useful while others may result in unstable formulations or inactivation of the antimicrobial activity. For example, combination of cationic antiseptics such as biguanides and bis-biguanides, polymeric quaternary ammonium compounds, quaternary ammonium compounds, and silver may be incompatible with alkyl carboxylic acids. On the other hand, other antiseptic combinations may produce a synergistic or enhancing effect. For example, C6 and higher fatty acids may enhance the activity of peroxides as well as the fatty acid monoglycerides antiseptics described below.

In certain embodiments, the antiseptics of this invention may optionally be combined with an effective amount of an antimicrobial lipid antiseptic comprising a (C7-C12)saturated fatty acid ester of a polyhydric alcohol, a (C12-C22) unsaturated fatty acid ester of a polyhydric alcohol, a (C7-C12)saturated fatty ether of a polyhydric alcohol, a (C12-C22)unsaturated fatty ether of a polyhydric alcohol, an alkoxylated derivative thereof, or combinations thereof, wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers, diethers, or combinations thereof. Useful antiseptics of this class are further described in applicants' copending application "Antimicrobial Compositions and Methods of Use," U.S. Ser. No. 10/659,571, filed on Sep. 9, 2003. As used herein the term "fatty" refers to alkyl and alkylene hydrocarbon chains of odd or even number of carbon atoms from C6-C18.

To achieve rapid antimicrobial activity, formulations may incorporate one or more antiseptics in the composition approaching or preferably exceeding the solubility limit in the hydrophobic phase. While not intended to be bound by theory, it appears that antiseptics that preferably partition into the hydrophobic component are not readily available to kill microorganisms, which are almost always in or associated with an aqueous phase. In most compositions the antiseptic is preferably incorporated in at least 60%, preferably at least 75%, more preferably at least 100% and most preferably at least 120% of the solubility limit of the hydrophobic component at 23° C. This is conveniently determined by making the formulation without the antiseptic, separating the phases (e.g., by centrifugation or other suitable separation technique) and determining the solubility limit by addition of progressively greater levels of the antiseptic until precipitation occurs. Alternatively, if the formulation is known one can take the components which will form the lipophilic phase, mix them in the proper proportions, and determine the solubility limit. One skilled in the art will realize that creation of supersaturated solutions must be avoided for an accurate determination. For example, we have found that compositions using hydrophobic vehicles that contain triclosan are dramatically more active above the solubility limit.

Enhancer Component

Compositions of the present invention may optionally include an enhancer to enhance the antimicrobial activity. The activity enhancement may be especially useful against Gram-negative bacteria, such as E. coli and Psuedomonas sp. The enhancer chosen preferably effects the cell envelope of the bacteria. While not bound by theory, it is presently believed that the enhancer functions by allowing the antiseptic to more easily enter the cell cytoplasm and/or by facilitating disruption of the cell envelope. The enhancer component may include an alpha-hydroxy acid, a beta-hydroxy acid, other carboxylic acids, a (C1-C4)alkyl carboxylic acid, a (C6-C12) aryl carboxylic acid, a (C6-C12)aralkyl carboxylic acid, a (C6-C12)alkaryl carboxylic acid, a chelator, a phenolic compound (such as certain antioxidants and parabens), a (C1-C10)monohydroxy alcohol, or a glycol ether (i.e., ether glycol). Various combinations of enhancers can be used if desired.

The alpha-hydroxy acid, beta-hydroxy acid, and other carboxylic acid enhancers are preferably present in their protonated, free acid form. It is not necessary for all of the acidic enhancers to be present in the free acid form, however, the preferred concentrations listed below refer to the amount present in the free acid form. Additional, non-alpha hydroxy acid, betahydroxy acid or other carboxylic acid enhancers, may be added in order to acidify the formulation or buffer it at a pH to maintain antimicrobial activity. Furthermore, the chelator enhancers that include carboxylic acid groups are preferably present with at least one, and more preferably at least two, carboxylic acid groups in their free acid form. The concentrations given below assume this to be the case. Chelator enhancers may also comprise phosphate or phosphonic acid groups. If precipitation occurs due to interaction with other composition components, alternative enhancers should be considered. The anionic enhancers may be particularly useful with the halogenated phenols and bisphenols.

One or more enhancers may be used in the compositions of the present invention at a suitable level to produce the desired result. In a preferred embodiment, they are present in a total amount greater than 0.01 wt-%, preferably in an amount greater than 0.1 wt %, more preferably in an amount greater than 0.2 wt %, even more preferably in an amount greater than 0.25 wt % and most preferably in an amount greater than about 0.4 wt % based on the total weight of the ready to use composition. In a preferred embodiment, they are present in a total amount of no greater than 20 wt-%, based on the total weight of the ready to use composition. Such concentrations typically apply to alpha-hydroxy acids, beta-hydroxy acids, other carboxylic acids, chelating agents, phenolics, ether glycols, and (C5-C10)monohydroxy alcohols. Generally, higher concentrations are needed for (C1-C4)monohydroxy alcohols, as described in greater detail below.

The alpha-hydroxy acid, beta-hydroxy acid, and other carboxylic acid enhancers, as well as chelators that include carboxylic acid groups, are preferably present in a concentration of no greater than 100 milliMoles per 100 grams of formulated composition. In most embodiments, alpha-hydroxy acid, beta-hydroxy acid, and other carboxylic acid enhancers, as well as chelators that include carboxylic acid groups, are preferably present in a concentration of no greater than 75 milliMoles per 100 grams, more preferably no greater than 50 milliMoles per 100 grams, and most preferably no greater than 25 milliMoles per 100 grams of formulated composition.

The total concentration of the enhancer component relative to the total concentration of the antiseptic component is preferably within a range of 10:1 to 1:300, and more preferably 5:1 to 1:10, on a weight basis.

An additional consideration when using an enhancer is the solubility and physical stability in the compositions. Many of the enhancers discussed herein are insoluble in preferred hydrophobic components such as mineral oil or petrolatum. It has been found that the addition of a minor amount (typically less than 30 wt-%, preferably less than 20 wt-%, and more preferably less than 12 wt-%) of a hydrophilic component not only helps dissolve and physically stabilize the composition but improves the antimicrobial activity as well. These hydrophilic components are described below. Alternatively, the enhancer may be present in excess of the solubility limit provided that the composition is physically stable. This may be achieved by utilizing a sufficiently viscous composition that stratification (e.g., settling or creaming) of the antiseptic does not appreciably occur.

Alpha-hydroxy Acids. An alpha-hydroxy acid is typically a compound represented by the formula:

$$R^5(CR^6OH)_n COOH$$

wherein: $R^5$ and $R^6$ are each independently H or a (C1-C8) alkyl group (straight, branched, or cyclic), a (C6-C12)aryl, or a (C6-C12)aralkyl or alkaryl group (wherein the alkyl group is straight, branched, or cyclic), wherein $R^5$ and $R^6$ may be optionally substituted with one or more carboxylic acid groups; and n=1-3, preferably, n=1-2.

Exemplary alpha-hydroxy acids include, but are not limited to, lactic acid, malic acid, citric acid, 2-hydroxybutanoic acid, 3-hydroxybutanoic acid, mandelic acid, gluconic acid, glycolic acid, tartaric acid, alpha-hydroxyethanoic acid, ascorbic acid, alpha-hydroxyoctanoic acid, hydroxycaprylic acid, and salicylic acid as well as derivatives thereof (e.g., compounds substituted with hydroxyls, phenyl groups, hydroxyphenyl groups, alkyl groups, halogens, as well as combinations thereof). Preferred alpha-hydroxy acids include lactic acid, malic acid, and mandelic acid. These acids may be in D, L, or DL form and may be present as free acid, lactone, or partial salts thereof. All such forms are encompassed by the term "acid." Preferably, the acids are present in the free acid form. In certain preferred embodiments, the alpha-hydroxy acids useful in the compositions of the present invention are selected from the group consisting of lactic acid, mandelic acid, and malic acid, and mixtures thereof. Other suitable alpha-hydroxy acids are described in U.S. Pat. No. 5,665,776 (Yu).

One or more alpha-hydroxy acids may be used in the compositions of the present invention at a suitable level to produce the desired result. In a preferred embodiment, they are present in a total amount of at least 0.25 wt-%, more preferably, at least 0.5 wt-%, and even more preferably, at least 1 wt-%, based on the total weight of the ready to use composition. In a preferred embodiment, they are present in a total amount of no greater than 10 wt-%, more preferably no greater than 5 wt-%, and even more preferably, no greater than 3 wt-%, based on the total weight of the ready to use composition. Higher concentrations may become irritating.

The ratio of alpha-hydroxy acid enhancer to total antiseptic component is preferably at most 10:1, more preferably at most 5:1, and even more preferably at most 1:1. The ratio of alpha-hydroxy acid enhancer to total antiseptic component is preferably at least 1:20, more preferably at least 1:12, and even more preferably at least 1:5. Preferably the ratio of alpha-hydroxy acid enhancer to total antiseptic component is within a range of 1:12 to 1:1.

Beta-hydroxy Acids. A beta-hydroxy acid is typically a compound represented by the formula:

$$R^7(CR^8OH)_n(CHR^9)_m COOH \text{ or}$$

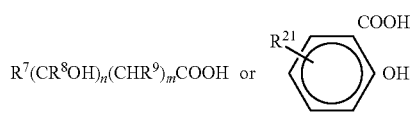

wherein: $R^7$, $R^8$, and $R^9$ are each independently H or a (C1-C8)alkyl group (saturated straight, branched, or cyclic group), a (C6-C12)aryl, or a (C6-C12)aralkyl or alkaryl group (wherein the alkyl group is straight, branched, or cyclic), wherein $R^7$ and $R^8$ may be optionally substituted with one or more carboxylic acid groups; m=0 or 1; n=1-3 (preferably, n=1-2); and $R^{21}$ is H, (C1-C4)alkyl or a halogen.

Exemplary beta-hydroxy acids include, but are not limited to, salicylic acid, beta-hydroxybutanoic acid, tropic acid, and trethocanic acid. In certain preferred embodiments, the beta-hydroxy acids useful in the compositions of the present invention are selected from the group consisting of beta-hydroxybutanoic acid, and mixtures thereof. Other suitable beta-hydroxy acids are described in U.S. Pat. No. 5,665,776 (Yu).

One or more beta-hydroxy acids may be used in the compositions of the present invention at a suitable level to produce the desired result. In a preferred embodiment, they are present in a total amount of at least 0.1 wt-%, more preferably at least 0.25 wt-%, and even more preferably at least 0.5 wt-%, based on the total weight of the ready to use composition. In a preferred embodiment, they are present in a total amount of no greater than 10 wt-%, more preferably no greater than 5 wt-%, and even more preferably no greater than 3 wt-%, based on the total weight of the ready to use composition. Higher concentrations may become irritating.

The ratio of beta-hydroxy acid enhancer to total antiseptic component is preferably at most 10:1, more preferably at most 5:1, and even more preferably at most 1:1. The ratio of beta-hydroxy acid enhancer to total antiseptic component is preferably at least 1:20, more preferably at least 1:15, and even more preferably at least 1:10. Preferably the ratio of beta-hydroxy acid enhancer to total antiseptic component is within a range of 1:15 to 1:1.

In systems with low concentrations of water, or that are essentially free of water, esterification may be the principle route of loss of the enhancer by reaction with, for example, the antiseptic or a hydroxyl functional hydrophilic component. Thus, certain alpha-hydroxy acids (AHA) and beta-hydroxy acids (BHA) are particularly preferred since these are believed to be less likely to esterify by reaction of the hydroxyl group of the AHA or BHA. For example, salicylic acid may be particularly preferred in certain formulations since the phenolic hydroxyl group is a much more acidic alcohol and thus much less likely to react. Other particularly preferred compounds in anhydrous or low-water content formulations include lactic, mandelic, malic, citric, tartaric, and glycolic acid. Benzoic acid and substituted benzoic acids that do not comprise a hydroxyl group, while not an hydroxyl acid, are also preferred due to a reduced tendency to form ester groups.

Other Carboxylic Acids. Carboxylic acids other than alpha- and beta-carboxylic acids are suitable for use in the enhancer component. These include alkyl, aryl, aralkyl, or alkaryl carboxylic acids typically having equal to or less than 12 carbon atoms and preferably less than about 8 carbon atoms. A preferred class of these can be represented by the following formula:

$$R^{10}(CR^{11}_2)_n COOH$$

wherein: $R^{10}$ and $R^{11}$ are each independently H or a (C1-C4) alkyl group (which can be a straight, branched, or cyclic group), a (C6-C12)aryl group, a (C6-C12) group containing both aryl groups and alkyl groups (which can be a straight, branched, or cyclic group), wherein $R^{10}$ and $R^{11}$ may be optionally substituted with one or more carboxylic acid groups; and n=0-3, preferably, n=0-2. Preferably, the carboxylic acid is a (C1-C4)alkyl carboxylic acid, a (C6-C12) aralkyl carboxylic acid, or a (C6-C12)alkaryl carboxylic acid.

Exemplary acids include, but are not limited to, acetic acid, propionic acid, benzoic acid, benzylic acid, nonylbenzoic acid, and the like. Particularly preferred is benzoic acid.

One or more carboxylic acids may be used in the compositions of the present invention at a suitable level to produce the desired result. In a preferred embodiment, they are present in a total amount of at least 0.1 wt-%, more preferably at least 0.25 wt-%, even more preferably at least 0.5 wt-%, and most preferably at least 1 wt-%, based on the ready to use concentration composition. In a preferred embodiment, they are present in a total amount of no greater than 10 wt-%, more preferably no greater than 5 wt-%, and even more preferably no greater than 3 wt-%, based on the ready to use composition.

The ratio of the total concentration of carboxylic acids (other than alpha- or beta-hydroxy acids) to the total concentration of the antiseptic component is preferably within a range of 10:1 to 1:100, and more preferably 2:1 to 1:10, on a weight basis.

Chelators. A chelating agent (i.e., chelator) is typically an organic compound capable of multiple coordination sites with a metal ion in solution. Typically these chelating agents are polyanionic compounds and coordinate best with polyvalent metal ions. Exemplary chelating agents include, but are not limited to, ethylene diamine tetraacetic acid (EDTA) and salts thereof (e.g., $EDTA(Na)_2$, $EDTA(Na)_4$, $EDTA(Ca)$, $EDTA(K)_2$), sodium acid pyrophosphate, acidic sodium hexametaphosphate, adipic acid, succinic acid, polyphosphoric acid, sodium acid pyrophosphate, sodium hexametaphosphate, acidified sodium hexametaphosphate, nitrilotris(methylenephosphonic acid), diethylenetriaminepentaacetic acid, 1-hydroxyethylene, 1,1-diphosphonic acid, and diethylenetriaminepenta-(methylenephosphonic acid). Certain carboxylic acids, particularly the alpha-hydroxy acids and beta-hydroxy acids, can also function as chelators, e.g., malic acid and tartaric acid. Also included as chelators are compounds highly specific toward ferrous or ferric ions such as siderophores, lactoferrin, and transferrin.

In certain preferred embodiments, the chelating agents useful in the compositions of the present invention include those selected from the group consisting of ethylenediaminetetraacetic acid and salts thereof, succinic acid, and mixtures thereof. Preferably, either the free acid or the mono- or di-salt form of EDTA is used.

One or more chelating agents may be used in the compositions of the present invention at a suitable level to produce the desired result. In a preferred embodiment, they are present in a total amount of at least 0.01 wt-%, more preferably at least 0.05 wt-%, even more preferably at least 0.1 wt-%, and even more preferably at least 0.25 wt-%, based on the weight of the ready to use composition. Alternatively, in a preferred embodiment the chelators are present in a total amount of at least 300 uM (micromolar), preferably at least 500 uM, more preferably at least 1000 uM and most preferably at least 200 uM based on the total weight/volume of composition even if it may comprise multiple phases. In a preferred embodiment, they are present in a total amount of no greater than 10 wt-%, more preferably no greater than 5 wt-%, and even more preferably no greater than 1 wt-%, based on the weight of the ready to use composition.

The ratio of the total concentration of chelating agents (other than alpha- or beta-hydroxy acids) to the total concentration of the antiseptic component is preferably within a range of 10:1 to 1:100, and more preferably 1:1 to 1:10, on a weight basis.

Phenolic Derivative Compounds. A phenolic derivative compound enhancer is typically a compound having the following general structure:

wherein: m is 0 to 3 (especially 1 to 3), n is 1 to 3 (especially 1 to 2), each $R^{12}$ independently is alkyl or alkenyl of up to 12 carbon atoms (especially up to 8 carbon atoms) optionally substituted with O in or on the chain (e.g., as a carbonyl group) or OH on the chain, and each $R^{13}$ independently is H or alkyl or alkenyl of up to 8 carbon atoms (especially up to 6 carbon atoms) optionally substituted with O in or on the chain (e.g., as a carbonyl group) or OH on the chain, but where $R^{13}$ is H, n preferably is 1 or 2.

Examples of phenolic derivative enhancers include, but are not limited to, butylated hydroxy anisole, e.g., 3(2)-tert-butyl-4-methoxyphenol (BHA), 2,6-di-tert-butyl-4-methylphenol (BHT), 3,5-di-tert-butyl-4-hydroxybenzylphenol, 2,6-di-tert-4-hexylphenol, 2,6-di-tert-4-octylphenol, 2,6-di-tert-4-decylphenol, 2,6-di-tert-butyl-4-ethylphenol, 2,6-di-tert-4-butylphenol, 2,5-di-tert-butylphenol, 3,5-di-tert-butylphenol, 4,6-di-tert-butyl-resorcinol, methyl paraben (4-hydroxybenzoic acid methyl ester), ethyl paraben, propyl paraben, butyl paraben, 2-phenoxyethanol, as well as combinations thereof. A preferred group of the phenolic derivative compounds is the phenol species having the general structure shown above where $R^{13}$=H and where $R^{12}$ is alkyl or alkenyl of up to 8 carbon atoms, and n is 0, 1, 2, or 3, especially where at least one $R^{12}$ is butyl and particularly tert-butyl, and especially the non-toxic members thereof. Some of the preferred phenolic derivative enhancers are BHA, BHT, methyl paraben, ethyl paraben, propyl paraben, and butyl paraben as well as combinations of these.

One or more phenolic derivative compounds may be used in the compositions of the present invention at a suitable level to produce the desired result. The concentrations of the phenolic compounds in medical-grade compositions may vary widely, but as little as 0.001 wt-%, based on the total weight of the composition, can be effective when the above-described esters are present within the above-noted ranges. In a preferred embodiment, they are present in a total amount of at least 0.01 wt-%, more preferably at least 0.10 wt-%, and even more preferably at least 0.25 wt-%, based on the ready to use composition. In a preferred embodiment, they are present in a total amount of no greater than 8 wt-%, more preferably no greater than 4 wt-%, and even more preferably no greater than 2 wt-%, based on the ready to use composition.

It is preferred that the ratio of the total phenolic concentration to the total concentration of the antiseptic component be within a range of 10:1 to 1:300, and more preferably within a range of 1:1 to 1:10, on a weight basis.

The above-noted concentrations of the phenolic derivative enhancers are normally observed unless concentrated formulations for subsequent dilution are intended. On the other hand, the minimum concentration of the phenolics and the antiseptic components to provide an antimicrobial effect will vary with the particular application.

Monohydroxy Alcohols. An additional enhancer is a monohydroxy alcohol having 1-10 carbon atoms. This includes the lower (i.e., C1-C4) monohydroxy alcohols (e.g., methanol, ethanol, isopropanol, and butanol) as well as longer chain (i.e., C5-C10) monohydroxy alcohols (e.g., iosbutanol, t-butanol, octanol, and decanol). In certain preferred embodiments, the alcohols useful in the compositions of the present invention are selected from the group consisting of methanol, ethanol, isopropyl alcohol, and mixtures thereof.

One or more alcohols may be used in the compositions of the present invention at a suitable level to produce the desired result. In a one embodiment, the short chain (i.e., C1-C4) alcohols are present in a total amount of at least 5 wt-%, even more preferably at least 10 wt-%, even more preferably at least 15 wt-%, and even more preferably at least 20 wt-%, based on the total weight of the ready to use composition. In a preferred embodiment, the (C1-C4)alcohols are present in a total amount of no greater than 50 wt-%, more preferably no greater than 40 wt-%, and even more preferably no greater than 30 wt-%, based on the total weight of the ready to use composition.

For certain applications, lower alcohols may not be preferred due to the strong odor and potential for stinging and irritation. This can occur especially at higher levels. In applications where stinging or burning is a concern, the concentration of (C1-C4)alcohols is preferably less than 20 wt-%, more preferably less than about 15 wt-%.

In a preferred embodiment longer chain (i.e., C5-C10) alcohols are present in a total amount of at least 0.1 wt-%, more preferably at least 0.25 wt-%, and even more preferably at least 0.5 wt-%, and most preferably at least 1.0 wt-%, based on the ready to use composition. In a preferred embodiment, the (C6-C10)alcohols are present in a total amount of no greater than 10 wt-%, more preferably no greater than 5 wt-%, and even more preferably no greater than 2 wt-%, based on the total weight of the ready to use composition.

Ether glycols. An additional enhancer is an ether glycol. Exemplary ether glycols include those of the formula:

R'—O—(CH$_2$CHR"O)$_n$(CH$_2$CHR"O)H wherein R'=H, a (C1-C8)alkyl, or a (C6-C12)aralkyl or alkaryl; and each R" is independently =H, methyl, or ethyl; and n=0-5, preferably 1-3. Examples include 2-phenoxyethanol, dipropylene glycol, triethylene glycol, the line of products available under the trade designation DOWANOL DB (di(ethylene glycol) butyl ether), DOWANOL DPM (di(propylene glycol)monomethyl ether), and DOWANOL TPNB (tri(propylene glycol) monobutyl ether), as well as many others available from Dow Chemical, Midland Mich.

One or more ether glycols may be used in the compositions of the present invention at a suitable level to produce the desired result. In a preferred embodiment, they are present in a total amount of at least 0.01 wt-%, based on the total weight of the ready to use composition. In a preferred embodiment, they are present in a total amount of no greater than 20 wt-%, based on the total weight of the ready to use composition.

Surfactants

Compositions of the present invention can include one or more surfactants to emulsify the composition and to help the composition wet the surface and/or to aid in contacting the microorganisms. As used herein the term "surfactant" means an amphiphile (a molecule possessing both polar and nonpolar regions which are covalently bound) capable of reducing the surface tension of water and/or the interfacial tension between water and an immiscible liquid. The term is meant to include soaps, detergents, emulsifiers, surface-active agents and the like. The surfactant can be cationic, anionic, nonionic, or amphoteric. This includes a wide variety of conventional surfactants; however, certain ethoxylated surfactants may reduce or eliminate the antimicrobial efficacy of the antiseptic component. The exact mechanism of this is not known and not all ethoxylated surfactants display this negative effect.

For example, poloxamer (polyethylene oxide/polypropylene oxide) surfactants have been shown to be compatible with some antiseptic components, but ethoxylated sorbitan fatty acid esters such as those sold under the trade name TWEEN by ICI have not been compatible and may even be useful in neutralizing the antiseptic in microbiological assays. Furthermore, certain anionic surfactants may not be compatible with the cationic antiseptics optionally present in the compositions of this invention. It should be noted that these are broad generalizations and the activity could be formulation dependent. One skilled in the art can easily determine compatibility of a surfactant by making the formulation and testing for antimicrobial activity as described in the Examples Section. Combinations of various surfactants can be used if desired.

It should be noted that certain antiseptics are amphiphiles and may be surface active. For example, the fatty acid antiseptics described herein are surface active. For those compositions that include both an amphiphilic antiseptic and a surfactant, the surfactant is a component separate from the amphiphilic antiseptic.

Preferred surfactants are those that have an HLB (i.e., hydrophile to lipophile balance) of at least 4 and more preferably at least 8. Even more preferred surfactants have an HLB of at least 12. Most preferred surfactants have an HLB of at least 15.

Examples of the various classes of surfactants are described below. In certain preferred embodiments, the surfactants useful in the compositions of the present invention are selected from the group consisting of sulfonates, sulfates, phosphonates, phosphates, poloxamer (polyethylene oxide/polypropylene oxide block copolymers), cationic surfactants, and mixtures thereof. In certain more preferred embodiments incorporating non-ionic or anionic antiseptics, the surfactants useful in the compositions of the present invention are selected from the group consisting of sulfonates, sulfates, phosphates, and mixtures thereof. Cationic, amphoteric, and non-ionic surfactants and in particular the ethylene oxide/propylene oxide surfactants such as poloxamers are particularly preferred for use if optional cationic components are present (e.g., an optional cationic antiseptic such as those described in co-pending patent application entitled "Cationic Antiseptic Compositions and Methods of Use," U.S. Ser. No. 10/936,135.

One or more surfactants may be used in the compositions of the present invention at a suitable level to produce the desired result. In many instances, the compositions of the present invention are intended to be left on tissue in the desired application. In a preferred embodiment, they are present in a total amount of at least 0.01 wt-%, preferably 0.1 wt %, more preferably at least 0.5 wt-%, and even more preferably at least 1.0 wt-%, based on the total weight of the ready to use composition. For those surfactants that can be irritating to tissue, the surfactants are preferably present in low concentrations, i.e., present in a total amount of no greater than 10 wt, more preferably no greater than 5 wt-%, and even more preferably no greater than 3 wt-%, based on the total weight of the ready to use composition. The ratio of the total concentration of surfactant to the total concentration of the antiseptic is preferably within a range of 5:1 to 1:100, more preferably 3:1 to 1:10, and most preferably 2:1 to 1:3, on a weight basis.

Cationic Surfactants. Exemplary cationic surfactants include, but are not limited to, salts of optionally polyoxyalkylenated primary, secondary, or tertiary fatty amines; quaternary ammonium salts such as tetraalkylammonium, alkylamidoalkyltrialkylammonium, trialkylbenzylammonium, trialkylhydroxyalkylammonium, or alkylpyridinium having compatible anionic counterions such as halides (preferably chlorides or bromides) or alkyl sulfates such as methosulfate or ethosulfate as well as other anionic counterions; imidazoline derivatives; amine oxides of a cationic nature (e.g., at an acidic pH).

In certain preferred embodiments, the cationic surfactants useful in the compositions of the present invention are selected from the group consisting of tetralkyl ammonium, trialkylbenzylammonium, and alkylpyridinium halides, and mixtures thereof.

Also particularly preferred are amine oxide surfactants including alkyl and alkylamidoalkyldialkylamine oxides of the following formula:

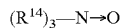

wherein $R^{14}$ is a (C1-C30)alkyl group (preferably a (C1-C14) alkyl group) or a (C6-C18)aralklyl or alkaryl group, wherein any of these groups can be optionally substituted in or on the chain by N-, O-, or S-containing groups such as amide, ester, hydroxyl, and the like. Each $R^{14}$ may be the same or different provided at least one $R^{14}$ group includes at least eight carbons. Optionally, the $R^{14}$ groups can be joined to form a heterocyclic ring with the nitrogen to form surfactants such as amine oxides of alkyl morpholine, alkyl piperazine, and the like. Preferably two $R^{14}$ groups are methyl and one $R^{14}$ group is a (C12-C16)alkyl or alkylamidopropyl group. Examples of amine oxide surfactants include those commercially available under the trade designations AMMONYX LO, LMDO, and CO, which are lauryldimethylamine oxide, laurylamidopropyldimethylamine oxide, and cetyl amine oxide, all from Stepan Company.

Anionic Surfactants. Exemplary anionic surfactants include, but are not limited to, sarcosinates, glutamates, alkyl sulfates, sodium or potassium alkyleth sulfates, ammonium alkyleth sulfates, ammonium laureth-n-sulfates, laureth-n-sulfates, isethionates, alkyl and aralkyl glycerylether sulfonates, alkyl and aralkyl sulfosuccinates, alkylglyceryl ether sulfonates, alkyl phosphates, aralkyl phosphates, alkylphosphonates, and aralkylphosphonates. These anionic surfactants may have a mono- or divalent metal or organic ammonium counterion. In certain preferred embodiments, the anionic surfactants useful in the compositions of the present invention are selected from the group consisting of:

1. Sulfonates and Sulfates. Suitable anionic surfactants include sulfonates and sulfates such as alkyl sulfates, alkylether sulfates, alkyl sulfonates, alkylether sulfonates, alkylbenzene sufonates, alkylbenzene ether sulfates, alkylsulfoacetates, secondary alkane sulfonates, secondary alkylsulfates, and the like. Many of these can be represented by the formulas:

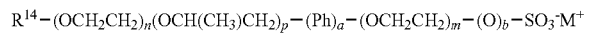

and

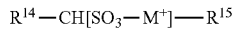

wherein: a and b=0 or 1; n, p, and m=0-100 (preferably 0-20, and more preferably 0-10); $R^{14}$ is defined as above provided at least one $R^{14}$ or $R^{15}$ is at least C8; $R^{15}$ is a (C1-C12)alkyl group (saturated straight, branched, or cyclic group) that may be optionally substituted by N, O, or S atoms or hydroxyl, carboxyl, amide, or amine groups; Ph=phenyl; and M is a cationic counterion such as H, Na, K, Li, ammonium, or a protonated tertiary amine such as triethanolamine or a quaternary ammonium group.

In the formula above, the ethylene oxide groups (i.e., the "n" and "m" groups) and propylene oxide groups (i.e., the "p" groups) can occur in reverse order as well as in a random, sequential, or block arrangement. Preferably for this class, $R^{14}$ includes an alkylamide group such as $R^{16}$—C(O)N(CH$_3$)CH$_2$CH$_2$— as well as ester groups such as —OC(O)—CH$_2$— wherein $R^{16}$ is a (C8-C22)alkyl group (branched, straight, or cyclic group). Examples include, but are not limited to: alkyl ether sulfonates such as lauryl ether sulfates such as POLYSTEP B12 (n=3-4, M=sodium) and B22 (n=12, M=ammonium) available from Stepan Company, Northfield, Ill. and sodium methyl taurate (available under the trade designation NIKKOL CMT30 from Nikko Chemicals Co., Tokyo, Japan); secondary alkane sulfonates such as Hostapur SAS which is a Sodium (C14-C17)secondary alkane sulfonates (alpha-olefin sulfonates) available from Clariant Corp., Charlotte, N.C.; methyl-2-sulfoalkyl esters such as sodium methyl-2-sulfo(C12-16)ester and disodium 2-sulfo (C12-C16)fatty acid available from Stepan Company under the trade designation ALPHASTEP PC-48; alkylsulfoacetates and alkylsulfosuccinates available as sodium laurylsulfoacetate (under the trade designation LANTHANOL LAL) and disodiumlaurethsulfosuccinate (STEPANMILD SL3), both from Stepan Company; alkylsulfates such as ammoniumlauryl sulfate commercially available under the trade designation STEPANOL AM from Stepan Company; dialkylsulfosuccinates such as dioctylsodiumsulfosuccinate available as Aerosol OT from Cytec Industries.

2. Phosphates and Phosphonates. Suitable anionic surfactants also include phosphates such as alkyl phosphates, alkylether phosphates, aralkylphosphates, and aralkylether phosphates. Many may be represented by the formula:

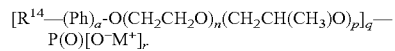

wherein: Ph, $R^{14}$, a, n, p, and M are defined above; r is 0-2; and q=1-3; with the proviso that when q=1, r=2, and when q=2, r=1, and when q=3, r=0. As above, the ethylene oxide groups (i.e., the "n" groups) and propylene oxide groups (i.e., the "p" groups) can occur in reverse order as well as in a random, sequential, or block arrangement. Examples include a mixture of mono-, di- and tri-(alkyltetraglycolether)-o-phosphoric acid esters generally referred to as trilaureth-4-phosphate commercially available under the trade designation HOSTAPHAT 340KL from Clariant Corp., as well as PPG-5 ceteth 10 phosphate available under the trade designation CRODAPHOS SG from Croda Inc., Parsipanny, N.J., and mixtures thereof.

Amphoteric Surfactants. Surfactants of the amphoteric type include surfactants having tertiary amine groups, which may be protonated, as well as quaternary amine containing zwitterionic surfactants. Those that have been particularly useful include:

1. Ammonium Carboxylate Amphoterics. This class of surfactants can be represented by the following formula:

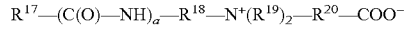

wherein: a=0 or 1; $R^{17}$ is a (C7-C21)alkyl group (saturated straight, branched, or cyclic group), a (C6-C22)aryl group, or a (C6-C22)aralkyl or alkaryl group (saturated straight, branched, or cyclic alkyl group), wherein $R^{17}$ may be optionally substituted with one or more N, O, or S atoms, or one or more hydroxyl, carboxyl, amide, or amine groups; $R^{19}$ is H or a (C1-C8)alkyl group (saturated straight, branched, or cyclic group), wherein $R^{19}$ may be optionally substituted with one or more N, O, or S atoms, or one or more hydroxyl, carboxyl, amine groups, a (C6-C9)aryl group, or a (C6-C9)aralkyl or alkaryl group; and $R^{18}$ and $R^{20}$ are each independently a (C1-C10)alkylene group that may be the same or different and may be optionally substituted with one or more N, O, or S atoms, or one or more hydroxyl or amine groups.

More preferably, in the formula above, $R^{17}$ is a (C1-C18) alkyl group, $R^{19}$ is a (C1-C2)alkyl group preferably substituted with a methyl or benzyl group and most preferably with a methyl group. When $R^{19}$ is H it is understood that the surfactant at higher pH values could exist as a tertiary amine with a cationic counterion such as Na, K, Li, or a quaternary amine group.

Examples of such amphoteric surfactants include, but are not limited to: certain betaines such as cocobetaine and cocamidopropyl betaine (commercially available under the trade designations MACKAM CB-35 and MACKAM L from McIntyre Group Ltd., University Park, Ill.); monoacetates such as sodium lauroamphoacetate; diacetates such as disodium lauroamphoacetate; amino- and alkylamino-propionates such as lauraminopropionic acid (commercially available under the trade designations MACKAM 1L, MACKAM 2L, and MACKAM 151L, respectively, from McIntyre Group Ltd.).

2. Ammonium Sulfonate Amphoterics. This class of amphoteric surfactants is often referred to as "sultaines" or "sulfobetaines" and can be represented by the following formula

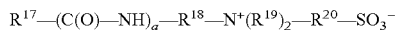

$$R^{17}-(C(O)-NH)_a-R^{18}-N^+(R^{19})_2-R^{20}-SO_3^-$$

wherein $R^{17}-R^{20}$ and "a" are defined above. Examples include cocamidopropylhydroxysultaine (commercially available as MACKAM 50-SB from McIntyre Group Ltd.). The sulfoamphoterics may be preferred over the carboxylate amphoterics since the sulfonate group will remain ionized at much lower pH values.

Nonionic Surfactants. Exemplary nonionic surfactants include, but are not limited to, alkyl glucosides, alkyl polyglucosides, polyhydroxy fatty acid amides, sucrose esters, esters of fatty acids and polyhydric alcohols, fatty acid alkanolamides, ethoxylated fatty acids, ethoxylated aliphatic acids, ethoxylated fatty alcohols (e.g., octyl phenoxy polyethoxyethanol available under the trade name TRITON X-100 and nonyl phenoxy poly(ethyleneoxy) ethanol available under the trade name NONIDET P-40, both from Sigma, St. Louis, Mo.), ethoxylated and/or propoxylated aliphatic alcohols (e.g., that available under the trade name Brij from ICI), ethoxylated glycerides, branched or linear ethoxylated/propoxylated block copolymers such as Pluronic and Tetronic surfactants from BASF, ethoxylated cyclic ether adducts, ethoxylated amide and imidazoline adducts, ethoxylated amine adducts, ethoxylated mercaptan adducts, ethoxylated condensates with alkyl phenols, ethoxylated nitrogen-based hydrophobes, ethoxylated polyoxypropylenes, polymeric silicones, fluorinated surfactants (e.g., those available under the trade names FLUORAD-FS 300 from Minnesota Mining and Manufacturing Co., St. Paul, Minn., and ZONYL from Dupont de Nemours Co., Wilmington, Del.), and polymerizable (reactive) surfactants (e.g., SAM 211 (alkylene polyalkoxy sulfate) surfactant available under the trade name MAZON from PPG Industries, Inc., Pittsburgh, Pa.). In certain preferred embodiments, the nonionic surfactants useful in the compositions of the present invention are selected from the group consisting of Poloxamers such as PLURONIC from BASF, sorbitan fatty acid esters, and mixtures thereof.

Hydrophilic Component

Compositions of the present invention can include a hydrophilic or water-soluble component to help solubilize and/or physically stabilize the antiseptic and/or enhancer component in the composition and/or to enhance the antimicrobial efficacy and/or the speed of antimicrobial efficacy. Incorporation of a sufficient amount of hydrophilic component in hydrophobic ointments results in compositions with significantly better antimicrobial activity both in terms of speed of kill and extent of kill. While not intended to be bound by theory, the incorporation of the hydrophilic component may allow more antiseptic to be available at the surface or to more rapidly diffuse to the surface of the ointment during use. Certain compositions may be solutions, emulsions (one liquid/gel/paste dispersed in another liquid/gel/paste), or dispersions (solid in liquid/paste/gel).

In general, the ratio of total hydrophilic component to total hydrophobic component (water insoluble ingredients) should be at least 5:95 wt/wt, preferably at least 10:90 wt/wt, more preferably at least 15:85 wt/wt and most preferably at least 20:80 wt/wt. Levels as high as 30:70, 40:60, 50:50 wt/wt of total hydrophilic component to total hydrophobic component (water insoluble ingredients) or higher may be appropriate for certain compositions.

A hydrophilic material is typically a compound that has a solubility in water of at least 7 wt-%, preferably at least 10 wt-%, more preferably at least 20 wt-%, even more preferably at least 25 wt-%, and even more preferably at least 40 wt-%, at 23° C. Most preferably, a hydrophilic component is infinitely miscible with water at 23° C.

Exemplary hydrophilic components include, but are not limited to, water, polyhydric alcohols, lower alkyl ethers (i.e., having a sufficiently small number of carbon atoms to meet the solubility limit above), N-methylpyrrolidone, alkyl esters (i.e., having a sufficiently small number of carbon atoms to meet the solubility limit above), and the lower monohydroxy alcohols discussed above as enhancers, as well as combinations thereof. Thus, a lower monohydroxy alcohol can function as both a hydrophilic compound and an enhancer. Preferably, the hydrophilic components include polyhydric alcohols, lower alkyl ethers, and short chain esters. More preferably, the hydrophilic components include polyhydric alcohols.

Suitable polyhydric alcohols (i.e., organic compounds having more than one hydroxyl group) have a molecular weight of less than 500, preferably less than 400, and more preferably less than 200. Examples of polyhydric alcohols include, but are not limited to, glycerol, propylene glycol, dipropylene glycol, tripropylene glycol, polypropylene glycol, polyethylene glycol, diethylene glycol, pentaerythritol, trimethylolpropane, trimethylolethane, trimethylolbutane, sorbitol, mannitol, xylitol, pantothenol, ethylene glycol adducts of polyhydric alcohol, propylene oxide adducts of polyhydric alcohol, 1,3-butanediol, dipropylene glycol, diglycerine, polyglycerine, erythritol, sorbitan, sugars (e.g., sucrose, glucose, fructose, mannose, xylose, saccharose, trehalose), sugar alcohols, and the like. Certain preferred polyhydric alcohols include glycols (i.e., those containing two hydroxyl groups) including glycerin and propylene glycol. Certain other preferred polyhydric alcohols include sucrose, xylitol, mannitol, sorbitol, and polyglycerin.

Ethers include materials such as dimethylisosorbide, polyethylene glycol and methoxypolyethylene glycols, block and random copolymers of ethylene oxide and propylene oxide, and laureth-4. Alkyl esters include triacetin, methyl acetate, esters of polyethoxylated glycols, and combinations thereof.

In certain preferred embodiments, the hydrophilic components useful in the compositions of the present invention include those selected from the group consisting of glycols, and in particular glycerin and propylene glycol, and mixtures thereof.

If there are components in the composition that may esterify with hydroxylfunctional hydrophilic components conditions are selected to minimize this occurrence. For example, the components are not heated together for extended periods of time, the pH is close to neutral if possible, and the like.

One or more hydrophilic materials may be used in the compositions of the present invention at a suitable level to produce the desired result. In certain preferred embodiments that also include the hydrophobic component as the primary component (i.e., the component used in the greatest amount and referred to as a "vehicle"), the hydrophilic component is present in a total amount of at least 0.1 wt-%, preferably at least 1 wt-%, more preferably at least 4 wt-%, and even more preferably at least 8 wt-%, based on the weight of the ready to use composition. In certain embodiments, for example when faster rate of kill is desired, higher levels of hydrophilic component may be employed. In these cases the hydrophilic component is present in a total amount of at least 10% by weight, more preferably at least 20% by weight and most preferably at least 25% by weight. In a preferred embodiment, the hydrophilic component is present in a total amount of no greater than 70 wt-%, more preferably no greater than 60 wt-%, and even more preferably no greater than 50 wt-%, based on the ready to use composition. When the hydrophilic component is present in the greatest amount it is referred to as a "vehicle." When a slower release of the antiseptic is desired the hydrophilic component is present in an amount no greater than about 30% by weight.

For certain applications it may be desirable to formulate these antiseptics in compositions comprising a hydrophilic component vehicle that is thickened with soluble, swellable or insoluble (e.g., insoluble) organic polymeric thickeners or inorganic thickeners such as silica, fumed silica, precipitated silica, silica aerogel and carbon black, and the like; other particle fillers such as calcium carbonate, magnesium carbonate, kaolin, talc, titanium dioxide, aluminum silicate, diatomaceous earth, ferric oxide and zinc oxide, clays, and the like; ceramic microspheres or glass microbubbles; ceramic microspheres such as those available under the trade names "ZEOSPHERES" or "Z-LIGHT" from 3M. The above fillers can be used alone or in combination.

If water is used in certain embodiments, it is present in an amount of less than 20 wt %, preferably less than 10 wt-%, more preferably less than 5 wt-%, and even more preferably less than 2 wt-%, based on the ready to use composition. This helps the chemical stability of the compositions and may reduce irritation. For certain other embodiments, water can be used in a much greater amount, and can even be the primary component, as long as the composition is highly viscous. Preferably, such highly viscous compositions have a viscosity of at least 500 centipoises (cps), more preferably at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as about 500,000 cps, 1,000,000 cps, or more). The viscosity can be measured as described below in the Viscosity Test. Most preferred compositions meet these viscosity values even after heating to 32° C., preferably 35° C. or as high as 37° C. to ensure when in contact with mammalian tissue the compositions remain substantive.

Hydrophobic Component

Certain preferred compositions of the present invention also include one or more hydrophobic materials. A hydrophobic material is typically an organic compound, which at 23° C. is a liquid, gelatinous, semisolid or solid and has a solubility in water of less than 5% by weight, preferably less than 1% by weight, more preferably less than 0.5% by weight, and most preferably less than 0.1% by weight. These materials include compounds typically considered emollients in the cosmetic art.

Examples of general emollients include, but are not limited to, short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12)aryl esters of (C4-C12)diacids or (C4-C12)diols optionally substituted in available positions by —OH; (C2-C18)alkyl or (C6-C12)aryl esters of glycerol, pentaerythritol, ethylene glycol, propylene glycol, as well as polyethoxylated derivatives of these; (C12-C22)alkyl esters or (C12-C22)ethers of polypropylene glycol; (C12-C22)alkyl esters or (C12-C22)ethers of polypropylene glycol/polyethylene glycol copolymer; and polyether polysiloxane copolymers.

Additional examples of hydrophobic components include cyclic dimethicones including volatile cyclic silicones such as D3 and D4, polydialkylsiloxanes, polyaryl/alkylsiloxanes, silicone copolyols, long chain (i.e., C8-C36) alkyl and alkenyl esters of long (i.e., C8-C18) straight or branched chain alkyl or alkenyl alcohols or acids, long chain (i.e., C8-C36) alkyl and alkenyl amides of long straight or branched chain (i.e., C8-C36) alkyl or alkenyl amines or acids; hydrocarbons including straight and branched chain alkanes and alkenes such as isoparafins (e.g., isooctane, isododecane, isooctadecane, etc.), squalene, and mineral oil, polysiloxane polyalkylene copolymers, dialkoxy dimethyl polysiloxanes; (C12-C22)alkyl and (C12-C22)alkenyl alcohols, and petroleum derived alkanes such as isoparafins, petrolatum, petrolatum USP, as well as refined natural oils (especially NF or USP grades) such as olive oil NF, cotton seed oil, peanut oil, corn oil, sesame oil, safflower oil, soybean oil, and the like, and blends thereof.

In certain preferred embodiments, the hydrophobic components useful in the compositions of the present invention include those selected from the group consisting of petrolatum USP and short chain (i.e., C1-C6) alkyl or (C6-C12)aryl esters of long (i.e., C8-C36) straight or branched chain alkyl or alkenyl alcohols or acids and polyethoxylated derivatives of the alcohols; short chain (i.e., C1-C6) alkyl or (C6-C12) aryl esters of (C4-C12)diacids or (C4-C12)diols optionally substituted in available positions by —OH (such as diisopropyladipate, diisopropylsebacate); (C1-C9)alkyl or (C6-C12) aryl esters of glycerol, pentaerythritol, ethylene glycol, propylene glycol (such as glyceryl tricaprylate/caprate); and mixtures thereof. For certain particularly preferred embodiments, the hydrophobic component is petrolatum.

One or more hydrophobic materials may be used in the compositions of the present invention at a suitable level to produce the desired result. In a preferred embodiment (in which the compositions include very little or no water), the hydrophobic component is present in a total amount of at least 30 wt-%, preferably at least 50 wt %, more preferably at least 60 wt-%, and even more preferably at least 70 wt-%, based on the ready to use composition. In a preferred embodiment, the hydrophobic component is present in a total amount of no greater than 99 wt-%, more preferably no greater than 95 wt-%, and even more preferably no greater than 92 wt-%, based on the ready to use composition. When the hydrophobic component is present in the greatest amount it is referred to as a "vehicle." If the hydrophobic component(s) and the hydrophilic component(s) are present at the same concentrations the continuous phase is consider the "vehicle".

Optional Additives

Compositions of the present invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, anti-parasitic agents, antipruritics, astringents, local anesthetics, steroids, non-steroidal antiinflammatory agents, or other anti-inflammatory agents), or may contain materials useful in physically formulating various dosage forms of the present invention, such as excipients, dyes, perfumes, fragrances, lubricants, thickening agents, stabilizers, skin penetration enhancers, preservatives, or antioxidants.

In those applications where emulsions are desirable, an emulsifier may be used. As used herein, an "emulsifier" means a small molecule or polymeric amphiphilic compound capable of helping to stabilize an emulsion. Emulsifiers used herein include many of the surfactants disclosed but may also include many other amphiphilic molecules. The emulsions are detectably more stable with the emulsifier present than without as determined by centrifugation and/or freeze thaw studies.

It will be appreciated by the skilled artisan that the levels or ranges selected for the required or optional components described herein will depend upon whether one is formulating a composition for direct use, or a concentrate for dilution prior to use, as well as the specific component selected, the ultimate end-use of the composition, and other factors well known to the skilled artisan.

It will also be appreciated that additional antiseptics, disinfectants, or antibiotics may be included and are contemplated. These include, for example, addition of metals such as silver, copper, zinc; iodine and iodophors: "azole" antifungal agents including clortrimazole, miconazole, econazole, ketoconazole, and salts thereof; and the like. Antibiotics such as neomycin sulfate, bacitracin, mupirocin, tetracycline, polymixin, and the like, also may be included. Preferred compositions, however, are free of antibiotics due to the chance of resistance formation.

Formulations and Methods of Preparation

Many of the compositions of the present invention demonstrate a broad spectrum of antimicrobial activity and thus are generally not terminally sterilized but if necessary may be sterilized by a variety of industry standard techniques. For example, it may be preferred to sterilize the compositions in their final packaged form using electron beam. It may also be possible to sterilize the sample by gamma radiation or heat. Other forms of sterilization may be acceptable. It may also be suitable to include preservatives in the formulation to prevent growth of certain organisms. Suitable preservatives include industry standard compounds such as parabens (methyl, ethyl, propyl, isopropyl, isobutyl, etc), 2 bromo-2 nitro-1,3, diol; 5 bromo-5-nitro-1,3 dioxane, chlorbutanol, diazolidinyl urea; iodopropylnyl butylcarbamate, phenoxyethanol, halogenated cresols, methylchloroisothiazolinone and the like, as well as combinations of these compounds.

The compositions of the present invention preferably adhere well to mammalian tissue (e.g., skin, mucosal tissue, and wounds), in order to deliver the antimicrobial to the intended site over a prolonged period even in the presence of perspiration, drainage (e.g., mucosal secretions), or mild lavage. The compositions are typically non-aqueous, although high viscosity compositions can include a large amount of water. The component in the greatest amount (i.e., the vehicle) in the formulations of the invention may be any conventional vehicle commonly used for topical treatment of human or animal skin. The formulations are typically selected from one of the following five types: (1) formulations with a hydrophobic vehicle (i.e., the hydrophobic component, which can include one or more hydrophobic compounds, present in the greatest amount) which may be anhydrous, nearly anhydrous or further comprise a aqueous phase; (2) formulations based on water in oil emulsions in which the water insoluble continuous "oil" phase is comprised of one or more hydrophobic components; (3) formulations with a hydrophilic vehicle (i.e., the hydrophilic component, which can include one or more hydrophilic compounds, is present in the greatest amount) which may be anhydrous, nearly anhydrous or further comprise a aqueous phase; (4) highly viscous water-based formulations which may be solutions or oil in water emulsions; and 5) neat compositions which are essentially free of a hydrophobic or hydrophilic vehicle component comprising antiseptic, optionally an enhancer, and further optionally a surfactant. In this latter case the compositions may optionally be dissolved in a volatile carrier solvent for delivery to the intended treatment site or may be delivered to the site as a dry powder, liquid, or semi-solid composition. The different types of compositions are discussed further below.

(1) Anhydrous or Nearly Anhydrous Formulations with a Hydrophobic Vehicle: In certain preferred embodiments of the present invention, the compositions include an antiseptic component in a hydrophobic vehicle optionally in combination with surfactant(s), an enhancer component, and a small amount of a hydrophilic component. In most instances the enhancers are not soluble in the hydrophobic component at room temperature although they may be at elevated temperatures. The hydrophilic component is generally present in a sufficient amount to stabilize (and perhaps to solubilize) the enhancer(s) in the composition. For example, when formulating with organic acid enhancers or certain solid surfactants or certain antiseptics in petrolatum many antiseptics, enhancers, and surfactants will dissolve into the petrolatum at temperatures above 85° C.; however, upon cooling, the antiseptic, enhancer and/or surfactant crystals or precipitates back out of solution making it difficult to produce a uniform formulation. If at least 0.1 wt-%, preferably at least 1.0 wt-%, more preferably at least 5 wt-%, and most preferably at least 10 wt-% of a hydrophilic compound (e.g., a glycol) is added a stable formulation can be obtained. It is believed that these formulations produce an emulsion in which the enhancer and/or surfactant is dissolved, emulsified, or dispersed in the hydrophilic component which is emulsified into the hydrophobic component(s). These compositions are stable upon cooling and centrifuging.

The hydrophilic component also helps to stabilize many of the surfactants used in preferred formulations. For example, dioctylsulfosuccinate sodium salt (DOSS) dissolves in glycerin at elevated temperatures and helps keep the DOSS physically stable in the composition. Furthermore, it is believed that incorporation of the hydrophilic component in the formulation improves the antimicrobial activity. The mechanism for this is unknown; however, it may speed the release of the enhancer component and/or the antiseptic component.

The water content of these formulations is preferably less than 20 wt-%, more preferably less than 10 wt-%, and even more preferably less than 5 wt-%, and most preferably less than 2 wt-%, in order to minimize chemical degradation of antiseptics present as well as to reduce concerns with microbial contamination in the composition during storage, and to reduce irritation of the tissue to which it is applied.

These formulations can be manufactured with relative ease. The following description assumes all components are present in order to describe their manufacture. It is understood, however, that certain compositions may not contain one or more of these components. In one method the compositions are manufactured by first heating the hydrophobic component to 85° C., adding in the surfactant, hydrophilic component, and optional enhancer component, cooling to 65° C., and adding the antiseptic component which may be above its melting point. Alternatively, the enhancer component, if used, can be predissolved in the hydrophilic component (optionally along with the surfactant) and added to the hydrophobic component either before or after addition of the antiseptic component. If either the antiseptic component or the hydrophobic component is solid at room temperature, this is done at the minimum temperature necessary to ensure dissolution and uniformity of the composition. Exposure of ester-containing antiseptics or excipients to enhancers or other components comprising either acid or hydroxyl groups at elevated temperatures for extended periods of time should be avoided to prevent transesterification reactions. There are exceptions, for example, when heating lower purity fatty acid esters in combination with glycol hydrophilic components to produce the monoesters of higher purity.

Thus, the present invention provides methods of manufacture. One method involves: combining the hydrophobic vehicle and the hydrophilic component with mixing to form a mixture; optionally heating the hydrophobic vehicle to a temperature sufficient to form a pourable liquid (which for many hydrophobic vehicles this is above its melting point) before or after combining it with the hydrophilic component; adding the antiseptic component to the mixture; and cooling the mixture before or after adding the antiseptic component.

One preferred method involves: dissolving at least a portion of the enhancer component in the hydrophilic component; combining the hydrophobic vehicle and the hydrophilic component with the enhancer component dissolved therein with mixing to form a mixture; optionally heating the hydrophobic vehicle to a temperature sufficient to form a pourable liquid (which for many hydrophobic vehicles this is above its melting point) before or after combining it with the hydrophilic component and enhancer component; adding the antiseptic component to the mixture; and cooling the mixture before or after adding the antiseptic component.

The hydrophilic component may or may not be present in the formulations that include a hydrophobic vehicle. Thus, another preferred method of manufacture involves: optionally heating the hydrophobic vehicle to a temperature sufficient to form a pourable liquid (which for many hydrophobic vehicles is above its melting point) before or after combining it with the optional enhancer component; adding the antiseptic component to the mixture with mixing; and cooling the mixture before or after adding the antiseptic component.

Surprisingly, it has been found that these compositions are significantly less irritating than formulations using hydrophilic vehicles. In blind human trials, participants were asked to instill 0.5 gram (g) of ointments based on hydrophobic components (e.g., petrolatum) that include an AHA enhancer, surfactant, and 10 wt-% hydrophilic component (e.g., glycerin) as well as ointments based on hydrophilic components (e.g., PEG 400) using the same enhancer and surfactant. The ointments with the hydrophobic vehicle were preferred by 100% of the participants.

The viscosity of these formulations intended for use on skin or in the anterior nares is preferably relatively high to prevent excessive drainage off the treatment site. Most preferably, the formulations intended for use on skin, anterior nares, or where drainage would be a concern are essentially gelatinous at room temperature, having a significant yield point such that they do not flow readily at temperatures below 35° C. The viscosity is measured using the viscosity test described herein. Certain gelatinous vehicles may also have a characteristic temperature at which they "melt" or begin to dramatically lose viscosity. Preferably this is higher than body temperature also to ensure that excess drainage of the composition of the treatment site does not occur. Therefore, the melting point of the composition is preferably greater than 32° C., more preferably greater than 35° C., and even more preferably greater than about 37° C. The melting point is taken as the lowest temperature at which the viscosity becomes dramatically less or is equal to or less than 100,000 cps.

Alternatively, formulations could be considered which gel or thicken when warmed to body temperature. For example, aqueous compositions based on Pluronic F127 (e.g., greater than about 17% by weight), as well as other Poloxamers of similar structure, are relatively low viscosity at 4° C. but when warmed to body temperature become very viscous. In these applications, the viscosity should be measured at 35° C.

Similarly the viscosity and/or melt temperature can be enhanced by either incorporating a crystalline or semicrystalline emulsifier and/or hydrophobic carrier such as a higher melting petrolatum, addition of an insoluble filler/thixotrope, or by addition of a polymeric thickener (e.g., a polyethylene wax in a petrolatum vehicle). Polymeric thickeners may be linear, branched, or slightly crosslinked. It is important for comfort that the formulations are relatively soft and that they spread easily to allow easy application, especially over a wound, rash, or infected area or in the anterior nares. A particularly preferred vehicle for use on skin, in the anterior nares, or in other areas where high viscosity is desirable is white petrolatum USP having a melting point greater than 40° C.

(2) Water in Oil Emulsions: Antiseptic components of this invention can be formulated into water-in-oil emulsions in combination with enhancer(s) and surfactant(s). Particularly preferred compositions comprise at least 35 wt-%, preferably at least 40 wt-%, more preferably at least 45 wt-% and most preferably at least 50% by weight oil phase. As used herein the oil phase is comprised of all components which are either insoluble in water or preferentially soluble in the oil(s) present at 23° C. One method of preparing these emulsions is described in applicant's copending U.S. Ser. No. 09/966,571. Generally speaking the hydrophobic component (oil) is mixed in a first container along with any emulsifier(s) optionally including polymeric emulsifiers and heated to a temperature sufficient to ensure a homogenous composition and subsequent stable emulsion. The temperature is typically raised to at least 60° C., preferably to at least 80° C. and more preferably to 100° C. or more. In a separate second container, the hydrophilic ingredients are mixed, including one or more of the following: water, hydrophilic component, enhancer(s), surfactant(s), and acids/bases to adjust the pH of the final composition. The contents of the second container are heated to a temperature sufficient to ensure a stable final emulsion composition without significantly degrading any of the components, typically greater than 40° C., preferably greater than 50° C. and more preferably to greater than 60° C. While hot, the second container is added to the first container using a high shear mixer. The composition may be continuously mixed until cool (T<40° C.) or it can be allowed to sit as long as the contents remain uniformly mixed. If the antiseptic is heat sensitive, it is added with mixing during the cooling down period. If it is not heat sensitive, it may be added to either container. The viscosity of these compositions may be adjusted by altering the levels of emulsifier; changing the ratio of water to oil phase; selection of the oil phase (e.g., select an oil (hydrophobic component) which is more or less viscous); incorporation of a polymeric or particulate thickener, etc.

(3) Hydrophilic Vehicle: Antiseptic components of this invention can be formulated into a hydrophilic component such as that based on the hydrophilic compounds discussed above optionally in combination with the enhancer(s) and surfactant(s). Particularly preferred are polyethylene glycols (PEGs), glycols, and combinations thereof, including blends of different molecular weight PEGs optionally containing one or more glycols. When using a hydrophilic component as the vehicle (i.e., the component used in the greatest amount, which can include one or more hydrophilic compounds), it should be preferably selected to maintain viscosity and melt temperature characteristics similar to those stated above for the anhydrous or nearly anhydrous formulations using a hydrophobic vehicle.

Similarly the viscosity can be enhanced by either incorporating a crystalline or semicrystalline hydrophilic compound such as a PEG of sufficient molecular weight, addition of an insoluble filler/thixotrope, or by addition of a polymeric thickener. Polymeric thickeners may be linear, branched, or slightly crosslinked. It is important for comfort that the formulations are relatively soft and that they spread easily to allow easy application, especially in the anterior nares or over a wound, rash, or infected area. For this reason, a particularly preferred vehicle is based on a blend of a liquid or semi-solid PEG (PEG 400-1000) with a more crystalline PEG (PEG 1000-2000). Particularly preferred is a blend of PEG 400 with PEG 1450 in a ratio of 4:1.

In certain preferred embodiments of the present invention, the compositions are in the form of an ointment or cream. That is, the compositions are in the form of a relatively viscous state such that they are suitable for application to nasal passageways.

(4) Water-based Formulations: Aqueous compositions of the present invention are those in which water is present in the greatest amount, thereby forming the "vehicle." For these systems it is particularly important that a relatively high viscosity be imparted to the composition to ensure that the antimicrobial composition is not rapidly dispersed off the treated area. These formulations also adhere well to tissue and thus deliver the antiseptic to the intended site over a prolonged period even in the presence of perspiration, drainage (e.g., mucosal secretions), or mild lavage. Such a high viscosity can be imparted by a thickener system. The thickener system of the invention is compatible with the antiseptic composition described above in order to provide suitable antimicrobial efficacy, chemical and physical stability, acceptable cosmetic properties, and appropriate viscosity for retention in the afflicted area.

Preferred thickener systems used in the compositions of the present invention are capable of producing viscoelastic compositions that are very stable. By varying the amount and type of thickener, the degree of elasticity can be adjusted from almost a purely viscous composition to a highly elastic and even gel-like composition. If emollients are added, increasing the elasticity and/or yield stress of the system imparts added stability to prevent separation of immiscible emollients. Excessive elasticity, however, is not preferred because an excessively elastic composition usually does not provide a cosmetically appealing product.

Significantly, thickener systems used in the present invention are capable of achieving high viscosities at relatively low total concentrations. The total concentration of the thickener system is preferably less than 8 wt-%, more preferably less than 5 wt-%, and most preferably less than 3 wt-%, based on the total weight of the ready to use composition. Preferably, the total concentration of the thickener system can be as little as 0.5 wt-%, based on the total weight of the composition. For certain embodiments, however, the total concentration of thickener system is greater than 1 wt-%, based on the total weight of the ready to use composition.

The thickener system can include organic polymers or inorganic thixotropes such as silica gel, clays (such as betonite, laponite, hectorite, montmorrillonite and the like), as well as organically modified inorganic particulates materials, and the like. As used herein, an organic polymer is considered part of the thickener system if its presence in the composition results in an increase in the viscosity of the composition. Certain polymers that do not have these characteristics may also be present in the composition but do not contribute significantly to the viscosity of the composition. For purposes of this invention, they are not considered part of the thickener system. For example, certain nonionic polymers such as lower molecular weight polyethylene glycols (e.g., those having a molecular weight of less than 20,000) do not increase the viscosity of the composition significantly. These are considered part of the hydrophilic component, for example, rather than part of the thickener system.

The thickener system can be prepared from one or more nonionic, cationic, anionic, zwitterionic, or associative polymers as long as they are compatible with the antiseptic and enhancer components of the composition. For example, certain acidic enhancers such as those that include carboxylic acid groups are most effective in their protonated form. This requires that the composition has an acidic pH. For this reason, many anionic thickeners based on neutralized carboxylic acid groups would not be suitable. For example, Carbopol-type thickeners based on polyacrylic acid salts do not typically thicken well at pH values of less than 5 and certainly less than a pH of 4.5. Therefore, at lower pH values (i.e., when acidic enhancers are present) if the aqueous compositions are thickened with anionic polymers, the polymers are preferably based on sulfonic acid, sulfate, phosphonic acid, or phosphate groups. These polymers are able to thicken at much lower pH values due to the lower pKa of these acid groups. Preferred polymers of this class include ARISTOFLEX HMB (ammonium acryloyldimethyltaurate/beheneth-25 methacrylate crosspolymer) and ARISTOFLEX ASV (ammonium acryloyldimethyltaurate/NVP copolymer) from Clariant Corporation. Other preferred sulfonic acid polymers are those described in U.S. Pat. No. 5,318,955.

Preferably, the compositions that include an acidic enhancer component are thickened using cationic or nonionic thickeners since these perform well at low pH. In addition, many of the nonionic and cationic polymers can tolerate higher levels of salts and other additives and still maintain high viscosity.

A preferred group of nonionic polymeric thickeners include modified celluloses, guar, xanthan gum, and other natural polymers such as polysaccharides and proteins, associative polymers based on nonionic ethylenically unsaturated monomers wherein at least one comonomer has at least 16 carbon atoms, and polymers based on ethylenically unsaturated monomers selected from the group consisting of acrylates, acrylamides, vinyl lactams, vinyl acetate and its hydrolyzed derivatives, methyl vinyl ethers, styrene, and acrylonitrile.

A preferred group of cationic polymeric thickeners include cationically modified celluloses, quaternized natural amino-functional polymers, and polymers based on ethylenically unsaturated monomers selected from the group consisting of acrylates, acrylamides, vinyl lactams, vinyl acetates, methyl vinyl ethers, styrene, and acrylonitrile.

Cationic polymers for use in the compositions of this invention can be selected from both permanently charged quaternary polymers (those polymers with quaternary amines such as Polyquatemium 4, 10, 24, 32, and 37, described below) as well as protonated primary, secondary, and tertiary amine functional polymers that have been protonated with a suitable protonic acid. Preferred protonated cationic polymers are based on tertiary amines. The protonated cationic polymers are preferably protonated with suitable acids that will not result in undue skin irritation. These include, for example, (C1-C10)alkylcarboxylic acids optionally substituted by oxygen (e.g., acetic acid, alpha-hydroxy acids such as lactic acid, gluconic acid, benzoic acid, mandelic acid, and the like), (C1-C10)alkylsulfonic acids (e.g., methylsulfonic acid and ethylsulfonic acid), (C1-C10)alkylhydrogensulfates (e.g., methylhydrogensulfate) and mineral acids (e.g., hydrochloric acid, hydrobromic acid, sulfuric acid, phosphoric acid, and the like).

The charge on protonated cationic polymers is pH dependent. For this reason, in order to ensure the polymer is sufficiently protonated, the pH is adjusted appropriately and should be in the range of preferably 2-9.5, more preferably 2-8, and most preferably 2.5-7.5. The pH of preferred compositions that include acidic enhancers should be lower and is typically 2-5, and preferably 2-4. It should be noted that it is not necessary to have all of the amines on a particular polymer protonated. The level of protonation will to a certain extent be pH dependent. With certain polymers in order to obtain optimum thickening with low skin irritation it may be beneficial to only protonate a small percentage of the available amine groups while with other polymers it may be beneficial to protonate substantially all of the amine groups. This can be easily determined by one skilled in the art.

The quaternary, tertiary, secondary, and primary amine functional polymers may be chosen from natural polymers, modified natural polymers, as well as synthetic polymers. These polymers may be soluble or swellable in the aqueous solvent. Furthermore, these polymers may also possess hydrophobic side chains and thus be associative polymers.

Polymers can be classified as soluble, swellable, or associative in the aqueous compositions. Some polymers may fall into one or more of these classes. For example, certain associative polymers can be soluble in the aqueous system. Whether they are considered soluble, swellable, or associative in the aqueous system, suitable polymers for use in the compositions of the present invention may be film forming or not. Film forming polymers may retain the active antimicrobial component at the afflicted site for longer periods of time. This may be desirable for certain applications. For example, some film forming polymers may produce compositions that could not be easily washed off with water after being applied and dried.

As used herein, a soluble polymer is one that in dilute solution (i.e., 0.01-0.1 wt-% in the desired aqueous solvent system defined as containing water and any other hydrophilic compounds), after heating for a sufficient time to ensure solubilization of any potentially soluble components, has no significant observable particles of greater than 1 micron in particle size, as determined by light scattering measurements using, for example, Malvern Masterisizer E Laser Particle Size Analyzer available from Malvern Co., Boston, Mass.

As used herein, a swellable polymer is one that in dilute solution (i.e., 0.01-0.1 wt-% in the desired aqueous solvent system), after heating for a sufficient time to ensure solubilization of any potentially soluble components, has a significant (i.e., detectable) number of observable particles of greater than 1 micron in particle size, as determined by light scattering measurements using, for example, Malvern Masterisizer E Laser Particle Size Analyzer.

As used herein, an associative polymer is one that has greater than 2 hydrophobic chains per polymer molecule of greater than 12 and preferably greater than 16 carbon atoms. Examples of such polymers are described below.

Soluble Polymers—Cationic Natural Polymer Derivatives. Cationic modified cellulosic polymers are reported in the literature to be soluble in water. Such polymers have been found to be useful in the present invention. The most preferred modified cellulose products are sold under the trade names CELQUAT (National Starch and Chemicals Corp., Bridgewater, N.J.) and UCARE (Amerchol Corporation, Edison, N.J.). CELQUAT is a copolymer of a polyethoxylated cellulose and dimethyldiallyl ammonium chloride and has the Cosmetic, Toiletry and Fragrance Association (CTFA) designation Polyquatemium-4.

An alkyl modified quaternary ammonium salt of hydroxyethyl cellulose and a trimethyl ammonium chloride substituted epoxide can also be used. The polymer conforms to the CTFA designation Polyquaternium 24 and is commercially available as QUATRISOFT LM-200 from Amerchol Corp., Edison, N.J.

A particularly suitable type of cationic polysaccharide polymer that can be used is a cationic guar gum derivative, such as guar hydroxypropyltrimonium chloride (Commercially available from Rhone-Poulenc under the trade designation JAGUAR).

Soluble Polymers—Cationic Synthetic Polymers. Synthetic cationic linear polymers useful in the present invention are preferably quite high in cationic charge density—generally having greater than 10 wt-% cationic monomer, preferably greater than 25 wt-%, and more preferably greater than 50 wt-%. This ensures a good cosmetic feel and may actually improve water solubility. In general, the polymers useful in the present invention have sufficient molecular weight to achieve thickening at generally less than 5 wt-% polymer, but not too high that the lotion/cream/ointment feels slimy and stringy. While the composition of the polymer will dramatically affect the molecular weight at which sufficient thickening will occur, the polymers preferably have a molecular weight of at least 250,000 daltons, and more preferably at least 500,000 daltons. The polymers preferably have a molecular weight of no greater than 3,000,000 daltons, and more preferably no greater than 1,000,000 daltons. The homopolymers are preferably prepared from methacryloyloxyalkyl trialkyl ammonium salt, acryloyloxyalkyl trialkyl ammonium salt, and/or quaternized dialkylaminoalkylacrylamidine salt. Preferably the polymers are copolymers of at least two monomers selected from the group consisting of trialkylaminoalkyl acrylate and methacrylate salts, dialkyl-diallyl ammonium salts, acrylamidoalkyltrialkyl salts, methacrylamidoalkyltrialkyl salts, and alkyl imidazolinium salts, N-vinyl pyrrolidinone, N-vinyl caprolactam, methyl vinyl ether, acrylates, methacrylates, styrene, acrylonitrile, and combinations thereof. Typically, for the salts the counterions are preferably F$^-$, Cl$^-$, Br$^-$, and CH$_3$(CH$_2$)$_n$SO$_4^-$ where n=0 to 4.

A variety of quaternary copolymers of varying quaternization, can be synthesized based on homo or copolymers of amino acrylates with methyl, ethyl, or propyl side chains. These monomers could also be copolymerized with other nonionic monomers including quaternary acrylic homopolymers, such as homopolymers of 2-methacryloxyethyl trimethylammonium chloride and 2-methacryloxyethyl methyl diethyl ammonium bromide; and copolymers of quaternary acrylate monomers with a water-soluble monomers, such as Petrolite Product No. Q-0043, a proprietary copolymer of a linear quaternary acrylate and acrylamide at high molecular weight (4-5 million MW).

Another useful soluble cationic polymer is poly (N,N-dimethylaminopropyl-N-acrylamidine) (which is quaternized with diethylsulfate) bound to a block of polyacrylonitrile. This block copolymer is available under the trade designation Hypan QT-100 from Lipo Chemicals Inc., Paterson, N.J. It is quite effective at thickening aqueous systems and has a good cosmetic feel. This polymer as received, however, has an objectionable amine odor. The odor could probably be masked with the proper fragrance, but is preferably removed prior to formulation (e.g., with a solvent cleaning process) so that the formulation can be supplied without fragrance. Preferred compositions are free of fragrance and colorants.

Suitable cationic polymers include, for example, copolymers of 1-vinyl-2-pyrrolidine and 1-vinyl-3-methyl-imidazolium salt (e.g., chloride salt), referred to in the industry by the Cosmetic, Toiletry, and Fragrance Association, (CTFA) as Polyquatemium-16. This material is commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate, referred to in the industry (CTFA) as Polyquatemium-11. This material is available commercially from ISP Corp., Wayne, N.J., under the trade designation GAFQUAT; cationic diallyl quaternary ammonium-containing polymers including, for example, dimethyldiallyammonium chloride homopolymer and copolymers of acrylamide and dimethyldiallylammonium chloride, referred to in the industry (CTFA) as Polyquatemium 6 and Polyquatemium 7, respectively.

Soluble Polymers-Nonionic. A variety of cellulosic ethers are reported in the literature to be soluble in water. Materials in this class that are nonionic and have been shown to be useful include: methylhydroxypropylcellulose, available as BENECEL MP 943 from Aqualon, Wilmington, Del.; hydroxypropylcellulose, available as KLUCEL (LF, GF, MF, HF) from Aqualon; hydroxybutylmethylcellulose (3.5 wt-% hydroxybutyl and 30 wt-% methoxyl) from Scientific Polymer Products, Ontario, N.Y.; and hydroxyethylcelluloses, available under the trade designation NATROSOL from Aqualon. Xanthan gum, guar, locust bean gum, and other polysaccharides may also be suitable. These polymers may be produced from plant sources or can be produced through microbial cell culture. Polyvinyl alcohol (PVA) also may be suitable. For example, PVA made from polyvinyl acetate, which has been hydrolyzed to about 87%, is highly water soluble at room temperature. Those with higher percent hydrolysis become progressively more crystalline and may need to be heated to get into solution. Protein thickeners such as gelatin and pectin may also be useful.

Other Soluble Polymers: Amine oxide polymers such as those described in U.S. Pat. No. 6,123,933 and those commercially available under the trade designation DIAFORMER Z-711, Z-712, Z-731, and Z-751 from Clariant Corp. are useful. Additionally, zwitterionic polymers, such as methacryloyl ethyl betaine/acrylate copolymer that are commercially available under the trade designation DIAFORMER Z-400 from Clariant Corp. can also be used. Zwitterionic polymers described in U.S. Pat. No. 6,590,051 may also be useful.

Carboxylic acid functional polymers including naturally occurring carboxylic acid functional polymers such as hyaluronic acid and derivatives of natural polymers such as carboxymethylcellulose, alginic acid and other alginate polymers, Fucogel (a polysaccharide consisting of three monosaccharides, fucose, galactose, and galacturonic acid), hyaluronic acid, and the like, also may be useful. Synthetic polymers may also be useful, such as those based on carboxylic acid, phosphonic acid, or sulfonic acid functional monomers, including but not limited to, polymers derived from acrylic acid, methacrylic acid, maleic anhydride, itaconic anhydride, sodium AMPS (the sodium salt of 2-acrylamido-2-methylpropane sulfonic acid), sulfopropyl acrylate or methacrylate, sulphomethylated acrylamide, allyl sulphonate, sodium vinyl sulphonate, combinations thereof, or other water-soluble forms of these or other polymerizable carboxylic or sulphonic acids.

Swellable Polymers. Many swellable polymers, which are slightly crosslinked, function as viscosifiers in aqueous solvent systems. In general, these swellable polymers are preferred because they tend to be far less "slimy" going on and once the hands perspire and are exposed to water after treatment. Excessive crosslinking will result in polymers that do not swell sufficiently to increase the viscosity of the composition. In order to ensure adequate swelling, if a chemical crosslinker is used, the concentration of crosslinker is quite low, e.g., less than about 1000 parts per million (ppm), and preferably less than 500 ppm, based on the weight of the dry polymer.

A class of crosslinked polymers suitable for use in the compositions of the present invention include acrylamide and at least one other quaternary monomer selected from the group consisting of trialkylaminoalkylacrylate and methacrylate salts, dialkyldiallyl ammonium salts, acrylamidoalkyltrialkyl ammonium salts, methacrylamidoalkyltrialkyl ammonium salts, and monomers that include imidazolinium salts. The counterions are preferably F$^-$, Cl$^-$, Br$^-$, and CH$_3$(CH$_2$)$_n$ SO$_4^-$ where n=0-4. Other comonomers may also be added including N-vinyl pyrrolidone, N-vinyl caprolactam, methyl vinyl ether, acrylates, methacrylates, styrene, and the like. A particularly preferred polymer is a poly(2-methacryloxyethyl trimethyl ammonium chloride) polydimethylaminoethyl methacrylate, which conforms to the CTFA designation Polyquaternium 37. Another preferred polymer includes acrylamide and methacryloyloxyethyl trimethyl ammonium chloride, which conforms to the CTFA designation Polyquaternium 32. These are commercially available from Allied Colloids Inc. of Suffolk, Va. as SALCARE SC95, SC96, and SC92.

Other swellable polymers (i.e., slightly crosslinked polymers) can be prepared using ionizing radiation to crosslink. For example, polymers of N-vinyl lactams, such as N-vinyl pyrrolidone, when exposed to gamma radiation increase in molecular weight and may actually crosslink. This crosslinking allows for more efficient thickening (less polymer required to achieve a certain viscosity) and an improved cosmetic feel. Other polymers that when exposed to gamma radiation result in crosslinking, include polymers such as LUVIQUAT HM 552 (copolymers of vinylimidazolium methochloride and vinylpyrrolidone, which conforms to the CTFA designation Polyquatemium-16), and GAFQUAT HS-100 (vinylpyrrolidone/methacrylamidopropyltrimethylammonium chloride copolymer which conforms to the CTFA designation Polyquatemium-28).

Chemical crosslinking using polyunsaturated monomers such as diallyl maleate may also prove useful. Other suitable crosslinkers are multi-ethylenically unsaturated compounds wherein the ethylenic groups are vinyl groups (including substituted vinyl groups, such as isopropenyl groups), allyl groups, and/or methallyl groups, which groups are bonded to nitrogen or oxygen atoms. Vinyl, allyl, and methallyl groups, as used herein, include substituted derivatives. Exemplary compounds include divinyl, diallyl, or dimethallyl esters, ethers, amides, or ureas. Specific examples are disclosed in U.S. Pat. No. 5,225,473 (Duan) and U.S. Pat. No. 4,931,282 (Asmus et al.).

A range of crosslinked polyvinylpyrrolidone (PVP) materials has been prepared via covalent crosslinking with diallyl maleate or by radiation crosslinking of linear PVP powders. Crosslinked PVP prepared under these techniques can produce colloidal particles which are highly swellable in aqueous solutions and thereby produce viscous solutions. The polymers are also nonionic and have excellent compatibility with cationic excipients.

Anionic swellable polymeric thickeners may also be useful. As described above preferred anionic polymers for use with antimicrobial compositions which include carboxylic acid functional enhancers (and are thus formulated at lower pH) are polymers having sulfonic acid, sulfonate, phosphonic acid, or phosphate groups.

Associative Polymers. Associative polymers can be used to thicken the compositions of the present invention as well. Such polymers thicken at least in part as a result of hydrophobic or Van de Waals association of hydrophobic side chains. Such associative polymers can form viscous to gelled aqueous solutions despite their relatively low molecular weights. Polymers that are alcoholic soluble can be modified by the addition of a long chain hydrophobic group. A preferred class of such associative polymers is based on nonionic ethylenically unsaturated monomers wherein at least one comonomer has at least 12 and preferably at least 16 carbon atoms.

An example is cetyl hydroxyethylcellulose, available as NATROSOL PLUS from Aqualon, which utilizes an associative mechanism to enhance the viscosity it produces. Grafted side chains of cetyl alkyl groups can associate with neighboring alkyl hydrophobes. These interpolymer associations can dramatically increase the viscosification efficiency of the polymer. Longer chain alklyl, alkenyl, and aralkyl groups may also be suitable. For example, another preferred associative polymer is Arsitoflex HMB, which is ammonium acryloyldimethyltaurate/beheneth-25 methacrylate crosspolymer and is available from Clariant Corp.

(5) Neat Compositions: The antiseptic compositions of the present invention also may be delivered to the treatment site in a neat form or in a volatile solvent that rapidly evaporates to leave behind a neat composition. Such compositions may be solid, semi-solid or liquid. In the case where the compositions are solid, the antiseptic and/or the enhancer and/or the surfactant may optionally be microencapsulated to either sustain the delivery or facilitate manufacturing a powder that is easily delivered. Alternatively, the composition can be micronized into a fine powder without the addition of other components or it may optionally contain fillers and other ingredients that facilitate powder manufacture. Suitable powders include but are not limited to calcium carbonate, calcium phosphate, various sugars, starches, cellulose derivatives, gelatin, and polymers such as polyethylene glycols.

When hydrophobic antiseptics are used, a method for micronizing a hydrophobic agent may be used wherein the hydrophobic agent is dissolved in an effective amount of a first solvent that is free of polymer such as the method described in U.S. Pat. No. 6,746,635. The hydrophobic agent and the solvent form a mixture having a continuous phase. A second solvent and then an aqueous solution are introduced into the mixture. The introduction of the aqueous solution causes precipitation of the hydrophobic agent and produces a composition of micronized hydrophobic agent having an average particle size of 1 micron or less. The particle size for use in delivery to the nose or other tissue may be significantly larger to direct delivery to the proper site. For example, to deliver the antiseptic powder to the nose, nasal cavities, and/or throat without passing into the lungs, larger particles may be required.

Bioadhesive polymers optionally may be added to the neat compositions as well as the other physical forms. Numerous suitable bioadhesive polymers are discussed in WO 93/21906. Representative bioadhesive polymers of particular interest include bioerodible hydrogels described by H. S. Sawhney, C. P. Pathak and J. A. Hubell in Macromolecules, 1993, 26:581-587, polyhyaluronic acids, casein, gelatin, glutin, polyanhydrides, polyacrylic acid, alginate, chitosan, poly (methyl methacrylates), poly(ethyl methacrylates), poly butylmethacrylate), poly(isobutylmethacrylate), poly(hexlmethacrylate), poly(isodecl methacrylate), poly(lauryl methacrylate), poly(phenyl methacrylate), poly(methyl acrylate), poly(isopropyl acrylate), poly(isobutyl acrylate), and poly (octadecl acrylate). Preferred polymers are polyacrylic acid (e.g., Carbomer) and poly(fumaric-co-sebacic)acid. Other bioadhesive and bioerodible polymers are described in U.S. Pat. No. 6,746,635. Particularly preferred are slightly crosslinked polyacrylic acids such as those sold under the CARBOPOL brand by BF Goodrich.

The antimicrobial compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The neat antiseptic compositions according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch. Those of skill in the art can readily determine the various parameters and conditions for producing aerosols without resort to undue experimentation. Inhaled medications are preferred in some embodiments because of the direct delivery to the lung. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. Techniques for preparing aerosol delivery systems are well known to those of skill in the art. Generally, such systems should utilize components that will not significantly impair the biological properties of the agent (see, for example, Sciarra and Cutie, "Aerosols," in Remington's Pharmaceutical Sciences, 18th edition, 1990, pp. 1694-1712).

The compounds may also be formulated in rectal or vaginal compositions such as suppositories or retention enemas, e.g., containing conventional suppository bases such as cocoa butter or other glycerides.

Viscosity

The preferred compositions of the present invention have a viscosity of at least 500 Centipoise (cps) for ease of application topically. More preferably, compositions of the present invention have a viscosity of at least 1,000 cps, even more preferably at least 10,000 cps, even more preferably at least 20,000 cps, even more preferably at least 50,000 cps, even more preferably at least 75,000 cps, even more preferably at least 100,000 cps, and even more preferably at least 250,000 cps (and even as high as about 500,000 cps, 1,000,000 cps, or more). The viscosity can be measured as described below in the Viscosity Test. Preferred formulations have high viscosity even after application to mammalian tissue at 32-37° C. Because certain optional ingredients, such as enhancers, hydrophilic compounds, hydrophobic compounds, and the like, may affect the viscosity (either positively or negatively), the measured viscosity is that of the final composition.

Lower viscosity compositions can be used, however, in certain applications, such as for the treatment of middle ear infection and chronic sinusitis. For example, afflictions of the middle ear (e.g., otitis media or infection of the middle ear) may be treated with compositions of the present invention having a viscosity lower than 1000 cps more readily by administration through the outer ear or through the nose and into the Eustachian tubes. The viscosity is measured by the Viscosity Test described herein. Preferred compositions meet the above viscosity limitations even when warmed to 32° C. Most preferred compositions meet the above viscosity limitations even when warmed to 35° C.

Delivery Methods and Devices

Antimicrobial compositions of the present invention can be provided to a medical professional in a single composite formulation or in multiple parts. For example, a composition can be provided in two parts (e.g., in two separate containers or two separate compartments of the same container), one part containing the antiseptic component and one part containing the enhancer. Other components of the composition can be combined with either one of the two parts. Alternatively, the other components can be included in a third part.

Topical antimicrobial treatment regimens according to the practice of this invention include applying a safe and effective amount of the compositions described herein directly to the infected or at-risk skin, wound, or mucous membrane; particularly, the nasal nares and passages that are particularly susceptible to microbial contamination. The dose and frequency of application will depend on many factors including the condition to be treated, the concentration of antiseptic and optional enhancer, the microbe to be killed, etc. Typically, the compositions will be delivered in dosages of at least 10 mg per $cm^2$ of tissue, preferably 20 mg per $cm^2$ of tissue, more preferably at least 30 mg per $cm^2$ of tissue, and most preferably at least 50 mg per $cm^2$ of tissue for most applications. Application can be made once, or several (e.g., 2-4) times daily for one or more days. Typically, the composition is applied 1 or 2 times/day for 1-7 days. For example, decolonization of the anterior nares may require a dose of 0.25 gram (g) per nares applied 1-3 times per day for 1-5 days. Treatment of impetigo may require about 0.5 g/15 $cm^2$ (33 mg/$cm^2$) applied 1-3 times/day for 3-10 days.

Compositions of the present invention can be delivered using a variety of techniques. Typically, the compositions are delivered to the skin and/or mucosal tissue in a manner that allows them to penetrate into the skin and/or mucosal tissue, as opposed to through the tissue into the blood stream. This concentrates the compositions locally at the site in need of treatment. This delivery can be accomplished by spraying, dipping, wiping, dropping, pouring, toweling, inhaling, or the like, onto the area to be treated.

In the methods of the present invention, the antiseptic compositions may be provided as a formulation suitable for delivery to mammalian tissue (e.g., skin and/or mucosal surfaces). Suitable formulations can include, but are not limited to, creams, gels, foams, ointments, lotions, balms, waxes, salves, solutions, suspensions, dispersions, water-in-oil or oil-in-water emulsions, microemulsions, pastes, powders, oils, lozenges, boluses, and sprays, and the like.

The compositions may be sprayed from a pressurized container. The pressure may be supplied by an external means such as squeezing the container, through the use of a mechanical pump, or with the use of a propellant. Suitable propellants include chlorofluorocarbons (CFCs), hydrochlorofluorocarbons (HCFCs), hydrofluorocarbons (HFCs), hydrofluoroethers (HFEs), perfluorinated alkanes, and (C1-C5) alkanes as well as nitrous oxide and dimethyl ether.

If delivered as a foam, the composition may be dispensed from an aerating dispenser such as the F2 Finger Pump Foamer available from Air Spray International Pompano Beach, Fla. Alternatively, the foam may be generated using a suitable propellant such as those described above.

For very high viscosity formulations the composition may be delivered in essentially a solid dosage form by placing the composition in or on the tissue to be treated. For example, a small suppository type delivery could be placed into the anterior nares for eradication of *staphylococcus* sp.

Various other modes of administration can be used as well known to one of skill in the art depending on the desired location for contact of the antimicrobial compositions of the present invention. For example, afflictions of the middle ear (e.g., otitis media or infection of the middle ear) may be treated with compositions of the present invention by administration through the nose and into the Eustachian tubes or they can be instilled directly into the middle ear through the tympanic membrane. The formulations may traverse the tympanic membrane with the aid of a syringe or do so by diffusion. Penetration enhancers may be used to enhance diffusion across the tympanic membrane.

For application to skin or mucosal tissue, for example, the compositions may be applied directly to the tissue from a collapsible container such as a flexible tube, blow/fill/seal container, pouch, capsule, etc. In this embodiment, the primary container itself is used to dispense the composition directly onto the tissue or it can be used to dispense the composition onto a separate applicator. For example, for delivery to the nose or other topical tissue, the composition could be dispensed directly from a tube and spread by a number of means including squeezing the outside of the nose together repeatedly, wiping with the tip of the tube or with a separate device such as a spatula, cotton, rayon, or other natural or synthetic based fiber swab.

Other application devices may also be suitable including applicators with foam tips, brushes, and the like. Importantly, the applicator must be able to deliver the requisite amount of composition to the tissue. Therefore, in most instances applicator devices such as webs and swabs are coated on the applicator web at greater than 50% by weight of the dry web and preferably in excess of 100% by weight of the dry web (on a swab, this would include the weight only of the web).

The collapsible containers may be made in a number of single layer, laminate, or coextruded constructions. Materials of construction may include polyolefins such as low, medium or high density polyethylene including low and linear low density polyethylene, polypropylene, as well as copolymers of ethylene and/or propylene with other polar or non-polar comonomers; polyamides such as nylons, polyesters such as polyethylene terephalate, polybutyleneterephalate, polyethylenenaphthalate; polyurethanes, polyacrylates, and the like. In some constructions it may be desirable to include a barrier material to prevent evaporation of one or more components of the formulation. Suitable barrier materials include polyesters (e.g., polyethylene terephthalate, polyethylene naphthalate and polybutylene terephalate and the like), fluorinated layers such as polytetrafluoroethylene (PTFE, e.g., TEFLON), polyamides (e.g., nylon), chlorotriflouroethylene (ACLAR), polyvinylidene fluoride, as well as copolymers of perflourinated monomers with partially fluorinated monomers such as copolymers of tetraflouroethylene/hexafluoropropylene/vinylidene fluoride (THV Fluorothermoplastic from Dyneon Company), polyvinylchloride, polyvinylidene chloride (PVDC, e.g., SARAN HB), ethylene vinyl alcohol (EVOH), polyolefins (e.g., polyethylene, high density polyethylene, polypropylene, and combinations thereof). Oriented and biaxially oriented polymers may be particularly preferred.

Particularly preferred barrier constructions include metallic foil barriers such as aluminum foil laminates, HDPE, PET, PETG, PEN laminates of polyester and polyolefin (in particular PET/HDPE or HDPE/PET/HDPE), laminates of PET and EVOH, biaxially oriented nylon, PVDC, Nylon/EVOH/Nylon (OXYSHIELD OUB-R), chlorotrifluoroethylene and laminates thereof, ceramic layer including silicon oxide ($SiO_x$ where $x=0.5$-$2$ and preferably 1-2) coated thermoplastics, and ceramic coated PET (CERAMIS available from CCL Container/Tube Division, Oak Ridge, N.J.).

An antimicrobial composition may be applied to a mucosal surface with the use of a delivery device such as cervical caps, diaphragms and solid matrices such as tampons, cotton sponges, cotton swabs, foam sponges, and suppositories. Accordingly, compositions of the present invention can also be incorporated in (e.g., delivered from) cloth, sponges, paper products (e.g., paper towels, towelettes, and wipes), tampons, undercast padding, and dental floss, for example.

In some embodiments, an applicator may be used to place the device and/or antimicrobial composition in the proper location, for example, on the mucosal surface of a vagina, nasal cavity, rectum, or the like. Examples of such applicators include, for example, cardboard or plastic tube applicators commonly used for inserting tampons or suppositories.

The compositions of the present invention can be delivered from various substrates for delivery to the tissue. For example, the compositions can be delivered from a wipe or pad which when contacted to tissue will deliver at least a portion of the composition to the tissue. For application to nasal cavities the compositions may be provided by a nonwoven swab such as a "Q-tip" brand cotton swab, into a foam tip applicator, and the like. The substrate may be used to deliver the composition essentially instantaneously or may be left in contact with the tissue. For example, a substrate in a tubular form could be delivered to the anterior nares using a suitable applicator and left in the anterior nares. The annular nature of the device is designed to allow delivery of the active while allowing the patient to freely breath through the nose.

Also, compositions of the present invention can be coated onto medical devices that contact skin, mucous membranes, wounds, etc. Examples of such devices include catheters such as urinary tract catheters and vascular access catheters.

Objects and advantages of this invention are further illustrated by the following examples, but the particular materials and amounts thereof recited in these examples, as well as other conditions and details, should not be construed to unduly limit this invention.

TEST PROTOCOLS

Killing Microbes on Tissue

Many of the compositions of the present invention are intended to kill microorganisms on mammalian tissue such as skin and mucosal tissue. The extent of kill can be determined in the following manner. Subjects are identified who are naturally colonized with the microorganism of interest. This is preferred over methods where the tissue is artificially colonized with non-resident flora. For example, subjects may be identified whom are colonized with *staphylococcus aureus* (SA) in the anterior nares by swabbing the anterior nares and culturing the swab. This is normally repeated at least one additional time to ensure the subject is a "chronic carrier", i.e., one who carries the organism all or most of the time. A swab may also be taken several days prior to treatment to increase the probability that the subject is, in fact, a carrier. The subject is then treated with the indicated composition in a dose and at a frequency stated. The anterior nares once again are swabbed to determine if the bacteria has been reduced or eradicated (decolonized). Preferred formulations eradicate the SA in less than 72 hours, more preferably in less than 48 hours, and most preferably in 24 hours or less. On skin the procedure is similar except that a control site distinct from the treatment site may be selected on the treatment day. In this case, a log reduction may be determined. The procedure on skin is described in Federal Register, 21 CFR Parts 333 and 369, Tentative Final Monograph for Healthcare Antiseptic Drug Products; Proposed Rule, 1994 (scrub cup method). When performing this method on skin the antiseptic compositions are generally allowed to remain in contact with the skin for at least 6 hours under a suitable dressing such as Tegaderm (3M Company) to check for antimicrobial activity. Preferred formulations show at least 1 log reduction and preferably at least 1.5 log reduction in 6 hours on a dry skin site (e.g. the abdomen).

Antimicrobial Efficacy Test

This method tries to mimic the actual use conditions for many topical antiseptics. In most cases a topical antiseptic is applied to the area, optionally with some rubbing, and allowed to remain in contact and kill any microorganisms present in an essentially static state. In this assay, a composition is spread onto a film to form a uniform coating 10 mil (250 micron) thick, a suspension of bacteria are directly inoculated onto the surface of the composition, after a defined period of time, the inoculated disk is placed in a neutralizing broth, and at least a portion of this is diluted and plated to enumerate the surviving bacterial. It should be noted that just as in the in-vivo condition, this in-vitro method takes into account the ability of the formulation to be wet by tissue or the bacteria/bacterial suspension wetting. In certain compositions the bacterial suspension will wet the composition very well and spread. With other compositions the bacterial suspension may remain as discrete droplets. This is expected to simulate in-vivo performance in wetting tissue and bacterial biofilms. Since preferred compositions of the present invention are ointments this works very well. For less viscous compositions a compatible thickening agent should be incorporated to achieve a viscosity of at least 20,000 cps and preferably at least 50,000 cps.

For all antiseptics used in this assay an initial experiment was conducted to confirm that the neutralization broth was effective at neutralizing the antiseptic while not damaging the microorganisms. In general, to confirm neutralization, 100 µL of inoculum (target organism concentration of 10-100 CFU/mL) was added to 20 mL (for DE neutralizer) or 100 mL (for the Sampling Solution) of warmed (36° C.) neutralizer broth, vortexed, and a sample disk with ointment was dropped into the broth (time zero, t0) and the tube mixed vigorously. This was done using a vortex mixer for the 20 mL samples and by hand shaking for the 100 mL samples. 1 mL aliquots in duplicate were pour plated at three time points: 1) immediately (<1 minute), 2) at 30 minutes, and 3) at 60 minutes post-inoculation (all at room temperature). Plating was done using tryptic soy agar (TSA). Plates were incubated at 36° C. for up to 48 hours. Plates were enumerated and CFU/mL calculated. The data was converted to $\log_{10}$ CFU/mL. Both test samples and a numbers control were run. The numbers control consisted of 100 µL of inoculum added to 20 mL PBW (phosphate buffered water, PBW) to yield an organism concentration of 10-100 CFU/mL. The PBW was prepared as follows: A stock solution was prepared by dissolving 34 g potassium dihydrogenphosphate in 500 mL deionized water. This was adjusted to pH 7.2 using 10N sodium hydroxide and then diluted with deionized water to make exactly 1 liter. The stock solution was filter sterilized and dispensed into a sterile bottle and refrigerated. The PBW was prepared by adding 1.25 mL stock solution to 1 liter deionized water and steam sterilized at 121° C. for 25 minutes. After sterilization, the solution was mixed by swirling to ensure uniformity. A toxicity control was also run by adding 100 µL of inoculum to 20 mL neutralizer broth to yield an organism concentration of 10-100 CFU/mL.

Neutralizer Effectiveness: If the $\log_{10}$ CFU/mL of the test sample is not more than 0.3 log less than the corresponding Numbers Control, the neutralization will be considered effective.

Neutralizer Toxicity: If the Toxicity Control (TC) is not more than 0.3 log less than the corresponding Numbers Control sample, the sampling solution will be considered non-toxic.

Test Organisms for Antimicrobial Efficacy Test

The test organisms for this assay were methicillin resistant *Staphylococcus aureus*, ATCC 33953 and *E. coli*, ATCC 11229. The initial suspension was prepared by suspending bacterial colonies from overnight growth plates in phosphate-buffered water (PBW). A 0.5 McFarland turbidity standard was used to obtain a cell density of approximately $1.0 \times 10^8$ CFU/mL.

Test Materials for Antimicrobial Efficacy Test

The samples for this assay were spread at room temperature to a uniform thickness of 10 mil (250 µm) using a laboratory knife coater onto a 100 µm thick biaxially oriented clean and 70 wt-% isopropanol sanitized polyesterterephthalate (PET) film. These coated samples were placed in sterile Petri dishes and sealed with Parafilm to prevent evaporation and preserve cleanliness. Bubbles in the formulation were minimized as much as possible. Spread samples containing any volatile solvents such as water were used within 24 hrs of spreading. Test samples were cut from the same PET coated films using a 70 wt-% isopropyl alcohol (IPA) disinfected 23 mm die, as described in the next section. The sample disks were stored in sterile Petri dishes until testing.

Neutralizing Broth: The DE broth was Dey Engle broth purchased as a solid and reconstituted according to directions from Difco Laboratoris, Detroit, Mich. The DE broth was used for all the antiseptics of this invention, except those examples containing triclosan. The Sampling Solution (below) was used to neutralize the examples containing triclosan. Sampling Solution:

| Component | Concentration (g/liter) | Purchased from |
| --- | --- | --- |
| Tween 80 | 90.0 | Sigma Aldrich |
| Lecithin | 10 | Fisher Scientific Company (vegetable derived, 03376-250) |
| Potassium dihydrogen phosphate | 0.40 | Sigma Aldrich |
| Disodiumhydrogen phosphate | 10.1 | Sigma Aldrich |
| Triton X-100 | 1.0 | Sigma Aldrich |
| Water | 888.5 | |

Inoculum Preparation for Antimicrobial Efficacy Test

The inoculum was serially diluted with phosphate buffered water (PBW) 10,000 fold ($10^{-4}$) to achieve a concentration of $1\text{-}5 \times 10$ CFU/mL. The inoculum suspension was enumerated at the beginning and end of the test period. The final count was within 0.1 log/mL of the initial count. Each disk was inoculated with between $10^{6.5}$ and $10^{7.5}$ bacteria.

Measurement of Antimicrobial Activity:

After first confirming neutralization, samples were tested for antimicrobial activity using an in vitro model that attempts to simulate in-use conditions. Using aseptic technique and steam sterilized materials (except for the ointments), 23 mm disks of each formulation were cut using a 70 wt-% IPA-disinfected 23 mm die. Two bacteria were tested: *Staphylococcus aureus* (MRSA 33953) and *E. coli* ATCC 11229. Each inoculum was prepared by suspending bacterial colonies from overnight growth plates in phosphate-buffered water (PBW). A 0.5 McFarland turbidity standard was used to obtain a cell density of approximately $1.0 \times 10^8$ CFU/mL. 50 µL of the inoculum was rapidly spotted on the surface of the test ointment (in 8-12 tiny droplets). After the last drop was applied the bacteria were allowed to remain in contact with the ointment for the specified period of time (e.g., 2.5 and 10 minutes). At the end of the exposure time (time bacteria are in contact with the composition) the inoculated disk was dropped into warm (36° C.) Neutralizer Broth (20 mL for DE and 100 mL for Sampling Solution) and mixed vigorously (vortexed using a VWR Vortex Genie 2) for 2 minutes for DE. Two one-hundred fold dilutions were prepared in Neutralizer Broth, and the bacteria enumerated using the pour plate. Plates were incubated at 36° C. for up to 48 hours. Colony Forming Units (CFUs) were counted.

The CFUs for each plates were multiplied by the dilution factor to arrive at CFU/mL, and converted to log10 CFU/sample. Log10 CFU/samples of duplicate tests were averaged and the log10 reduction was calculated. Log reductions were calculated by subtracting the log10 bacterial recovery of the test materials from the log10 bacterial recovery of the control (100 µL of inoculum in 20 mL warm D/E neutralizing broth or 100 µL in 100 mL of Sampling Solution or 100 µl in 100 mL of Sampling Solution).

The compositions of the present invention were analyzed for their ability to kill MRSA and *E. coli* at 2.5 and 10 minutes. By comparison Bactroban Nasal ointment in this assay showed essentially no kill of this strain of MRSA at 2.5 min. (The log reduction values were 0.030 and −0.040.) In fact, Bactroban Nasal showed essentially no kill after contact for 2 hours. It is a significant advantage that the compositions of the present invention are able to kill microorganisms rapidly. Preferred compositions achieve a at least a 1.5 log reduction in 10 minutes, more preferably at least a 2 log reduction in 10 minutes, and most preferably at least a 3 log reduction in 10 minutes. Particularly preferred compositions of the present invention achieve at least a 1.5 log reduction in 2.5 minutes, more preferably at least a 2 log reduction in 2.5 minutes, and most preferably at least a 3 log reduction in 2.5 minutes for at least one of the two test organisms. Most preferred formulations achieve these log reduction values for both test organisms.

Viscosity Test

For selected Examples viscosity was measured at approximately 22° C. at ambient pressure using a Brookfield LVDV-I+ viscometer equipped with a model D Brookfield heliopath and LV spindles. The spindle and speed was chosen for each particular sample such that the viscometer was operating in the middle of its range. All samples were allowed to equilibrate at approximately 22° C. for 24 hours prior to measurement. Preferably the viscosity is taken at the lowest speed possible while staying within 20-80% of the viscometer range and more preferably between 30-70% of the range. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles.

EXAMPLES

TABLE 1

| Glossary of Components | | | | |
|---|---|---|---|---|
| Acronym | Trade name | Description | Source | Address |
|  | 2-phenoxyethanol | 2-phenoxyethanol | Aldrich | Milwaukee, WI |
|  | Emulsifying polymer GG | 80/20 IOA/MPEG (25 wt-% polymer in IPP) | Prepared as described below* | St. Paul, MN |
| DOSS | Aerosol OT-75 | docusate sodium | American Cyanamid | W. Patterson, NJ |
|  | benzalkonium chloride | benzalkonium chloride | Aldrich | Milwaukee, WI |
|  | Carbowax 400 | Polyethyleneglycol 400 | DOW/Union Carbide | Danbury, CT |
|  | Carbowax 1450 | Higher MW PEG, e.g. 1450 | DOW/Union Carbide | Danbury, CT |
| DOSS | Complemix | docusate sodium USP | ICI Americas | Wilmington, DE |
| EDTA | EDTA disodium | ethylene diamine tetraacetic acid, disodium | Aldrich | Milwaukee, WI |
|  | glycerin (glycerol) | glycerin (glycerol) | Aldrich | Milwaukee, WI |
|  | Hipure 88 | lactic acid (88 wt-%) in water | Purac America | Lincolnshire, IL |
|  | Incroquat Behenyl TMS | Cationic emulsifying wax | Croda | Parsippany, NJ |
|  | Irgasan DP300 | Triclosan | Ciba | Tarrytown, NY |
|  | Lurol ASY | alkyl phosphate | George A. Goulston | Monroe, NC |
|  | Mineral oil | Mineral oil USP | Paddock Labs | Minneapolis, MN |
| PCMX | Ottasept | Parachlorometaxylenol | Lonza/Happi | Ramsey, NJ |
|  | Pluronic P-65 | Nonionic difunctional block copolymer | BASF | Mount Olive, NJ |
|  | Polawax | Emulsifying wax, cetearyl alcohol + ceteareth 20 | Croda | Parsippany, NJ |
| NaOH | Sodium hydroxide | 10 N NaOH | Sigma Aldrich | Milwaukee, WI |
|  | Snow White | White Petrolatum USP | Penreco | Karns City, PA |

*Emulsifying polymer GG was prepared in the following manner. A mixture of isooctyl acrylate (IOA, 21.6 parts), and MPEG (5.4 parts) [80/20 IOA/MPEG, respectively, weight ratio] was dissolved in ethyl acetate (33 parts) that containedVAZO 67 radical initiator (0.081 part). The solution was contained in a flint glass bottle that was closed with a Teflon-lined metal cap and maintained at 65° C. for 50 hours. Monomer conversion (determined by percent solids measured by loss on dryingat 105° C.) was essentially complete at 50 hours. Solvent exchange was accomplished by adding isopropyl palmitate (IPP) to the ethyl acetate solution and stripping the lower boiling ethyl acetate on a ROTOVAP evaporator to obtain a 25 weight percent solutionof polymer in IPP.

PREPARATION OF EXAMPLES

Samples of 250 grams were prepared according to the procedures listed below. The samples were tested according to the Antimicrobial Efficacy test against both MRSA and *E. coli* at 2.5 minutes and 10 minutes.

Control Examples C1 & C2

Control compositions of 250 grams each, containing no antimicrobial agents, were prepared using the components shown in Table 2a for each example. Carbowax 1450 PEG was heated in an oven until melted in a first glass container. In a second glass container Glycerin, Carbowax 400 and Aerosol OT-75 DOSS were also heated to 70° C. Contents of the second container were added to the first container, swirled by hand to mix and reheated to 70° C. The composition was removed from the oven and allowed to cool to at least approximately 40° C., while mixing on a roller.

Examples 1-5

Antimicrobial compositions of 250 grams each was were prepared using the components shown in Table 2a. The respective antimicrobials: PCMX, Irgasan DP300 (triclosan), or benzalkonium chloride; were combined with other components: glycerin, Carbowax 400 and Aerosol OT-75 in a glass container and heated in an oven at approximately 70° C. Carbowax 1450 PEG was placed in a second glass container heated to its melting point and then added to the first container. The composition was then swirled by hand to mix and then reheated again to 70° C. The composition was allowed to cool on rollers to approximately 40° C. then transferred into jars, and sealed.

The control samples showed no antimicrobial efficacy in 2.5 min against the test organisms. These examples, prepared in hydrophilic vehicles, had 2.9 log or greater kill in 2.5 minutes for both MRSA (Gram positive) and *E. coli* (Gram negative) bacteria. Addition of a lactic acid enhancer to Example 5 improved the antimicrobial efficacy against *E. coli* by greater than 3.7 log when compared to Example 4. Example 5 showed complete kill of *E. coli*. A combination of a quaternary ammonium compound (benalkonium chloride) with triclosan at a significantly reduced concentration in Example 3 still provided 3.9 log kill against MRSA in 2.5 minutes and 5.2 log kill against *E. coli* in 2.5 min.

Examples C3, C4, 6-9

Control Examples C3 and C4, containing no antimicrobial agents, as well as antimicrobial compositions, Examples 6-10, were prepared in amounts of 250 grams each using the components shown in Table 2b for each example. Petrolatum was added to a glass container and heated in an oven to approximately 70° C. All other components were added to a second glass container and also heated in an oven at approximately 70° C. Just prior to mixing the contents of the two containers together, Aerosol OT75 (where applicable) was first added to the second container. The mixture of all components was then mixed using a high shear rotor/stator Silverson homogenizer on high speed for 1 minute. Mixing was continued at low speed using a Gast overhead air mixer with radial flow impeller until just before the composition congealed at approximately 40° C. The compositions were removed from the mixer, poured into jars, and sealed.

Examples 6 and 7 are compositions having a hydrophobic vehicle, with a hydrophilic component and a surfactant. Example 6 had greater than 4.5 log kill efficacy against both MRSA and *E. coli* at 2.5 min and Example 7 had greater than 4 log kill efficacy against MRSA at 10 min. Example 9 had an additional alphahydroxy acid enhancer, which improved the antimicrobial efficacy against MRSA at both 2.5 and 10 minutes. Examples 3C and 4C are controls which indicate the compositions without triclosan had less than 2 log kill against MRSA and *E. coli* at 10 min.

Example 10

Example 10, also shown in Table 2b, was prepared in the same manner as Examples 6-9, except the Irgasan DP300 (triclosan) was added to the Petrolatum prior to heating. Example 10 contains no glycerin (hydrophilic) component and did not achieve 2 log kill. Example 7, which had a similar composition to Example 10, did contain glycerin and as mentioned above, Example 7 had greater than 4 log kill efficacy against MRSA at 10 min.

Examples 11-15

An antimicrobial composition of 250 grams was prepared using the components shown in Table 2c for each example. Irgasan DP300, Hipure 88 (lactic acid) and glycerin were added to a first glass container and heated to 70° C. in an oven. Polawax, mineral oil, Incroquat Behenyl TMS, 2-pheoxyethanol, lactic acid, EDTA, Complemix, Aerosol OT-75 and Pluronic P-65 were added to a second glass container and also heated to 70° C. in an oven. Water was heated in the oven to 70° C. in a third glass container. The water was then added to the second container and mixed using a high shear rotor/stator Silverson homogenizer on high speed for 1 minute. The contents of the first container were then added to the new mixture of the second container and again mixed using a high shear rotor/stator Silverson homogenizer on high speed for 1 minute. The composition was allowed to cool on rollers to approximately 40° C. Example 11 is an oil in water emulsion containing triclosan which did not achieve 2 log kill at 10 minutes for either MRSA or *E. coli*. As shown in Example 12, addition of an anionic surfactant (DOSS), however, improved the antimicrobial efficacy to 5.3 log against MRSA at 10 minutes. Addition of both an anionic surfactant (DOSS) and an enhancer (lactic acid) improved the antimicrobial efficacy for Example 13 to greater than 7 log at 10 min against MRSA. In Example 14, addition of a chelator (EDTA, 14800 μM), even in the absence of an anionic surfactant, improved the antimicrobial efficacy against MRSA to 4.7 log at 10 minutes. Example 15 had no 2-phenoxyethanol enhancer and did not achieve a 2 log kill at 10 minutes against either MRSA or *E. coli*.

Component Composition of Examples:

Tables 2a, 2b and 2c show the weight/weight % concentration of each component in each example composition as well as the antimicrobial efficacy results.

TABLE 2a

| | Example Numbers | | | | | | |
| --- | --- | --- | --- | --- | --- | --- | --- |
| | C1 | C2 | 1 | 2 | 3 | 4 | 5 |
| Component | | | w/w % amount of components | | | | |
| Ottasept (PCMX) | — | — | 2.00 | — | — | — | — |
| 2-phenoxyethanol | — | — | 0.50 | 0.50 | — | 0.50 | 0.50 |
| Irgasan DP300 | — | — | — | 2.00 | 0.50 | 2.00 | 2.00 |
| Benzalkonium Chloride | — | — | — | — | 0.13 | — | — |
| Hipure 88 (lactic acid) | — | — | — | — | — | — | 1.00 |
| Carbowax 400 | 61.78 | 60.96 | 59.00 | 59.00 | 58.00 | 59.22 | 58.79 |
| Carbowax 1450 | 16.75 | 16.53 | 16.00 | 16.00 | 17.00 | 16.20 | 15.96 |

TABLE 2a-continued

| Component | C1 | C2 | 1 | 2 | 3 | 4 | 5 |
|---|---|---|---|---|---|---|---|
| | | | w/w % amount of components | | | | |
| Glycerin | 21.47 | 21.18 | 20.50 | 20.50 | 20.00 | 20.75 | 20.42 |
| Aerosol OT-75 (DOSS) | — | 1.33 | 2.00 | 2.00 | — | 1.33 | 1.33 |
| Pluronic P-65 | — | — | — | — | 4.37 | — | 0.00 |
| Total | 100.0 | 100.0 | 100.0 | 100.0 | 100.0 | 100.0 | 100.0 |
| Antimicrobial efficacy results: | | | | | | | |
| 2.5 min MRSA test 1 | −0.8 | −0.2 | 6.6* | 3.3 | 3.4 | 6.8* | 5.8 |
| 2.5 min MRSA test 2 | −0.8 | −0.3 | 6.6* | 2.6 | 4.3 | 6.8* | 5.8 |
| Average | −0.8 | −0.3 | 6.6* | 2.9 | 3.9 | 6.8* | 5.8 |
| 2.5 min E coli test 1 | −0.5 | 0.1, 0.9 | 4.7 | 4.2 | 4.5 | 3.1 | 6.9* |
| 2.5 min E coli test 2 | −0.5 | 0.1, 0.7 | 4.0 | 4.1 | 5.9 | 3.3 | 6.9* |
| Average | −0.5 | 0.5** | 4.4 | 4.1 | 5.2 | 3.2 | 6.9* |

*Complete Kill.
**Average of 2 sets of 2 results.

No testing performed at 10 minutes for MRSA or E. coli.

TABLE 2b

| Component | 3C | 4C | 6 | 7 | 8 | 9 | 10 |
|---|---|---|---|---|---|---|---|
| | | | w/w % amount of components | | | | |
| 2-phenoxyethanol | 0.50 | — | 0.50 | 0.50 | 0.50 | 0.50 | 0.50 |
| Irgasan DP300 | — | — | 2.00 | 2.00 | 2.00 | 2.00 | 2.00 |
| Hipure 88 (lactic acid) | 1.00 | 1.00 | — | — | — | 1.00 | — |
| Glycerin | 20.00 | 20.00 | 10.00 | 20.00 | 20.00 | 20.00 | — |
| Snow White | 75.17 | 75.67 | 81.20 | 76.17 | 77.50 | 73.17 | 96.17 |
| Complemix (DOSS) | 1.33 | 1.33 | — | — | — | — | — |
| Aerosol OT-75 (DOSS) | — | — | 1.30 | 1.33 | — | 1.33 | 1.33 |
| Pluronic P-65 | 2.00 | 2.00 | 5.00 | — | — | 2.00 | — |
| Water | — | — | — | — | — | — | — |
| Total | 100.0 | 100.0 | 100.0 | 100.0 | 100.0 | 100.0 | 100.0 |
| Antimicrobial efficacy results: | | | | | | | |
| 2.5 min MRSA test 1 | 0.8 | 1.6 | 4.2 | −0.8 | 0.0 | 2.2 | −1.6 |
| 2.5 min MRSA test 2 | 0.7 | 1.8 | 4.8 | 0.5 | −0.9 | 3.6 | −1.7 |
| Average | 0.8 | 1.7 | 4.5 | −0.2 | −0.5 | 2.9 | −1.6 |
| 2.5 min E coli test 1 | NT | NT | 5.6 | 0.2 | 0.1 | 0.7 | 0.0 |
| 2.5 min E coli test 2 | NT | NT | 5.3 | 0.2 | −0.2 | 1.3 | 0.0 |
| Average | — | — | 5.5 | 0.2 | −0.1 | 1.0 | 0.0 |
| 10 min MRSA test 1 | 1.6 | 1.7 | NT | 4.9 | 0.3 | 4.6 | 0.9 |
| 10 min MRSA test 2 | 1.4 | 1.7 | NT | 3.3 | 0.4 | 6.8 | 0.0 |
| Average | 1.5 | 1.7 | — | 4.1 | 0.3 | 5.7 | 0.5 |
| 10 min E coli test 1 | −0.7 | −0.7 | NT | 0.9 | 0.4 | 1.2 | 0.2 |
| 10 min E coli test 2 | −0.7 | 0.1 | NT | 1.0 | 0.3 | 1.1 | −0.4 |
| Average | −0.7 | −0.3 | — | 0.9 | 0.4 | 1.1 | −0.1 |

TABLE 2c

| Component | 11 | 12 | 13 | 14 | 15 |
|---|---|---|---|---|---|
| | w/w % amount of components | | | | |
| 2-phenoxyethanol | 0.50 | 0.50 | 0.50 | 0.50 | — |
| Irgasan DP300 | 2.00 | 2.00 | 2.00 | 2.00 | 2.00 |
| Hipure 88 (lactic acid) | — | — | 1.00 | — | — |
| EDTA disodium | — | — | — | 0.50 | — |
| Glycerin | 20.00 | 20.00 | 20.00 | 20.00 | 20.00 |
| Polawax | 10.00 | 12.00 | 12.00 | 12.00 | 12.00 |
| Incroquat Behenyl TMS | 3.00 | — | — | — | — |
| Mineral oil | 5.00 | 5.00 | 5.00 | 5.00 | 5.00 |
| Complemix (DOSS) | — | — | — | 1.00 | 1.00 |
| Aerosol OT-75 (DOSS) | — | 1.33 | 1.33 | — | — |
| Water | 59.50 | 59.17 | 58.17 | 59.00 | 60.00 |
| Total | 100.0 | 100.0 | 100.0 | 100.0 | 100.0 |
| Antimicrobial efficacy results: | | | | | |
| 2.5 min MRSA test 1 | −0.4 | 0.4, 4.3, 0.3 | 1.5 | 1.0 | 0.3 |
| 2.5 min MRSA test 2 | −0.6 | 0.5, 2.9, 0.3 | 2.4 | 1.94, 0.2 | 0.6 |
| Average | −0.5 | 1.5*** | 1.9 | 1.1 # | 0.4 |
| 2.5 min E coli test 1 | 0.3 | 0.2 | 0.0 | 1.0 | 0.6 |

TABLE 2c-continued

|  | Example Numbers | | | | |
| --- | --- | --- | --- | --- | --- |
|  | 11 | 12 | 13 | 14 | 15 |
| Component | w/w % amount of components | | | | |
| 2.5 min E coli test 2 | 0.3 | 0.1 | 0.1 | 0.7 | 0.1 |
| Average | 0.3 | 0.2 | 0.0 | 0.8 | 0.4 |
| 10 min MRSA test 1 | 0.7 | 5.1 | 7.2 | 3.6 | 0.3 |
| 10 min MRSA test 2 | 1.4 | 5.5 | 7.2 | 5.8 | 0.8 |
| Average | 1.1 | 5.3 | 7.2 | 4.7 | 0.5 |
| 10 min E coli test 1 | −0.5 | 0.6 | 2.8 | 0.9 | NT |
| 10 min E coli test 2 | 0.2 | −0.5 | 2.9 | 0.9 | NT |
| Average | −0.2 | 0.0 | 2.9 | 0.9 | — |

\*\*\*Average of 3 sets of 2
\#Average of 3 results

Subject Acceptability of Placebo—First Panel Evaluation

A panel of 10 normal healthy volunteers of either gender over 18 years of age evaluated a component composition without active antiseptic to determine acceptability and to develop evaluation methodology for future evaluations.

The compositions evaluated are shown in Table 3.

TABLE 3

| | Components (weight percent) | | | | | |
| --- | --- | --- | --- | --- | --- | --- |
| Composition | Lactic Acid USP | Glycerin USP | Docuate sodium USP (50%) | White petrolatum USP | PEG 400 NF | PEG 3350 NF |
| W | 1.00 | 10.00 | 2.00 | 87.00 | 0.00 | 0.00 |
| X | 1.00 | 20.00 | 2.00 | 0.00 | 59.00 | 18.00 |

Test Procedure

A dose was 0.5 mL of Composition W or X applied using a preloaded 1 mL plastic syringe. The volunteers applied the first dose after viewing a demonstration of the technique. The volunteers applied a second and third dose during Day 1.

One-half of the volunteers (5) were dosed with Composition W and one-half of the volunteers were dosed with Composition X on Day 1 and given a Rhinoscopic Examination of Nares before and after application on Day 1 and after 24 hours on Day 2. On Day 8 those volunteers dosed with Composition W on Day 1 received Composition X and those dosed with Composition X on Day 1 received Composition W. They were given a Rhinoscopic Examination of Nares before and after application on Day 8 and after 24 hours on Day 9.

Volunteers completed a questionnaire on Day 1 and on Day 9.

Results:

All 10 volunteers successfully completed both periods of the study. Descriptive analysis was provided for each categorical variable in the study.

Composition W was preferred by 10/10 of the volunteers. Five of ten volunteers could not complete all three application of Composition X. They cited stinging, burning and runny noses as primary reasons. Composition X caused more rhinorrhea than Composition W. Volunteers using Composition X felt they could use the ointment for a shorter period of time than with Composition W. Composition W could be felt to remain in the nasal vestibule longer (mean 218 minutes) than Composition X (mean 145 minutes).

Subject Acceptability of Placebo—Second Panel Evaluation

A second panel evaluation was done to determine acceptability of essentially anhydrous ointments based hydrophobic vehicles containing lactic acid or mandelic acid. The criteria for the panel were the same as for the first panel. The compositions evaluated are given in Table 4.

TABLE 4

| | Components (weight percent) | | | | |
| --- | --- | --- | --- | --- | --- |
| Composition | Lactic Acid USP | Mandelic Acid | DOSS USP (50%) | Glycerin USP | White petrolatum USP |
| Y | 1.00 | 0.00 | 2.00 | 10.00 | 87.00 |
| Z (emulsion) | 0.00 | 1.00 | 2.00 | 10.00 | 87.00 |

The test procedure was the same as that used for the first panel except a cotton swab was used to apply the composition rather than a tube.

Results:

Both ointments were acceptable with minimal, if any, side effects. The preference for the two ointments was fairly equally divided. Four of ten volunteers expressed a slight preference for the mandelic acid composition, three of ten volunteers expressed a slight preference for the lactic acid composition, and three of ten volunteers noticed no difference between the compositions.

Each volunteer applied 0.5 mL of composition; however, approximately 0.1 gram was routinely left on the swab. Therefore the dose was about 0.2 mL per nares. The time that the ointments remained in the volunteers' noses varied between volunteers, but there were indications that the ointment remained in place up to 24 hours. Two volunteers reported that the ointment appeared to accumulate from application to application.

The feel of the ointment in the nose and smell were the most noticed characteristics of both ointments, but the characteristics were all in the acceptable range.

Viscosity Test Results

The viscosity test results of select examples are shown in Table 5. These were tested at approximately 22° C. (72° F.) in accordance with the Viscosity Test.

TABLE 5

| Example No. | Viscosity cP × 1000 |
| --- | --- |
| C1 | 60 |
| C2 | 70 |
| 4 | 68 |
| 5 | 100.6 |
| 10 | 1088 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of killing or inactivating microorganisms on mammalian tissue, the method comprising contacting the affected area with an antimicrobial composition, the antimicrobial composition comprising:

an antiseptic selected from the group consisting of diphenyl ethers, halogenated phenols, bisphenols, halogenated carbanilides, salicylanilides, and combinations thereof, wherein the composition includes a total amount of the antiseptic of at least 1 wt-% and no greater than 6 wt-%, based upon the total weight of the composition as used, a hydrophilic component selected from the group consisting of polyhydric alcohols, lower alkyl ethers, and short chain esters; wherein the hydrophilic component is present in a total amount of at least 8 wt-% and no greater than 50 wt-%, based on the weight of the ready to use composition;

a surfactant selected from a sulfonate surfactant, a sulfate surfactant, a phosphate surfactant, and mixtures thereof; wherein the surfactant is present in a total amount of at least 0.5 wt-% and no greater than 3 wt-%, based on the weight of the ready to use composition; and a hydrophobic component wherein the hydrophobic component has a solubility in water of less than 1% by weight at 23° C.; and wherein the hydrophobic component is present in a total amount of at least 30 wt-%, based on the weight of the ready to use composition;

wherein the composition has a viscosity of greater than 100 cps;

wherein the mammalian tissue is at least a portion of the nasal cavity, the anterior nares, the esophageal cavity, and/or the nasopharynx of a subject;

wherein the microorganisms comprise bacteria and the antimicrobial composition is used in an amount effective to kill one or more bacteria.

2. The method of claim 1, further comprising an enhancer component.

3. The method of claim 2 wherein the enhancer component comprises an alpha-hydroxy acid, a beta-hydroxy acid, a chelating agent, a (C1-C4)alkyl carboxylic acid, a (C6-C12) aryl carboxylic acid, a (C6-C12)aralkyl carboxylic acid, a (C6-C12)alkaryl carboxylic acid, a phenolic compound, a (C1-C10)alkyl alcohol, an ether glycol, or combinations thereof.

4. The method of claim 2, wherein the enhancer component is present at a concentration greater than 0.2% by weight.

5. The method of claim 4 wherein the total concentration of the enhancer component relative to the total concentration of antimicrobial is within a range of 5:1 to 1:10, on a weight basis.

6. The method of claim 1 wherein the total concentration of the surfactant to the total concentration of antimicrobial is within a range of 3:1 to 1:10, on a weight basis.

7. The method of claim 1 wherein the hydrophilic component is present in an amount no greater than 30 wt-%.

8. The method of claim 1 wherein the hydrophobic component is present in an amount of at least 50 wt-%.

9. The method of claim 1 wherein the hydrophilic component is selected from a glycol, a lower alcohol ether, a short chain ester, or combinations thereof, and wherein the hydrophilic component is soluble in water in an amount of at least 20 wt-% at 23° C.

10. The method of claim 1 wherein the hydrophobic component is an organic compound, which at 23° C. is a liquid, gelatinous, semisolid, or solid and has a solubility in water of less than 0.5% by weight.

11. The method of claim 1, wherein the composition achieves at least 2 log reduction in test bacteria in 10 minutes according to the Antimicrobial Efficacy Test.

12. The method of claim 1 wherein the composition achieves at least 4 log reduction in test bacteria in 10 minutes according to the Antimicrobial Efficacy Test.

13. The method of claim 1 wherein the viscosity of the composition is at least 500 cps.

14. The method of claim 1 wherein the bacteria comprise *Staphylococcus* spp., *Streptococcus* spp., *Escherichia* spp., *Enterococcus* spp., *Pseudomonas* spp and combinations thereof.

15. The method of claim 14 wherein the bacteria comprise *Staphylococcus aureus, Staphylococcus epidermidis, Escherichia coli, Pseudomonas aeruginosa, Streptococcus pyogenes* and combinations thereof.

16. The method of claim 1 wherein the antiseptic is present in a concentration of at least 75% of the solubility limit of the antiseptic in the hydrophobic component.

17. The method of claim 1, wherein the hydrophilic component is present in the greatest amount.

18. The method of claim 1, wherein the hydrophobic component is present in the greatest amount.

19. A method of killing or inactivating microorganisms on mammalian tissue, the method comprising contacting the affected area with an antimicrobial composition,
 wherein water is not used in the composition, and
 the antimicrobial composition comprises:
 an antiseptic in an amount of at least 1 wt % and no greater than 6 wt-%, based upon the total weight of the composition as used, selected from the group consisting of diphenyl ethers, halogenated phenols, bisphenols, halogenated carbanilides, salicylanilides, and combinations thereof, a hydrophilic component selected from the group consisting of polyhydric alcohols, lower alkyl ethers, and short chain esters; wherein the hydrophilic component is present in a total amount of at least 8 wt-% and no greater than 50 wt-%, based on the weight of the ready to use composition;

a surfactant selected from a sulfonate surfactant, a sulfate surfactant, a phosphonate surfactant, a phosphate surfactant, a poloxamer, a cationic surfactant, and mixtures thereof; wherein the surfactant is present in a total amount of at least 0.5 wt-% and any surfactant irritating to tissue is present at no greater than 3 wt-%, based on the weight of the ready to use composition; and a hydrophobic component wherein the hydrophobic component has a solubility in water of less than 1% by weight at 23° C.; and wherein the hydrophobic component is present in a total amount of at least 30 wt-%, based on the weight of the ready to use composition;

wherein the composition has a viscosity of greater than 100 cps;

wherein the mammalian tissue is at least a portion of the nasal cavity, the anterior nares, and/or the nasopharynx of a subject;

wherein the microorganisms comprise bacteria and the antimicrobial composition is used in an amount effective to kill one or more bacteria.

20. The method of claim 19 wherein the composition includes an enhancer component, which is present at a concentration of greater than 0.2% by weight.

21. A method of killing or inactivating microorganisms on mammalian tissue, the method comprising contacting the affected area with an antimicrobial composition, the antimicrobial composition comprising:
 an antiseptic selected from the group consisting of diphenyl ethers, halogenated phenols, bisphenols, halogenated carbanilides, salicylanilides, and combinations thereof, wherein the composition includes a total amount of the antiseptic of at least 1 wt-% and no greater than 6 wt-%, based upon the total weight of the composition as used, a hydrophilic component selected from the group consisting of polyhydric alcohols, lower alkyl ethers, and short chain esters; wherein the hydrophilic component is present in a total amount of at least 8 wt-% and no greater than 50 wt-%, based on the weight of the ready to use composition;

a surfactant selected from a sulfonate surfactant, a sulfate surfactant, a phosphate surfactant, and mixtures thereof; wherein the surfactant is present in a total amount of at least 0.5 wt-% and no greater than 3 wt-%, based on the weight of the ready to use composition;

a hydrophobic component; wherein the hydrophobic component has a solubility in water of less than 1% by weight at 23° C.; and wherein the hydrophobic component is present in a total amount of at least 30 wt-%, based on the weight of the ready to use composition; and an enhancer component;

wherein the enhancer component is present in the composition at a concentration greater than 0.2% by weight;

wherein the composition has a viscosity of greater than 100 cps;

wherein the mammalian tissue is at least a portion of the nasal cavity, the anterior nares, and/or the nasopharynx of a subject;

wherein the microorganisms comprise bacteria and the antimicrobial composition is used in an amount effective to kill one or more bacteria.

22. A method of killing or inactivating microorganisms on mammalian tissue, the method comprising contacting the affected area with an antimicrobial composition and allowing it to remain on the tissue, the antimicrobial composition comprising:

an antiseptic selected from the group consisting of diphenyl ethers, halogenated phenols, bisphenols, halogenated carbanilides, salicylanilides, and combinations thereof, wherein the composition includes a total amount of the antiseptic of at least 1 wt-% and no greater than 6 wt-%, based upon the total weight of the composition as used, a hydrophilic component selected from the group consisting of polyhydric alcohols, lower alkyl ethers, and short chain esters; wherein the hydrophilic component is present in a total amount of at least 8 wt-% and no greater than 50 wt-%, based on the weight of the ready to use composition;

a surfactant selected from a sulfonate surfactant, a sulfate surfactant, a phosphate surfactant, and mixtures thereof; wherein the surfactant is present in a total amount of at least 0.5 wt-% and no greater than 3 wt-%, based on the weight of the ready to use composition;

a hydrophobic component wherein the hydrophobic component has a solubility in water of less than 1% by weight at 23° C.; and wherein the hydrophobic component is present in a total amount of at least 30 wt-%, based on the weight of the ready to use composition; and an enhancer component with the proviso that when a chelator enhancer that includes carboxylic acid groups is present, at least one of the carboxylic acid groups is in the free acid form;

wherein the composition has a viscosity of greater than 100 cps;

wherein the mammalian tissue is at least a portion of the nasal cavity, the anterior nares, and/or the nasopharynx of a subject;

wherein the microorganisms comprise bacteria and the antimicrobial composition is used in an amount effective to kill one or more bacteria.

23. A method of killing or inactivating microorganisms on mammalian tissue, the method comprising contacting the affected area with an antimicrobial composition, the antimicrobial composition consisting essentially of:

an antiseptic selected from the group consisting of diphenyl ethers, halogenated phenols, bisphenols, halogenated carbanilides, salicylanilides, and combinations thereof, wherein the composition includes a total amount of the antiseptic of at least 1 wt-% and no greater than 6 wt-%, based upon the total weight of the composition as used, a hydrophilic component selected from the group consisting of polyhydric alcohols, lower alkyl ethers, and short chain esters; wherein the hydrophilic component is present in a total amount of at least 8 wt-%, based on the weight of the ready to use composition;

a surfactant selected from a sulfonate surfactant, a sulfate surfactant, a phosphate surfactant, and mixtures thereof; wherein the surfactant is present in a total amount of at least 0.5 wt-% and no greater than 3 wt-%, based on the weight of the ready to use composition; and a hydrophobic component; wherein the hydrophobic component has a solubility in water of less than 1% by weight at 23° C.; wherein the hydrophobic component is present in a total amount of at least 30 wt-%, based on the weight of the ready to use composition; and wherein the hydrophobic component is present in the greatest amount and not greater than 92 wt-% based on the weight of the ready to use composition;

wherein the composition has a viscosity of greater than 100 cps;

wherein the mammalian tissue is at least a portion of the nasal cavity, the anterior nares, and/or the nasopharynx of a subject;

wherein the microorganisms comprise bacteria and the antimicrobial composition is used in an amount effective to kill one or more bacteria.

24. A method of killing or inactivating microorganisms on mammalian tissue, the method comprising contacting the affected area with an antimicrobial composition, the antimicrobial composition comprising:

an antiseptic selected from the group consisting of diphenyl ethers, halogenated phenols, bisphenols, halogenated carbanilides, salicylanilides, and combinations thereof, wherein the composition includes a total amount of the antiseptic of at least 1 wt-% and no greater than 6 wt-%, based upon the total weight of the composition as used, a hydrophilic component selected from the group consisting of polyhydric alcohols, lower alkyl ethers, and short chain esters; wherein the hydrophilic component is present in the greatest amount and not greater than 60 wt-% based on the weight of the ready to use composition;

a surfactant selected from a sulfonate surfactant, a sulfate surfactant, a phosphate surfactant, and mixtures thereof; wherein the surfactant is present in a total amount of at least 0.5 wt-% and no greater than 3 wt-%, based on the weight of the ready to use composition; and a hydrophobic component; wherein the hydrophobic component has a solubility in water of less than 1% by weight at 23° C.; and wherein the hydrophobic component is present in a total amount of at least 30 wt-%, based on the weight of the ready to use composition;

wherein the composition has a viscosity of greater than 100 cps;

wherein the mammalian tissue is at least a portion of the nasal cavity, the anterior nares, and/or the nasopharynx of a subject; and wherein the microorganisms comprise bacteria and the antimicrobial composition is used in an amount effective to kill one or more bacteria.

25. The method of claim 19, wherein the surfactant is selected from a sulfonate surfactant, a sulfate surfactant, a phosphate surfactant, and mixtures thereof; wherein the surfactant is present in a total amount no greater than 3 wt-%, based on the weight of the ready to use composition.

* * * * *

UNITED STATES PATENT AND TRADEMARK OFFICE
CERTIFICATE OF CORRECTION

| | | |
|---|---|---|
| PATENT NO. | : 8,198,326 B2 | Page 1 of 3 |
| APPLICATION NO. | : 10/936171 | |
| DATED | : June 12, 2012 | |
| INVENTOR(S) | : Matthew Thomas Scholz | |

It is certified that error appears in the above-identified patent and that said Letters Patent is hereby corrected as shown below:

Title page,
Item [56], References Cited, OTHER PUBLICATIONS,

Line 6: Delete "Philidelphia" and insert -- Philadelphia --, therefor.

Line 15: Delete "Staphylococus" and insert -- Staphylococcus --, therefor.

Page 2,
Item [56], References Cited, OTHER PUBLICATIONS, Column 1:

Line 7: Delete "invections"," and insert -- infections", --, therefor.

Page 2,
Item [56], References Cited, OTHER PUBLICATIONS, Column 2:

Line 9: Delete "Hydorgels" and insert -- Hydrogels --, therefor.

Line 34: Delete "Postmiling" and insert -- Postmilking --, therefor.

Line 38: Delete "incidence of bacteiuria" and insert -- incidence of bacteriuria --, therefor.

Column 5, Line 41: Delete "Enterococcu)," and insert -- Enterococcus), --, therefor.

Column 9, Line 54: Delete "Esherichia" and insert -- Escherichia --, therefor.

Column 9, Line 61: Delete "auerginosa," and insert -- aeruginosa, --, therefor.

Column 10, Line 8: Delete "faciitis;" and insert -- fasciitis; --, therefor.

Column 11, Line 28: After "patients" delete "an" and insert -- and --, therefor.

Column 14, Line 16: Delete "here in" and insert -- herein --, therefor.

Column 14, Line 22: Delete "Crodaphos CES," and insert -- Crodafos CES, --, therefor.

Column 15, Line 44: Delete "-terabromo-" and insert -- -tetrabromo- --, therefor.

Column 15, Line 64: Delete "Philidelphia" and insert -- Philadelphia --, therefor.

Column 17, Line 63: Delete "Psuedomonas sp." and insert -- Pseudomonas sp. --, therefor.

Signed and Sealed this
Fourth Day of September, 2012

David J. Kappos
*Director of the United States Patent and Trademark Office*

CERTIFICATE OF CORRECTION (continued)
U.S. Pat. No. 8,198,326 B2

Column 21, Lines 53-54: Delete "200 uM" and insert -- 2000 uM --, therefor.

Column 23, Line 42: Delete "TPNB" and insert -- TPnB --, therefor.

Column 25, Line 9: Delete "tetralkyl" and insert -- tetraalkyl --, therefor.

Column 25, Line 19 (approx): Delete "aralklyl" and insert -- aralkyl --, therefor.

Column 25, Line 50 (approx): Delete "sufonates," and insert -- sulfonates, --, therefor.

Column 26, Line 21: Delete "(C12-16)" and insert -- (C12-C16) --, therefor.

Column 26, Line 50: Delete "CRODAPHOS SG" and insert -- CRODAFOS SG --, therefor.

Column 26, Line 50: Delete "Parsipanny, N.J.," and insert -- Parsippany, N.J., --, therefor.

Column 30, Line 36: Delete "isoparafins" and insert -- isoparaffins --, therefor.

Column 30, Line 40: Delete "isoparafins," and insert -- isoparaffins, --, therefor.

Column 31, Line 16-17: Delete "antinflammatory" and insert -- anti-inflammatory --, therefor.

Column 31, Line 43: Delete "clortrimazole," and insert -- clotrimazole, --, therefor.

Column 31, Line 63: Delete "iodopropylnyl" and insert -- iodopropynyl --, therefor.

Column 36, Line 18-19: Delete "betonite," and insert -- bentonite, --, therefor.

Column 36, Line 19: Delete "montmorrillonite" and insert -- montmorillonite, --, therefor.

Column 37, Line 15: Delete "Polyquatemium" and insert -- Polyquaternium --, therefor.

Column 38, Line 4: Delete "Masterisizer" and insert -- Mastersizer --, therefor.

Column 38, Lines 12-13: Delete "Masterisizer" and insert -- Mastersizer --, therefor.

Column 38, Line 29: Delete "Polyquatemium-4." and insert -- Polyquaternium-4. --, therefor.

Column 39, Line 33: Delete "Polyquatemium-16." and insert -- Polyquaternium-16. --, therefor.

Column 39, Line 38: Delete "Polyquatemium-11." and insert -- Polyquaternium-11. --, therefor.

Column 39, Line 41-42: Delete "dimethyldiallyammonium" and insert -- dimethyldiallylammonium --, therefor.

Column 39, Line 44: Delete "Polyquatemium 6" and insert -- Polyquaternium 6 --, therefor.

Column 39, Line 44: Delete "Polyquatemium 7," and insert -- Polyquaternium 7, --, therefor.

Column 41, Line 2: Delete "Polyquatemium-16)," and insert -- Polyquaternium-16), --, therefor.

Column 41, Line 5: Delete "Polyquatemium-28)." And insert -- Polyquaternium-28). --, therefor.

Column 41, Line 50: Delete "alklyl," and insert -- alkyl, --, therefor.

Column 41, Line 52: Delete "Arsitoflex" and insert -- Aristoflex --, therefor.

Column 42, Lines 29-30: Delete "(hexlmethacrylate)," and insert -- (hexylmethacrylate), --, therefor.

Column 42, Line 30: Delete "poly(isodecl" and insert -- poly(isodecyl --, therefor.

Column 42, Line 33: Delete "(octadecl" and insert -- (octadecyl --, therefor.

Column 45, Line 10: Delete "terephalate," and insert -- terephthalate, --, therefor.

Column 45, Line 10: Delete "polybutyleneterephalate," and insert -- polybutyleneterephthalate, --, therefor.

Column 45, Line 16: Delete "terephalate" and insert -- terephthalate --, therefor.

Column 45, Line 18: Delete "chlorotriflouroethylene" and insert -- chlorotrifluoroethylene --, therefor.

Column 45, Lines 19-20: Delete "perflourinated" and insert -- perfluorinated --, therefor.

Column 45, Line 21: Delete "tetraflouroethylene/" and insert -- tetrafluoroethylene/ --, therefor.

Column 45, Line 36: Delete "(CERAMIS" and insert -- (CERAMIC --, therefor.

Column 47, Line 28: Delete "ION" and insert -- 10N --, therefor.

Column 48, Line 3: Delete "Laboratoris," and insert -- Laboratories, --, therefor.

Column 49-50, Line 48 (Table 1): Delete "containedVAZO" and insert -- contained VAZO --, therefor.

Column 49-50, Line 50 (Table 1): Delete "dryingat" and insert -- drying at --, therefor.

Column 49-50, Line 53 (Table 1): Delete "solutionof" and insert -- solution of --, therefor.

Column 51, Line 28: Delete "(benalkonium" and insert -- (benzalkonium --, therefor.

Column 52, Line 26-27: Delete "2-pheoxyethanol," and insert -- 2-phenoxyethanol, --, therefor.

Column 55, Line 27 (Table 3): Delete "Docuate" and insert -- Docusate --, therefor.